(12) United States Patent
Browne

(10) Patent No.: US 7,070,933 B2
(45) Date of Patent: Jul. 4, 2006

(54) INVERSION PROBES

(75) Inventor: Kenneth A. Browne, Poway, CA (US)

(73) Assignee: Gen-Probe Incorporated, San Diego, CA (US)

( * ) Notice: Subject to any disclaimer, the term of this patent is extended or adjusted under 35 U.S.C. 154(b) by 496 days.

(21) Appl. No.: 10/388,918

(22) Filed: Mar. 14, 2003

(65) Prior Publication Data
US 2004/0005595 A1 Jan. 8, 2004

Related U.S. Application Data

(63) Continuation-in-part of application No. 10/259,272, filed on Sep. 27, 2002, now abandoned.

(60) Provisional application No. 60/325,600, filed on Sep. 28, 2001.

(51) Int. Cl.
*C12Q 1/68* (2006.01)
*C12P 19/34* (2006.01)
*C07H 21/02* (2006.01)
*C07H 21/04* (2006.01)
*C07H 21/00* (2006.01)

(52) U.S. Cl. .................. 435/6; 435/91.1; 536/23.1; 536/24.3; 536/24.33; 536/25.3; 536/25.32

(58) Field of Classification Search ............... 536/23.1, 536/24.3, 24.33, 25.3, 25.32; 435/6, 91.1, 435/183; 436/94, 501
See application file for complete search history.

(56) References Cited

U.S. PATENT DOCUMENTS

| | | | |
|---|---|---|---|
| 5,312,728 | A | 5/1994 | Lizardi et al. |
| 5,484,908 | A | 1/1996 | Froehler et al. |
| 5,502,177 | A | 3/1996 | Matteucci et al. |
| 5,594,121 | A | 1/1997 | Froehler et al. |
| 5,594,122 | A | 1/1997 | Friesen |
| 5,645,985 | A | 7/1997 | Froehler et al. |
| 5,677,439 | A | 10/1997 | Weis et al. |
| 5,721,218 | A | 2/1998 | Froehler |
| 5,750,669 | A | 5/1998 | Rosch et al. |
| 5,763,588 | A | 6/1998 | Matteucci et al. |
| 5,780,610 | A | 7/1998 | Collins et al. |
| 5,811,537 | A | 9/1998 | Friesen |
| 5,830,653 | A | 11/1998 | Froehler et al. |

(Continued)

FOREIGN PATENT DOCUMENTS

WO    WO 91/06626 A2    5/1991

(Continued)

OTHER PUBLICATIONS van de Sande et al., Science 214 (4865) : 551-557 (1988).*

(Continued)

*Primary Examiner*—Frank W. Lu
(74) *Attorney, Agent, or Firm*—Michael J. Gilly

(57) ABSTRACT

Unitary hybridization probes having stem-and-loop structures, wherein the stem portion of the structure comprises a pair of interactive arms that are substantially prevented from interacting with target polynucleotides. One arm of the invented parallel-stem hybridization probe has a backbone polarity opposite that of the target-complementary loop sequence of the probe. Rather than interacting in an antiparallel fashion, the arms of parallel-stem hybridization probes interact in a parallel fashion. The arms of the invented dual inversion probes interact in a conventional antiparallel fashion, but have backbone polarities opposite that of the target-complementary loop portion of the probe. Arm portions of the inversion probes do not substantially contribute to sequence-dependent stabilization of probe: target hybrids. Incorporating inversion linkages into the structures of these probes dramatically simplifies the process of designing stem-and-loop hybridization probes.

19 Claims, 13 Drawing Sheets

U.S. PATENT DOCUMENTS

| | | | | |
|---|---|---|---|---|
| 5,888,733 | A | | 3/1999 | Hyldig-Nielsen et al. |
| 5,925,517 | A | * | 7/1999 | Tyagi et al. ............... 435/6 |
| 6,001,657 | A | | 12/1999 | Hardin et al. |
| 6,005,096 | A | | 12/1999 | Matteucci et al. |
| 6,007,992 | A | | 12/1999 | Lin et al. |
| 6,028,183 | A | | 2/2000 | Lin et al. |
| 6,037,120 | A | | 3/2000 | Benner |
| 6,037,130 | A | | 3/2000 | Tyagi et al. |
| 6,103,476 | A | | 8/2000 | Tyagi et al. |
| 6,147,199 | A | | 11/2000 | Seela et al. |
| 6,150,097 | A | * | 11/2000 | Tyagi et al. ............... 435/6 |
| 6,235,484 | B1 | * | 5/2001 | Hogan et al. ............... 435/6 |
| 6,235,887 | B1 | | 5/2001 | Froehler et al. |
| 6,355,421 | B1 | | 3/2002 | Coull et al. |

FOREIGN PATENT DOCUMENTS

| | | |
|---|---|---|
| WO | WO 92/10590 A1 | 6/1992 |
| WO | WO 93/09127 A1 | 5/1993 |
| WO | WO 93/10820 A1 | 6/1993 |
| WO | WO 94/24144 A2 | 10/1994 |
| WO | WO 95/00638 A2 | 1/1995 |
| WO | WO 95/07918 A2 | 3/1995 |
| WO | WO 99/09045 A1 | 2/1999 |
| WO | WO 99/24452 A2 | 5/1999 |
| WO | WO 99/64625 A2 | 12/1999 |
| WO | WO 01/32924 A1 | 5/2001 |
| WO | WO 02/101092 A2 | 12/2002 |

OTHER PUBLICATIONS

The Stratagene Catalog p. 39 (1988).*

Aramini et al., "Spectroscopic and Thermodynamic Studies of DNA Duplexes Containing (alpha) Anomeric C, A, and G Nucleotides and Polarity Reversals: Coexistence of Localized Parallel and Antiparallel DNA", Biochemistry, Aug. 1997, 36(32):9715-9725.

Aramini et al., "Structure of a DNA Duplex That Contains (alpha) Anomeric Nucleotides and 3'-3' and 5'-5' Phosphodiester Linkages: Coexistence of Parallel and Antiparallel DNA", Biochemistry, Jul. 1996, 35(29):9355-9365.

Bernacchi et al., "Exciton Interaction In Molecular Beacons: A Sensitive Sensor for Short Range Modifications of the Nucleic Acid Structure", Nucleic Acids Research, Jul. 2001, 29(13):e62-2, pp. 1-8.

Borisova et al., "Relative Stability of AT and GC Pairs in Parallel DNA Duplex Formed by a Natural Sequence", Federation of European Biochemical Societies (FEBS), May 1993, 322(3):304-306.

Brown et al., "Molecular Beacons Attached to Glass Beads Fluoresce Upon Hybridisation to Target DNA", Chem. Commun., 2000, 621-622.

Chen et al., "Stability and Structure of RNA Duplexes Containing Isoguanosine and Isocytidine", J. Am. Chem. Soc., Feb. 2001, 123(7):1267-1274.

Dornberger et al., "Hairpin-Dimer Equilibrium of a Parallel-Stranded DNA Hairpin: Formation of a Four-Stranded Complex", Nucleic Acids Research, Feb. 1997, 25(4):822-829.

Evertsz et al., "Parallel-Stranded Duplex DNA Containing Blocks of Trans Purine—Purine and Purine— Pyrimidine Base Pairs", Nucleic Acids Research, Aug. 1994, 22(16):3293-3303.

Fang et al., "Designing a Novel Molecular Beacon for Surface-Immobilized DNA Hybridization Studies", J. Am. Chem. Soc., 1999, 121:2921-2922.

Fang et al., "Molecular Beacons Novel Fluorescent Probes", Anal. Chem., Dec. 2000, 72(23):747A-753A.

Fortsch et al., "Parallel-Stranded Duplex DNA Containing dA—dU Base Pairs", Biopolymers, Feb. 1996, 38(2):209-220.

Fortsch et al., "Studies on the Interaction of DNA-Ligands with Modified Parallel-Stranded Duplex-DNA Oligomers", Nucleosides & Nucleotides, 1998, 17(9-11):1539-1545.

Garcia et al., "Dynamics and Relative Stabilities of Parallel- and Antiparallel-Stranded DNA Duplexes", Biophysical Journal, Jun. 1994, 66(6):1742-1755.

Germann et al., "Characterization of a Parallel-Stranded DNA Hairpin", Biochemistry, Jul. 1989, 28(15):6220-6228.

Germann et al., "DNA Duplexes Containing Alpha Anomeric Nucleotides and Polarity Reversals: Coexistence of Parallel and Antiparallel DNA", Nucleosides & Nucleotides, 1997, 16(7-9):1481-1485.

Germann et al., "Length-Dependent Formation of Parallel-Stranded DNA in Alternating AT Segments", Biochemistry, Oct. 1990, 29(40):9426-9432.

Germann et al., "Structure of d(GT)n-d(GA)n Sequences: Formation of Parallel Stranded Duplex DNA", Biochemistry, Sep. 1998, 37(37):12962-12970.

Prevot-Halter et al., "Selective Recognition of a C-G Base-Pair in the Parallel DNA Triple-Helical Binding Motif", Bioorganic & Medicinal Chemistry Letters, Sep. 1999, 9(18):2657-2660.

Kandimalla et al., "Single Strand Targeted Triplex Formation: Parallel-Stranded DNA Hairpin Duplexes for Targeting Pyrimidine Strands", J. Am. Chem. Soc., 1995, 117:6416-6417.

Leone et al., "Molecular Beacon Probes Combined with Amplification by NASBA Enable Homogeneous, Real-Time Detection of RNA", Nucleic Acids Research, May 1998, 26(9):2150-2155.

Li et al., "Molecular Beacon-Based Homogeneous Fluorescence PCR Assay for the Diagnosis of Infectious Diseases", Analytical Sciences, Feb. 2000, 16:245-248.

Liu et al., "A Fiber-Optic Evanescent Wave DNA Biosensor Based on Novel Molecular Beacons", Anal. Chem., Nov. 1999, 71(22):5054-5059.

Liu et al., "A Novel DNA Duplex. A Parallel-Stranded DNA Helix with Hoogsteen Base Pairing", Biochemistry, Nov. 1993, 32(44):11802-11809.

Liu et al., "Molecular Beacons for DNA Biosensors with Micrometer to Submicrometer Dimensions", Analytical Biochemistry, Jul. 2000, 283(1):56-63.

Mohammadi et al., "FTIR and UV Spectroscopy of Parallel-Stranded DNAs with Mixed A-T/G-C Sequences and Their A-T/I-C Analogues", Biochemistry, Nov. 1998, 37(47):16529-16537.

Otto et al., "The Hydogen-Bonding Structure in Parallel-Stranded Duplex DNA Is Reverse Watson-Crick", Biochemistry, Mar. 1991, 30(12):3062-3069.

Raghunathan et al., "Parallel Nucleic Acid Helices with Hoogsteen Base Pairing: Symmetry and Structure", Biopolymers, Dec. 1994, 34(12):1573-1581.

Ramsing et al., "Helix-Coil Transition of Parallel-Stranded DNA. Thermodynamics of Hairpin and Linear Duplex Oligonucleotides", Biochemistry, Nov. 1989, 28(24):9528-9535.

Ren et al., "The Parallel and Antiparallel Triplex Formation and Stability of Self Complementary Oligonucleotides Containing 2'-Fluoro-Arabinosyl Thymine and 5-Methyl-2'-Deoxycytidine, Nucleosides & Nucleotides", 1998, 17(9-11):2103-2116.

Rentzeperis et al., "Differential Hydration of dA-dT Base Pairs in Parallel-Stranded DNA Relative to Antiparallel DNA", Biochemistry, Aug. 1994, 33(32):9588-9591.

Rippe et al., "Alternating d(G-A) Sequences Form a Parallel-Stranded DNA Homoduplex", EMBO J, Oct. 1992, 11(10):3777-3786.

Rippe et al., "A Parallel Stranded Linear DNA Duplex Incorporating dG—dC Base Pairs", Journal of Biomolecular Structure & Dynamics, Jun. 1990, 7(6):1199-1209.

Rippe et al., "Spectroscopic Properties and Helical Stabilities of 25-nt Parallel-Stranded Linear DNA Duplexes", Biochemistry, Nov. 1989, 28(24):9536-9541.

Rippe et al., "Substrate Properties of 25-nt Parallel-Stranded Linear DNA Duplexes", Biochemistry, Nov. 1989 28(24):9542-9549.

Robinson et al., "5'-CGA Motif Induces Other Sequences to Form Homo Base-Paired Parallel-Stranded DNA Duplex: The Structure of (G-A)n Derived from Four DNA Oligomers Containing (G-A)3 Sequence", J. Am. Chem. Soc., 1994, 116:1565-1566.

Robinson et al., "5'-CGA Sequence is a Strong Motif for Homo Base-Paired Parallel-Stranded DNA Duplex as Revealed by NMR Analysis", Proc. Natl. Acad. Sci. USA, Jun. 1993, 90(11):5224-5228.

Robinson et al., "Unusual DNA Conformation at Low pH Revealed by NMR: Parallel-Stranded DNA Duplex with Homo Base Pairs", Biochemistry, Nov. 1992, 31(43):10510-10517.

Rohozinski et al., "Polycytosine Regions Contained in DNA Hairpin Loops Interact Via a Four-Stranded, Parallel Structure Similiar to the i-motif", Nucleic Acids Research, Nov. 1994, 22(22):4653-4659.

Seela et al., "2'-Deoxyuridine and 2'-Deoxyisocytidine as Constituents of DNA with Parallel Chain Orientation: The Stabilization of the iCd—Gd Base Pair by the 5-Methyl Group", Helv. Chim. Acta, 2000, 83:2527-2540.

Seela et al., "N7-DNA: Base-Pairing Properties of N7-(2'-Deoxy-(alpha)-D-erythro-pentofuranosyl)-Substituted Adenine, Hypoxanthine, and Guanine in Duplexes with Parallel Chain Orientation", Helv. Chim. Acta, 1998, 81:2244-2263.

Seela et al., "Oligonucleotides Containing Consecutive 2'-Deoxy-Isoguanosine Residues: Synthesis, Parallel Duplex Formation and Identification of A d(T4ig4T4) Tetraplex", Nucleosides & Nucleotides, 1997, 16(7-9):1523-1527.

Seela et al., "Oligonucleotides Containing Consecutive 2'-Deoxylsoguanosine Residues: Synthesis, Duplexes with Parallel Chain Orientation, and Aggregation", Helv. Chim. Acta, 1997, 80:73-85.

Seela et al., "Parallel-Stranded DNA Formed by New Base Pairs Related to the Isoguanine-Cytosine or Isocytosine-Guanine Motifs", Nucleosides & Nucleotides, 1999, 18(6&7);1543-1548.

Seela et al., "Parallel-Stranded Duplex DNA and Self-Assembled Quartet Structures Formed by Isoguanine and Related Bases", Nucleosides & Nucleotides, 1998, 17(9-11):2045-2052.

Seela et al., "Parallel-Stranded Duplex DNA Formed by a New Base Pair Between Guanine and 5-Aza-7-Deazaguanine", Bioorganic & Medicinal Chemistry Letters, 1997, 7(17);2173-2176.

Seela et al., "The Influence of Modified Purine Bases on the Stability of Parallel DNA", Bioorganic & Medicinal Chemistry Letters, Feb. 2000, 10(3):289-292.

Sha et al., "Parallel Helical Domains in DNA Branched Junctions Containing 5',5' and 3',3' Linkages", Biochemistry, Mar. 1999, 38(9):2832-2841.

Shchyolkina et al., "Parallel-Stranded DNA with Mixed AT/GC Composition: Role of Trans G-C Base Pairs in Sequence Dependent Helical Stability", Biochemistry, Aug. 2000, 39(33):10034-10044.

Shchyolkina et al., "Parallel-Stranded Oligonucleotides With Alternating d(A-isoG)/d(T-C) and d(A-G)/d(T-m5isoC) Sequences", Nucleosides & Nucleotides, 1999, 18(6&7):1555-1562.

Singh et al., "Structural Polymorphism and Dynamism in the DNA Segment GATCTTCCCCCCGGAA: NMR Investigations of Hairpin, Dumbbell, Nicked Duplex, Parallel Strands, and i-Motif", Biochemistry, Oct. 1997, 36(43):13214-13222.

Suda et al., "Formation of a Parallel-Stranded DNA Homoduplex by d(GGA) Repeat Oligonucleotides", Nucleic Acids Research, Sep. 1995, 23(18):3771-3777.

Sugiyama et al., "Remarkably Stable Parallel-Stranded Oligonucleotides Containing 5-Methylisocytosine and Isoguanine", J. Am. Chem. Soc., 1996, 118(41):9994-9995.

Tapp et al., "Homogeneous Scoring of Single-Nucleotide Polymorphisms: Comparison of the 5'-Nuclease TaqMan Assay and Molecular Beacon Probes", BioTechniques, Apr. 2000, 28(4):732-738.

Tyagi et al., "Molecular Beacons: Probes that Fluoresce upon Hybridization", Nature Biotechnology, Mar. 1996, 14(3):303-308.

Tyagi et al., "Wavelength-Shifting Molecular Beacons", Nature Biotechnology, Nov. 2000, 18(11):1191-1196.

Yamamoto et al., "Molecular Beacon Aptamer Fluoresces in the Presence of Tat Protein of HIV-1", Genes to Cells, May 2000, 5(5):389-396.

Yang et al., "Structural Studies of a Stable Parallel-Stranded DNA Duplex Incorporating Isoguanine: Cytosine and Isocytosine: Guanine Basepairs by Nuclear Magnetic Resonance Spectroscopy", Biophysical Journal, Sep. 1998, 75(3):1163-1171.

* cited by examiner

{1261} 5'-                    AAAAAAAAAAAAGCAGGATGAAGAGGAA            TTTTTTTTTTTT           -3' (SEQ ID NO:6)
{1269} 3'-TATTCTTCTACTCCGTATCGTCGTCCTACTTCTCCTT                        ATACTATTTGCGGCGTCTG-5'    (SEQ ID NO:7)

{1262} 5'-                    AAAAAAAAAAAAGCAGGATGAAGAGGAA-3'-3'-TTTTTTTTTTTT           -5' (SEQ ID NO:8)
{1269} 3'-TATTCTTCTACTCCGTATCGTCGTCCTACTTCTCCTT                        ATACTATTTGCGGGCGTCTG-5'   (SEQ ID NO:7)

FIG. 7

INVERSION PROBES

RELATED APPLICATION

This is a continuation-in-part of U.S. patent application Ser. No. 10/259,272, filed on Sep. 27, 2002, now abandoned, which claims the benefit of U.S. Provisional Application No. 60/325,600, filed on Sep. 28, 2001.

FIELD OF THE INVENTION

The present invention relates to the field of nucleic acid detection. More specifically, the invention relates to labeled, unitary hybridization probes having stem-and-loop structures, wherein the stem comprises arm structures that cannot substantially interact with target sequences.

BACKGROUND OF THE INVENTION

Hybridization probes used for nucleic acid detection generally are single-stranded molecules complementary to a nucleic acid sequence sought to be detected ("target sequence"). Background descriptions of the use of nucleic acid hybridization as a procedure for the detection of particular nucleic acid sequences are given by Kohne in U.S. Pat. No. 4,851,330, and by Hogan et al., in U.S. Pat. No. 5,840,488. Hybridization probes may be labeled with detectable moieties such as radioisotopes, antigens or chemiluminescent moieties. When a first single strand of nucleic acid contains sufficient contiguous complementary bases to a second, and the two strands are brought together under conditions which promote hybridization, double stranded nucleic acid will result. Under appropriate conditions, DNA/DNA, RNA/DNA, or RNA/RNA hybrids may be formed.

Molecular beacons are examples of hybridization probes that have limited regions of self-complementarity. These probes, which are particularly useful for conducting homogeneous detection assays, comprise a target-complementary "loop" portion, a "stem" portion formed by the annealing of two complementary "arms" that extend from the loop, a fluorophore group and a quencher group. The fluorophore is typically linked to the end of one arm while the quencher is typically linked to the end of the other arm. The stem portion maintains the probe in a closed conformation in the absence of a target nucleic acid sequence, so that energy received by the fluorophore is transferred to the quencher, rather than being emitted. Upon hybridizing a target polynucleotide, the complementary arm sequences of the molecular beacon become separated, thereby shifting the probe to an open conformation. This shift is detectable as a flourescent signal resulting from the reduced energy transfer between the fluorophore and the quencher (see Tyagi et al., *Nature Biotechnology* 14:303 (1996); Fang et al., *Analytical Chemistry,* Dec. 1, 2000 issue:747A). Molecular beacons are fully described in U.S. Pat. Nos. 5,925,517 and 6,150,097, the disclosures of which are hereby incorporated by reference.

Molecular beacons are not limited to having conventional nucleic acid constituents. In addition to standard nucleotides, peptide nucleic acids (PNAs) have also been used for preparing molecular beacons (see published International Patent Application No. PCT/US98/22785). Regardless of whether conventional nucleotides or PNA analogs were used to prepare these probes, stem regions uniformly were complementary as the result of antiparallel pairing of nucleobases disposed on sugar-phosphate or glycyl peptide backbones.

Molecular beacon probe design is naturally rendered somewhat more complicated than the process of designing linear probes due to the added presence of the stem structure. Since the stem portions of previously described molecular beacons comprised base moieties that conceivably could interact through complementary pairing with bases present in the target polynucleotide that is to be detected, those interactions must be considered during the design of every molecular beacon. Thus, the process of designing a molecular beacon requires selection of a target-complementary sequence for the loop portion of the probe, as well as consideration of the effect that the base sequence of the stem portion will have on interaction with the target polynucleotide that is to be detected.

Previous attempts to simplify the process of designing molecular beacons have focused on the use of a "universal stem" structure. For example, in U.S. Pat. No. 6,103,476, Tyagi et al., described stems consisting of arm regions that comprised nucleobase sequences orientated by standard antiparallel complementarity, with one of the arms being linked to a fluorophore and the other arm being linked to a quencher moiety. In these constructs it remained possible for nucleobases of the universal stem to influence hybridization between the target polynucleotide and the molecular beacon probe, for example by influencing the Tm of the probe:target complex. Notably, this same feature would also characterize universal stems comprised of PNAs because the nucleobases of the denatured stem could still interact with the target sequence.

The present invention provides a new class of hybridization probes wherein opportunities for complementary interactions between nucleobases of a target polynucleotide and nucleobases of the stem region of a molecular beacon are substantially eliminated. Additionally, these new probes have been shown to have unique properties that distinguish them from previously known hybridization probes.

SUMMARY OF THE INVENTION

A first aspect of the invention regards a hybridization probe that can be used for detecting a target polynucleotide. The invented probe includes a loop region, a first arm, a second arm, and at least one detectable label. The loop region includes a target-complementary sequence of bases joined to a loop backbone, with the target-complementary sequence of bases extending from a first boundary to a second boundary. The first arm, which includes a first arm sequence of bases joined to a first arm backbone, is joined to the target-complementary sequence of bases at its first boundary through a first arm linkage. The second arm, which includes a second arm sequence of bases joined to a second arm backbone, is joined to the target-complementary sequence of bases at its second boundary through a second arm linkage. Finally, there is at least one detectable label joined to the hybridization probe by any of the loop region, the first arm or the second arm. Significantly, at least one of the first and second arm linkages is an inversion linkage. Also significant, the first arm and the second arm interact with each other in the absence of the target polynucleotide to form a stem duplex.

If only one of the first and second arm linkages is an inversion linkage, then the hybridization probe is a parallel-stem hybridization probe. For example, if the first arm linkage of a parallel-stem hybridization probe is an inversion linkage, then the first arm is an "inversion arm" and the second arm is an "extension arm." In accordance with certain embodiments of the invention, the detectable label of the parallel-stem hybridization probe includes a pair of interactive labels, with the first label being joined to the first arm and the second label being joined to the second arm. In accordance with one embodiment of the parallel-stem hybridization probe, at least one of the loop, the inversion arm or the extension arm includes at least one nucleotide analog. For example, the nucleotide analog may particularly be any of a 2'-methoxy nucleotide analog, an isocytosine nucleotide analog and an isoguanine nucleotide analog. In accordance with another embodiment, the first arm of the parallel-stem hybridization probe is an inversion arm, the second arm is an extension arm, and the inversion arm and the extension arm both include deoxyribonucleotides. In a highly preferred embodiment, the loop includes 2'-methoxy nucleotide analogs. When the first arm linkage of a parallel-stem hybridization probe is an inversion linkage, the inversion linkage can be either a 5'-5' inversion linkage or a 3'-3' inversion linkage. If the inversion linkage of the parallel-stem hybridization probe is a 5'-5' inversion linkage, then the inversion arm and the extension arm both have 3' termini. Alternatively, if the inversion linkage of the parallel-stem hybridization probe is a 3'-3' inversion linkage, then the inversion arm and the extension arm both have 5' termini. In a preferred embodiment, when the hybridization probe is a parallel-stem hybridization probe, the extension arm has a length of from 5–12 bases. Still more preferably, when the hybridization probe is a parallel-stem hybridization probe the extension arm has a length of from 5–12 bases, the inversion arm also has a length of from 5–12 bases. In another preferred embodiment, when the hybridization probe is a parallel-stem hybridization probe, both the extension arm and the inversion arm have lengths in the range of from 6–8 bases. In other embodiments of the invented hybridization probe, when the detectable label includes a pair of interactive labels, with the first label being joined to the first arm and the second label being joined to the second arm, the pair of interactive labels is a pair of FRET interactive labels. In still other embodiments of the invented hybridization probe, when the detectable label includes a pair of interactive labels, with the first label being joined to the first arm and the second label being joined to the second arm, the pair of interactive labels is a pair of non-FRET interactive labels. In a particular instance, fluorescein is one member of the pair of non-FRET interactive labels. In accordance with certain embodiments of the invented parallel-stem hybridization probe, when at least one of the loop, the inversion arm or the extension arm includes at least one nucleotide analog, it is the extension arm that includes at least one nucleotide analog. For example, this nucleotide analog can be any of isocytosine and isoguanine. In accordance with certain other embodiments of the invented parallel-stem hybridization probe, when at least one of the loop, the inversion arm or the extension arm includes at least one nucleotide analog, it is the inversion arm that includes at least one nucleotide analog.

If both the first arm linkage and the second arm linkage of the invented hybridization probe are inversion linkages which are different from each other, then the hybridization probe is a dual inversion probe. In separate versions of the invented dual inversion probe, either the first arm linkage is a 3'-3' inversion linkage and the second arm linkage is a 5'-5' inversion linkage, or the first arm linkage is a 5'-5' inversion linkage and the second arm linkage is a 3'-3' inversion linkage. In accordance with certain embodiments of the invention, the detectable label of the dual inversion probe includes a pair of interactive labels, with the first label being joined to the first arm and the second label being joined to the second arm of the probe. In certain preferred embodiments of the invention, at least one of the loop, the first arm or the second arm of the dual inversion probe include at least one nucleotide analog. For example, the loop may include 2'-methoxy nucleotide analogs. In accordance with other embodiments of the invented dual inversion probe, the target-complementary sequence of bases has a length in the range of from 10–25 bases, or more preferably 16–22 bases. When the target-complementary sequence of bases contained within a dual inversion probe has a length in the range of from 16–22 bases, the first arm can have a length of from 5–12 bases. More preferably, when the target-complementary sequence of bases contained within a dual inversion probe has a length in the range of from 16–22 bases, and when the first arm has a length of from 5–12 bases, the second arm has a length of from 5–12 bases. In accordance with another preferred embodiment, when the target-complementary sequence of bases contained within a dual inversion probe has a length in the range of from 10–25 bases, both the first arm and the second arm have lengths in the range of from 6–8 bases. In accordance with still another embodiment of the invented dual inversion probe, there is included a pair of interactive labels, more particularly a pair of FRET interactive labels. Alternatively, the dual inversion probe can include a pair of interactive labels, more particularly a pair of non-FRET interactive labels. In a highly preferred embodiment, one member of the pair of non-FRET interactive labels is fluorescein. In accordance with yet another highly preferred embodiment of the invented dual inversion probe, when the target-complementary sequence of bases has a length in the range of from 16–22 bases, when the first arm has a length of from 5–12 bases, and when the second arm has a length of from 5–12 bases, the pair of interactive labels is a pair of FRET interactive labels. In accordance with still yet another highly preferred embodiment of the invented dual inversion probe, when the target-complementary sequence of bases has a length in the range of from 16–22 bases, when the first arm has a length of from 5–12 bases, and when the second arm has a length of from 5–12 bases, the pair of interactive labels is a pair of non-FRET interactive labels.

In accordance with certain general embodiments of the invented hybridization probe, including parallel-stem hybridization probes and dual inversion probes, the target-complementary sequence of bases has a length in the range of from 10–25 bases, or more preferably a length in the range of from 16–22 bases.

A second aspect of the invention regards a method of determining whether a test sample contains a target polynucleotide. This method involves first providing a hybridization probe, as described above. Next, there is a step for contacting the hybridization probe with any of the target polynucleotide that may be present in the test sample under hybridization-promoting conditions. Finally, there is a step for detecting the formation of hybrid duplexes which include the hybridization probe and the target polynucleotide as an indication of the presence of the target polynucleotide sequence in the test sample.

A third aspect of the invention regards a kit for detecting a target polynucleotide sequence using a hybridization assay. The kit typically includes a hybridization probe, as described above; and a positive-control target polynucleotide having a sequence complementary to the target-complementary sequence of bases of the loop portion of the hybridization probe. In a preferred embodiment, the kit further includes a hybridization solution.

Definitions

As used herein, the following terms have the following meanings unless expressly stated to the contrary.

As used herein, a "molecular beacon" or "molecular beacon probe" is a nucleobase probe, having a stem-and-loop structure, that hybridizes specifically to a target polynucleotide under conditions that promote hybridization to form a detectable hybrid. Molecular beacons have been described in U.S. Pat. Nos. 5,925,517 and 6,150,097, the disclosures of these references having been incorporated by reference herein above.

As used herein, an "inversion linkage" refers to the chemical linkage which joins the backbone of one portion of a polynucleotide to the backbone of an adjacent portion of the same polynucleotide having an opposite orientation. The term particularly embraces 5'-5' and 3'-3' linkages in conventional nucleic acids. Also falling within the scope of the term are linkages that may be found in nucleic acid analogs, such as amino-amino and carboxy-carboxy linkages that may be found in peptide nucleic acids or other peptide bond-linked nucleic acid analogs. Notably, an inversion linkage may include a "non-nucleotide linker" which may be detectably labeled, or joined to a detectable label. Exemplary non-nucleotide linkers are described in the working Examples, and in U.S. Pat. No. 6,031,091, entitled "Non-Nucleotide Linking Reagents for Nucleotide Probes." Inversion linkages are present in both parallel-stem hybridization probes and dual inversion probes.

As used herein, an "inversion arm" of a parallel-stem hybridization probe is a single strand of polynucleotide that extends from one boundary of the target-complementary loop of the probe, and that is able to form a stem duplex upon hybridization with the extension arm of the parallel-stem hybridization probe. The inversion arm corresponds to the segment of the probe that is positioned between the inversion linkage and the nearest probe terminus, and may include nucleobase analogs.

As used herein, an "extension arm" of a parallel-stem hybridization probe is a single strand of polynucleotide that extends from the boundary of the target-complementary loop of the probe opposite the inversion arm, and that is able to form a stem duplex upon hybridization with the inversion arm of the parallel-stem hybridization probe. Preferably, the extension arm contains nucleobases or nucleobase analogs that preferentially form base pairs with a parallel orientation.

As used herein, a "detectable label" is a chemical species that can be detected or can lead to a detectable response. Detectable labels in accordance with the invention can be linked to probes either directly or indirectly. With particular reference to the use of detectable labels that are members of an interactive label pair, it is highly preferred for one member of the label pair to be a fluorophore, and for the other member of the label pair to be a quencher. Examples of fluorophores and quenchers are given at column 5 in U.S. Pat. No. 6,037,130.

As used herein, an "oligonucleotide" or "oligomer" is a polymeric chain of at least two, generally between about five and about 100, chemical subunits, each subunit comprising a nucleobase moiety, and a linking moiety that joins the subunits in a linear spacial configuration. In DNA and RNA the linking moiety will include a sugar moiety. Common "base" or nucleobase moieties are guanine (G), adenine (A), cytosine (C), thymine (T) and uracil (U), although other rare or modified nucleotide bases able to base pair are well known to those skilled in the art. Oligonucleotides may be purified from naturally occurring sources, but preferably are synthesized using any of a variety of well known enzymatic or chemical methods.

As used herein, "polynucleotide" means either RNA or DNA, along with any synthetic nucleotide analogs or other molecules that may be present in the sequence and that do not prevent hybridization of the polynucleotide with a second molecule having a substantially complementary sequence. The term includes polymers containing analogs of naturally occurring nucleotides and particularly includes analogs having a methoxy group (OMe) at the 2' position of the ribose.

An "analyte polynucleotide" is a target polynucleotide that is to be detected, quantified or replicated by a nucleic acid amplification process.

By "target" or "target polynucleotide" is meant a specific deoxyribonucleotide or ribonucleotide molecule containing a target nucleobase sequence which may be hybridized by a probe or amplification primer. Exemplary targets include viral polynucleotides, bacterial polynucleotides (such as rRNA), and eukaryotic mRNA. In the context of nucleic acid amplification reactions, a target polynucleotide includes a target sequence to be replicated, which may be either single-stranded or double-stranded, and which may include sequences in addition to the target sequence.

As used herein, "amplification" or "nucleic acid amplification" or "polynucleotide amplification" refers to an in vitro procedure for obtaining multiple copies of a target nucleic acid sequence, its complement or fragments thereof.

An "amplicon" is a polynucleotide product generated in an amplification reaction.

An "analyte amplicon" is a polynucleotide product of an amplification reaction wherein an analyte polynucleotide served as the template for synthesis of polynucleotide copies or amplification products.

"Homogeneous" assay formats employing hybridization probes do not require removal of unhybridized probe to determine accurately the extent of specific probe binding.

By "consisting essentially of" is meant that additional component(s), composition(s) or method step(s) that do not materially change the basic and novel characteristics of the present invention may be included in the compositions or kits or methods of the present invention. Such characteristics include the ability to selectively detect and quantify analyte polynucleotides in biological samples such as whole blood, plasma or urine. Any component(s), composition(s), or method step(s) that have a material effect on the basic and novel characteristics of the present invention would fall outside of this term.

BRIEF DESCRIPTION OF THE DRAWINGS

FIG. 5A shows results for the 1093 molecular beacon and the 1059 target (●) or the 1061 target (■). FIG. 5B shows results for the 1094 parallel-stem hybridization probe and the 1059 target (○) or the 1061 target (□). FIG. 5C shows signal-to-noise ratios calculated for the 1059:1093 (●) and 1059:1094 (○) data points in FIGS. 5A and 5B plotted against increasing amounts of target polynucleotide.

FIG. 6A represents fluorescence signal results obtained using the 1093 probe at concentrations of 0.3 µM (▲), 0.25 µM (◇), 0.2 µM (■), 0.15 µM (▽), and 0.1 µM (●). FIG. 6B represents S/N results calculated from the information presented in FIG. 6A. FIG. 6C represents the fluorescence signal results obtained using the 1094 probe at concentrations of 0.2 µM (■), 0.15 µM (▽), 0.1 µM (●), and 0.05 µM (□). FIG. 6D represents S/N results calculated from the information presented in FIG. 6C. FIG. 6E represents the fluorescence signal results obtained using combinations of the 1093 and 1094 probes at different concentrations. These combinations included 1093/1094 at 0.3 µM/0 µM (▲); 1093/1094 at 0.25 µM/0.05 µM (◇); 1093/1094 at 0.2 µM/0.1 µM (■); 1093/1094 at 0.15 µM/0.15 µM (▽); and 1093/1094 at 0.1 µM/0.2 µM (●). FIG. 6F represents S/N results calculated from the information presented in FIG. 6E. The symbols shown in FIGS. 6B, 6D and 6F correspond to the symbols shown in FIGS. 6A, 6C and 6E, respectively.

FIG. 7 is a nucleotide sequence alignment showing the 1261 molecular beacon and the 1262 parallel-stem hybridization probe hybridized with a target polynucleotide. Vertical lines in the alignments indicate complementary nucleobase interactions. The sequence of the 1269 target is presented in the 3' to 5' orientation to show complementarity with the probe sequences. Label moieties are omitted from the illustration.

FIG. 9A shows a line diagram representing the structure of an example parallel-stem hybridization probe. FIG. 9B shows a line diagram representing the structure of an example dual inversion probe. The locations of 3'-3' and 5'-5' inversion linkages are indicated in the diagrams. Arrows indicate orientation of the backbones in the 5' to 3' direction, and highlight the relationship between the orientations of the arm structures and target-complementary sequences in the different probe species. Detectable labels are omitted from the diagrams.

FIGS. 11A–11D show results for pan-bacterial, pan-fungal, Enterobacteriaceae and Gram positive probes, respectively.

DETAILED DESCRIPTION OF THE INVENTION

The present invention embraces hybridization probes having stem-loop structures, wherein the loop portions of the probes can interact with a complementary target, but wherein the individual arm components of the stems are rendered unable to interact with the target. This was accomplished by including in the structure of the probe at least one inversion linkage. Reflecting this feature, probes of the invention are referred to collectively as "inversion probes." Probes that include one inversion linkage are particularly referred to as "parallel-stem hybridization probes." Probes that include two inversion linkages are particularly referred to as "dual inversion probes."

Figure 9A:
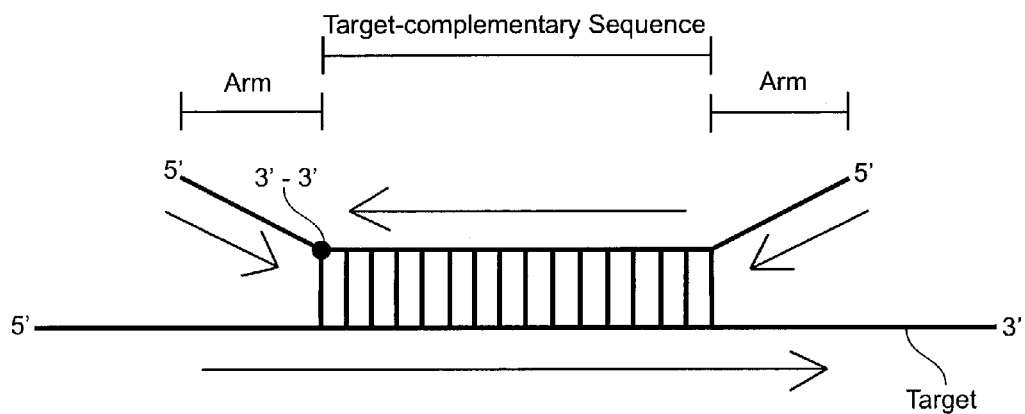
FIGS. 9A–9B schematically illustrate structural differences between parallel-stem hybridization probes and dual inversion probes.
Figure 9B:
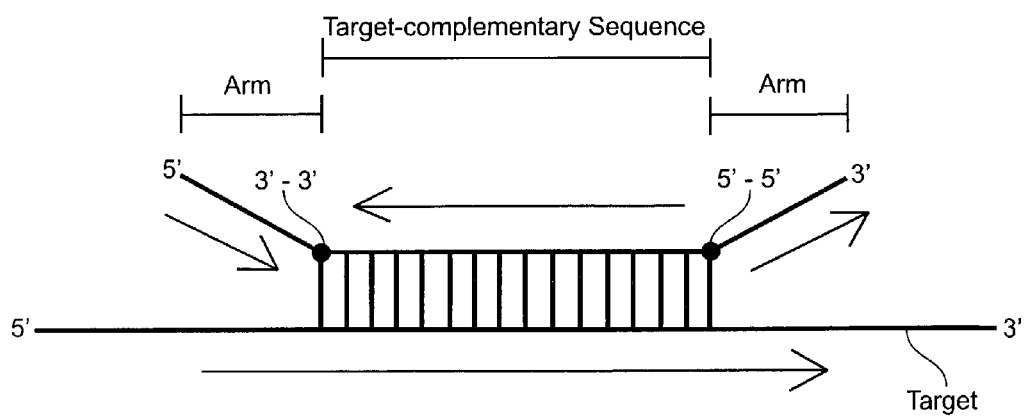

The different types of inversion probe species, meaning parallel-stem hybridization probes and dual inversion probes, share structural and functional features in common with each other. Structurally, both inversion probe species have stem-and-loop configurations where the polarity of the backbone of at least one arm that participates in stem formation is opposite the polarity of the target-complementary sequence of bases which comprise the loop portions of the probes. Parallel-stem hybridization probes have one arm with a polarity opposite the polarity of the target-complementary sequence of bases (illustrated in FIG. 9A). Both of the arms of a dual inversion probe have the same polarity in the primary structure of the molecule, and that polarity is opposite the polarity of the target-complementary sequence of bases (illustrated in FIG. 9B). Functionally, each of the two inversion probe species possesses at least one arm that can participate in stem formation but cannot interact with the target that hybridizes to the target-complementary sequence of bases contained within the probe. This is because at least one of the arms of the different probe species has a polarity that is the same as the target that is hybridized by the loop structure of the probe, and because parallel-stranded structures do not substantially form between the arm sequences and target polynucleotides in the absence of base analogs, or tracts of poly-A and tracts of poly-T, that promote parallel-stranded duplex formation.

As detailed herein, the inversion arm of a parallel-stem hybridization probe is prevented from interacting with target sequences because the polarities of the arms and the target are the same when the probe and the target are hybridized to each other. The extension arm of the parallel-stem hybridization probe can similarly be prevented from interacting with the target by including therein a sequence of base analogs that promote parallel-strand duplex formation while inhibiting antiparallel-strand duplex formation. Since both arms of the dual inversion probe have polarities that are the same as the target when the probe and target are hybridized to each other, neither arm is able to hybridize target sequences.

Dual inversion probes contain inversion linkages at the junction between the first arm and the first boundary of the target-complementary loop, and at the junction between the second arm and the second boundary of the target-complementary loop. This arrangement means that the backbones of the two arms have the same polarities along the length of the primary structure of the probe, and that this polarity is opposite the polarity of the backbone of the target-complementary loop. Thus, in the closed state the two arms of the dual inversion probe are base-paired in an antiparallel configuration. When a dual inversion probe hybridizes to its complementary target, the arms are prevented from interacting with the target because the backbones of the target and the two arms have a parallel relationship to each other.

Inversion probes in accordance with the invention generally include a loop region corresponding to a target-complementary sequence of bases joined to a backbone. This loop is bounded on one end by a first arm which includes a first arm sequence of bases joined to a backbone, and which is joined to the target-complementary sequence of bases through a first arm linkage. The loop is bounded on its second end by a second arm which includes a second arm sequence of bases joined to a backbone, and which is joined to the target-complementary sequence of bases through a second arm linkage. Optionally included is a pair of interactive labels. In a preferred embodiment, a first label is joined to the first arm and a second label is joined to the second arm. In the absence of a target polynucleotide complementary to the loop portion of the probe, the two arms of the probe interact with each other to form a stem duplex. If only one of the two specified linkages joining the arms to the loop region of the inversion probe is an inversion linkage, then the probe is a "parallel-stem hybridization probe." Alternatively, if both of the specified linkages joining the arms to the loop region of the inversion probe are inversion linkages, then the probe is a "dual inversion probe."

Rather than interacting in an antiparallel fashion, arms of the parallel-stem hybridization probe interact in a parallel fashion. As a consequence of this structural arrangement, interactions between at least one arm of the stem (referred to herein as the "inversion arm") and the polynucleotide target that is to be detected are substantially prevented. When nucleobase analogs that preferentially form base pairs in a parallel orientation are included in the other arm of the probe (referred to herein as the "extension arm"), then neither of the arms of the probe can substantially interact with target polynucleotide sequences. In the absence of interactions between the polynucleotide target and arms of the unitary probe, the arm portions of the invented probes advantageously behave uniformly in all probe:target interactions. More particularly, the arm portions of a parallel-stem hybridization probe cannot interact with target sequences, and so do not substantially contribute to sequence-dependent stabilization of the probe:target hybrid.

Dual inversion probes necessarily will include two different inversion linkage types, and will have stem structures formed as a result of antiparallel base pairing. For example, a dual inversion probe may include 5'-5' and 3'-3' inversion linkages, or amino-amino ("N—N") and carboxy-carboxy ("C—C") inversion linkages. The linear structure of a resulting probe molecule would have one 5' and one 3' terminus, or one amino and one carboxy terminus. Thus, the backbones of the arm portions of the probe molecule would share the same polarity, with respect to the primary structure of the molecule, but would differ from the polarity of the backbone of the loop portion of the probe.

General Features of Parallel-Stem Hybridization Probes

Parallel-stem probes of the present invention share certain features in common with the unitary hybridization probes described by Tyagi et al., in U.S. Pat. Nos. 5,925,517 and 6,150,097, the disclosures of these U.S. patents having been incorporated by reference herein above.

Like the unitary probes described by Tyagi et al. (now commonly referred to as "molecular beacons"), the parallel-stem probes disclosed herein include a loop region comprising a target-complementary nucleobase sequence and a pair of "arms" flanking the target-complementary sequence. In certain preferred embodiments there is also included a paired set of interactive labels. Under assay conditions in the absence of target, arms of the parallel-stem probe interact to form a "parallel-stem duplex." Hybridization of a parallel-stem probe to a target polynucleotide effects a conformational change that results in loss of the stem duplex structure. In certain preferred embodiments this conformational change is detected as a change in the properties of at least one member of a pair of interactive labels.

As stated above, the arms of a parallel-stem probe are configured to have a parallel relationship. As a consequence, interactions between at least one of the arms of the probe and the nucleic acid target advantageously are substantially precluded when the probe is hybridized to the target. In highly preferred embodiments of the invention, interactions between both of the arms of the parallel-stem probe and the nucleic acid target are substantially precluded.

Target-complementary nucleobase sequences of parallel-stem probes typically are disposed on a chemical "backbone" or scaffold, and will be substantially single-stranded to facilitate efficient interaction with the target. Regardless of whether the target-complementary nucleobase sequence is disposed on a phosphodiester backbone (as found in RNA and DNA), or a backbone characteristic of peptide nucleic acids or "PNAs" (such as described in U.S. Pat. No. 5,539,082, the disclosure of which is hereby incorporated by reference), or other compatible backbones, including 2'-OMe, phosphorothioate and phosphoramidate, the target-complementary nucleobase sequence will have two ends or "boundaries" located opposite each other along the length of the primary sequence of bases which comprise the probe. These boundaries may be designated as 5' and 3' for a conventional phosphodiester backbone, or as amino ("N") and carboxy ("C") for the PNA backbone.

Flanking the two ends of the target-complementary nucleobase sequence is a pair of arms (one arm at either boundary of the target-complementary nucleobase sequence) that reversibly interacts by means of complementary base pairing. Each of the two arms includes a sequence of nucleobases joined to a backbone, such as one of those described in the preceding paragraph. Each of the arms can hybridize to the other to form the stem duplex under detection conditions when the target-complementary nucleobase sequence is not bound to the target. Stem duplexes of the invented probes characteristically have a substantially parallel-stranded structure, so that the probe has two 5' termini or two 3' termini (in the case of a phosphodiester backbone). Alternative probe structures based on a PNA backbone will have two amino or two carboxy termini.

Those having an ordinary level of skill in the art will understand that backbone polarity is conventionally described in terms such as 5' to 3', or 3' to 5', or N to C, or C to N. Those familiar with the chemical synthesis of oligonucleotides and oligonucleotide analogs such as PNAs understand that two backbones of different polarity can be joined to each other-through an inversion linkage. For example, two oligonucleotides may be joined in a tail-to-tail fashion by a 3'-3' inversion linkage to yield a molecule having two 5' ends.

It is highly preferred for the signal-generating label moieties of the invented parallel-stem probes to comprise interactive "pairs." Preferably, these pairs are matched such that at least one label moiety can alter at least one physically measurable characteristic of the other label moiety when the two are in close proximity, but not when they are sufficiently separated. These label moieties typically are linked to the parallel-stem probe such that the proximity of the label moieties to each other is regulated by the status of the interaction of the parallel-stem duplex. For example, one member of each label pair may be linked to a different terminus of the probe structure. In the absence of target, the label moieties are held in close proximity to each other by the interaction of the parallel-stem duplex. This conformation is referred to as the "closed" state.

Guidelines for Creating Stems Having Parallel-Stranded Configuration

A common feature of the three major families of A-, B-, and Z-DNA duplexes is the antiparallel disposition of the constituent strands. However, it has also been shown that nucleic acids can adopt alternative structures such as triple helices and parallel-stranded duplexes. Those having an ordinary level of skill in the art will appreciate that various models have been created to study these unusual structures. A simplified set of guidelines was followed to determine the nucleobase content of the stem portions of the probes in order to illustrate the construction and use of parallel-stem probes in accordance with the present invention.

The four conventional nucleobases found in DNA are differentially able to participate in parallel-stranded duplex formation. Adenine (A) and thymine (T) moieties in oligomers can pair in either the antiparallel or parallel orientations (van de Sande et al., *Science* 241:551 (1988)). Conversely, the presence of guanine (G) and cytosine (C) can actually destabilize parallel-stranded hybrids (Shchyolkina et al., *Biochemistry* 39:10034 (2000)). However, if G is paired with isocytosine (iC), or if C is paired with isoguanine (iG), then oligomers containing G and/or C moieties can form parallel-stranded hybrids (Sugiyama et al., *J. Am. Chem. Soc.* 118:9994 (1996); Seela et al., *Hel. Chim. Acta.* 80:73 (1997); Seela et al., *Nucleic Acids Symp.* Series No. 37:149 (1997)). A description of the synthesis of certain nucleotides that are capable of forming parallel-stranded structures is given in U.S. Pat. No. 6,147,199, the disclosure of which is hereby incorporated by reference.

Novel chemical linkages have also been used in the backbone structures of model polynucleotides to impose parallel-stranded configurations. To study the details of parallel-stranded DNA, hairpin structures incorporating either 3'-3' or 5'-5' linkages that reverse strand polarity have been employed (van de Sande et al., *Science* 241:551(1988); Germann et al., *Biochemistry* 37:12962 (1998)). Although these hairpin structures did not include label moieties and were not used for promoting intermolecular base pairing, the utility of the 5'-5' and 3'-3' linkages for supporting parallel-stranded configurations in model polynucleotide structures is accepted. In accordance with the present invention, reversed sequence polarity consisting of amino-amino (N-N) and carboxy-carboxy (C-C) linkages are particularly contemplated for PNAs.

Studies of parallel-stranded DNA having mixed AT/GC composition have emphasized the differences between parallel-stranded and antiparallel-stranded double helical forms of DNA. More specifically, parallel-stranded DNA exhibited more pronounced sequence-dependent variations in local helical stability. The overall stability of parallel-stranded DNA formed of A:T and G:C base pairs may depend dramatically on the precise nucleotide sequence, as opposed to antiparallel-stranded B-DNA for which the sequence dependence is less pronounced. As indicated above, the presence of G:C base pairs interspersed among A:T base pairs has been shown to destabilize the parallel-stranded DNA configuration.

Conversely, the presence of certain nucleotide analogs has been shown to favor adoption of the parallel-stranded structure. For example, Seela et al., (*Nucleosides & Nucleotides* 17:2045 (1998)) have disclosed that special sequence designs and a high dA:dT content are required to form parallel-stranded DNA duplex structures. However, the presence of iG:C and/or iC:G base pairs can be sufficient to dictate parallel-stranded polarity. Parallel-stranded duplexes can also be formed using other modified bases, including 7-deazaisoguanine when paired with cytosine, 8-aza-7-deazaisoguanine when paired with cytosine, and 5-aza-7-deazaguanine when paired with guanine. It has been particularly shown that the $iG_d$:dC base pair in parallel-strand hybrids is more stable than the dG:dC pair in antiparallel stranded duplexes, and that this higher stability can dictate chain orientation when additional dA:dT base pairs are present (Seela et al., *Nucleosides & Nucleotides* 18:1543 (1999)).

To illustrate the invention, parallel-stem hybridization probes incorporated 3'-3' or 5'-5' linkages to reverse polarity, and further included the substitution of nucleobase analogs to replace G:C and C:G base pairs which destabilize parallel-stranded structures. Parallel-stranded DNA forms when the guanine-cytosine Watson-Crick base pair of antiparallel-stranded DNA is replaced by the isoguanine-cytosine pair and/or isocytosine- or 5-methylisocytosine-guanine pairs (Seela et al., *Bioorg. & Medicinal Chem. Letters* 10:289 (2000)). Other nucleobase analogs that can promote parallel-stranded helix formation are contemplated for use in connection with the present invention. Thus, parallel-stem probes are not limited by the particular nucleobases that comprise the parallel-stem duplex. Indeed, any nucleobases which participate in, or which favor, parallel-stranded duplex formation may be used to create labeled parallel-stem hybridization probes.

Functional Aspects of Inversion Probes

When the target-complementary nucleobase sequence of an inversion probe, meaning a parallel-stem hybridization probe or a dual inversion probe, hybridizes to its polynucleotide target, a conformational change occurs whereby the two arms of the probe, and any interactive labels attached thereto, become separated. This conformation is referred to as the "open" state. Separation is driven by the thermodynamics of the formation of a helical duplex between the target-complementary nucleobase sequence of the probe and the target. If the inversion probe includes a pair of interactive labels, then open state formation will generate a detectable signal because the separation of the arms alters the interaction of the label moieties. As a consequence, a difference in at least one characteristic of at least one label moiety linked to the inversion probe can be measured. Like conventional molecular beacons, the probes of this invention do not shift to the open conformation when non-specifically bound.

As indicated above, parallel-stem hybridization probes and dual inversion probes have a closed conformation and an open conformation. Interactive label moieties linked to the arms of the inversion probe are more separated in the open conformation than in the closed conformation, and this difference is sufficient to produce a detectable change in at least one measurable characteristic. In the closed conformation the label moieties are sufficiently close that they interact with each other. When this is the case, the measurable characteristic differs in detectable amount, quality, or level, from the open conformation when they do not so interact.

Preferred interactive label moieties are a fluorophore/quencher pair, preferably covalently linked to the inversion probe, most preferably to arm portions of the probes. Highly preferred parallel-stem probes generate a positive fluorescent signal of a particular wavelength when bound to a target polynucleotide in the open state and stimulated with an appropriate light source.

The invention further includes assay methods which utilize at least one interactively labeled inversion probe. These assays may be used for detecting and/or quantifying targets that are single-stranded or double-stranded. Homogeneous assays using interactively labeled inversion probes are highly preferred. Typical assays according to this invention include steps for adding at least one inversion probe, which may be a parallel-stem hybridization probe or a dual inversion probe, to a sample suspected of containing polynucleotide strands that include a target sequence, and determining whether there is a change in the probe's measurable characteristic as compared to that characteristic under the same conditions in the absence of target sequence. The assays may be qualitative or quantitative.

Structural Features of Parallel-Stem Hybridization Probes

Figure 1:
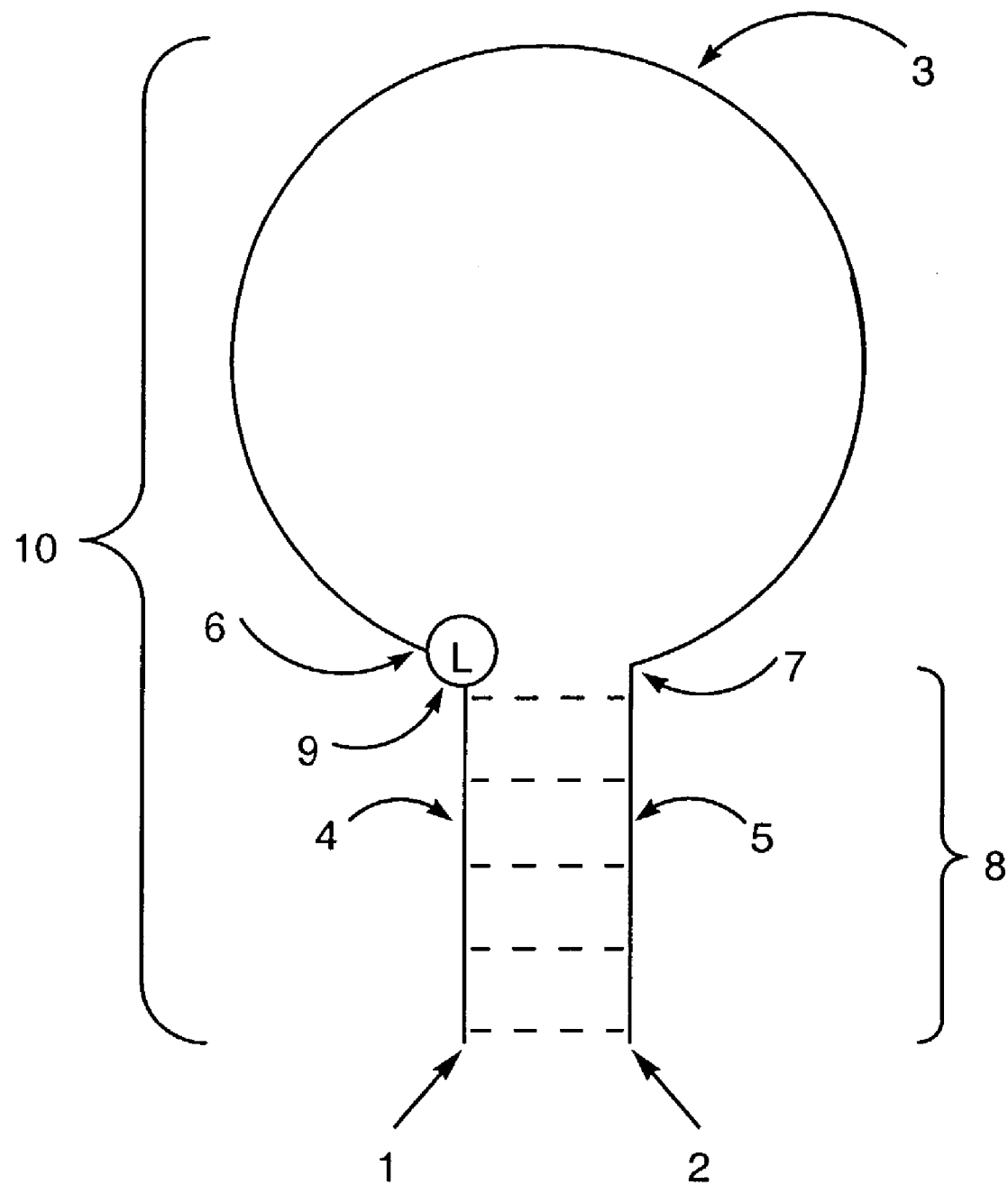
FIG. 1 is a schematic illustration showing the general structure of a parallel-stem hybridization probe.

Parallel-stem probes can be made from DNA, RNA, PNA or other nucleotide analog, or some combination of these. The probes may particularly include modified nucleotides or nucleotide analogs in the target-complementary nucleobase sequence or in the arm portions of the probe. FIG. 1 schematically illustrates the structure of a parallel-stem probe as it exists in the closed conformation. Referring to the figure, parallel-stem hybridization probe 10 includes a target-complementary loop 3, an inversion arm 4 and an extension arm 5 linked to and extending from target-complementary loop 3 to end at the probe termini, identified as a first terminus 1 and a second terminus 2, respectively, in the figure. Target-complementary loop 3 can be defined as extending from a first boundary 6 to a second boundary 7. Although not shown in FIG. 1, it is contemplated that additional nucleobases having antiparallel complementarity may be interposed between the first and second boundaries 6 and 7 of target-complementary loop 3 and the parallel-stranded duplex 8, and further, that those additional nucleobases may participate in target binding. In the absence of a target polynucleotide, the inversion arm 4 and extension arm 5 of the parallel-stem probe are held together through complementary nucleobase pairing (illustrated by dashed horizontal lines between the two arms) to form parallel-stranded stem duplex 8. An inversion linkage 9 in the backbone structure of the probe at a position between inversion arm 4 of parallel-stranded stem duplex 8 and the adjacent boundary 6 of target-complementary loop 3 ensures that inversion arm 4 and extension arm 5 will have backbones disposed in a parallel configuration. Thus, if inversion linkage 9 is a 5'-5' linkage, then terminus 1 and terminus 2 will be 3' termini. Alternatively, if inversion linkage 9 is a 3'-3' linkage, then terminus 1 and terminus 2 will be 5' termini. Analogous linkages for PNA backbones also can result in two carboxy or two amino termini. In certain preferred embodiments of the invention, parallel-stem probe 10 additionally includes a detectable label (not shown in FIG. 1). In highly preferred embodiments one member of an interactive label pair may be linked to the parallel stem probe at or within several nucleobases of terminus 1, and the second member of the interactive label pair may be linked to the parallel stem probe at or within several nucleobases of terminus 2. Preferably, each label is linked to the parallel-stem hybridization probe at or within 8, more preferably at or within 5 nucleobases distant from the probe termini.

Formation of a probe:target hybrid by interaction of target-complementary loop 3 and its target (not shown in FIG. 1) is thermodynamically favored under assay conditions at the detection temperature, and this interaction drives the separation of inversion arm 4 and extension arm 5, thereby resulting in dissolution of parallel-stranded stem duplex 8 and the maintenance of an open conformation. Indeed, inversion arm 4 and extension arm 5 reversibly interact through complementary nucleobase pairing sufficiently strongly to maintain parallel-stranded stem duplex 8 in the closed state under detection conditions in the absence of target sequence, but sufficiently weakly that the hybridization of the target-complementary loop 3 and its target sequence is thermodynamically favored over the intramolecular interaction of arms 4 and 5. This balance allows the parallel-stem probe to undergo a conformational change from the closed state to the open state upon target binding. Non-specific binding of the parallel-stem probe does not overcome the association of inversion arm 4 and extension arm 5 in this manner, thereby facilitating low background signals from interactions of non-complementary target sequences with the target-complementary loop 3.

Figure 2:
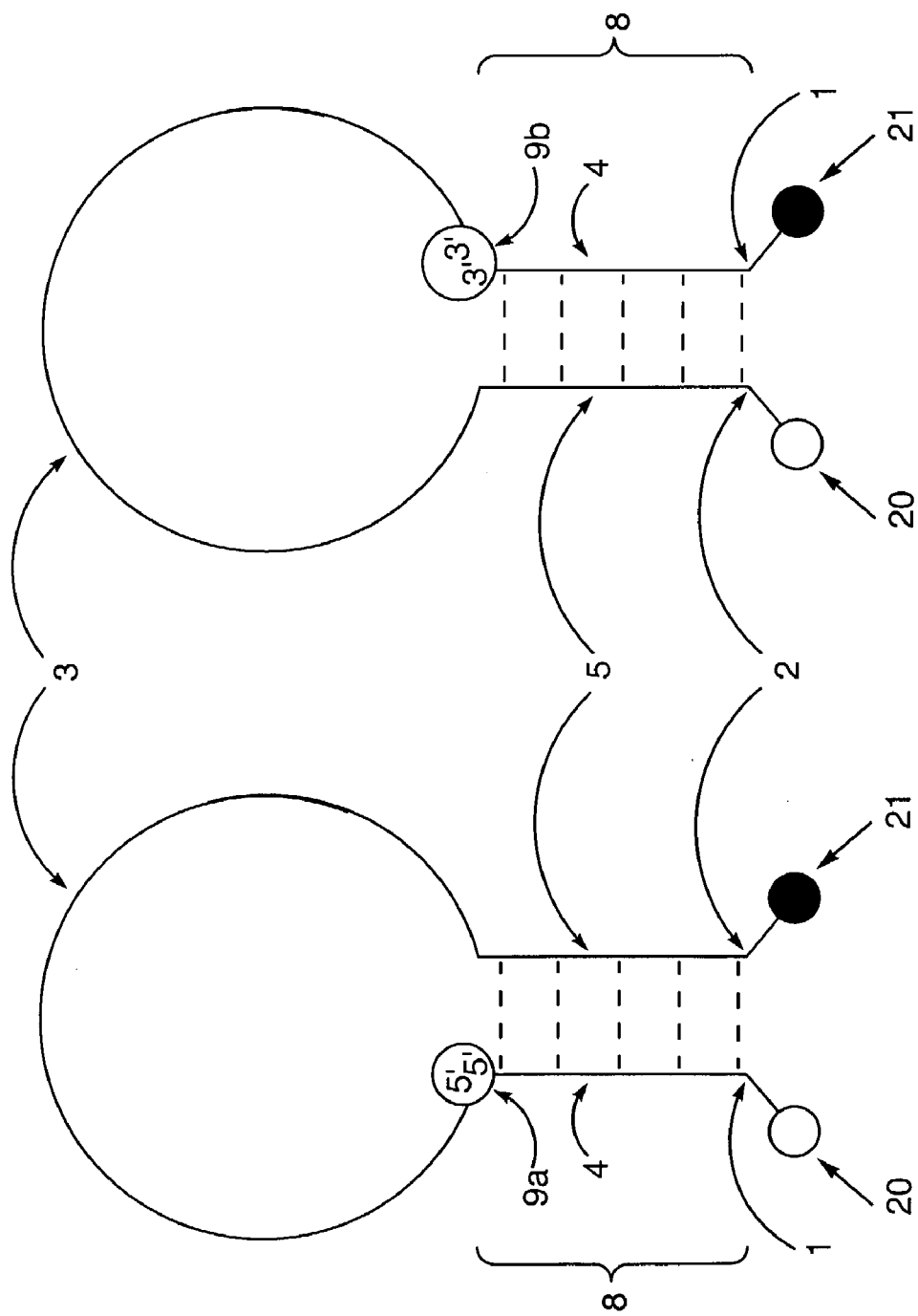
FIG. 2 is a schematic illustration showing two embodiments of the parallel-stem hybridization probe. The structure shown on the left is a parallel-stem hybridization probe that incorporates a 5—'5' inversion linkage. The structure shown on the right is a parallel-stem hybridization probe that incorporates a 3'-3' inversion linkage.

Referring now to FIG. 2, two related embodiments of the invented parallel-stem probe are illustrated in the closed conformation. Each of the probes shown in the figure has a phosphodiester backbone and includes a target-complementary loop 3, an inversion linkage, and a parallel-stranded stem duplex 8 formed by the interaction (illustrated by dashed horizontal lines between the two arms) of inversion arm 4 and extension arm 5. A first label moiety 20 which is a member of an interactive label pair is shown in this embodiment as being disposed at terminus 1 of inversion arm 4. A second label moiety 21 which is a member of the interactive label pair is shown in this embodiment as being disposed at terminus 2 of extension arm 5. The parallel-stem probe in the left portion of the figure has a 5'-5' inversion linkage 9a, and so termini 1 and 2 of this parallel-stem probe are 3' termini. The parallel-stem probe in the right portion of the figure has a 3'-3' inversion linkage 9b, and so termini 1 and 2 of this parallel-stranded probe are 5' termini. Label moieties 20 and 21 are positioned in the structure of parallel-stranded stem duplex 8 such that their proximity is altered by the interaction of arms 4 and 5. Label moieties 20 and 21 could be linked elsewhere to arms 4 and 5 or to the sequence of target-complementary loop 3 near its linkage with parallel-stem duplex 8, that is, close to arms 4 and 5. Some label moieties will interact to a detectably different degree when linked internally along the arms. This is because they will be differentially affected by unraveling of the termini or "breathing" of the stem duplex, or by interactions with the internal rather than the terminal bases.

There is no requirement for a one-to-one molecular correspondence between members of a label pair, especially where one member can affect, or be affected by, more than one molecule of the other member. For example, there can be two quenchers and a single fluorophore, or alternatively two fluorophores and a single quencher. Certain preferred label moieties suitable for use in parallel-stem probes of this invention interact so that at least one moiety can alter at least one physically measurable characteristic of another label moiety in a proximity-dependent manner. The characteristic signal of the label pair is detectably different depending on whether the probe is in the open conformation or the closed conformation.

Structural Features of Dual Inversion Hybridization Probes

Figure 10:
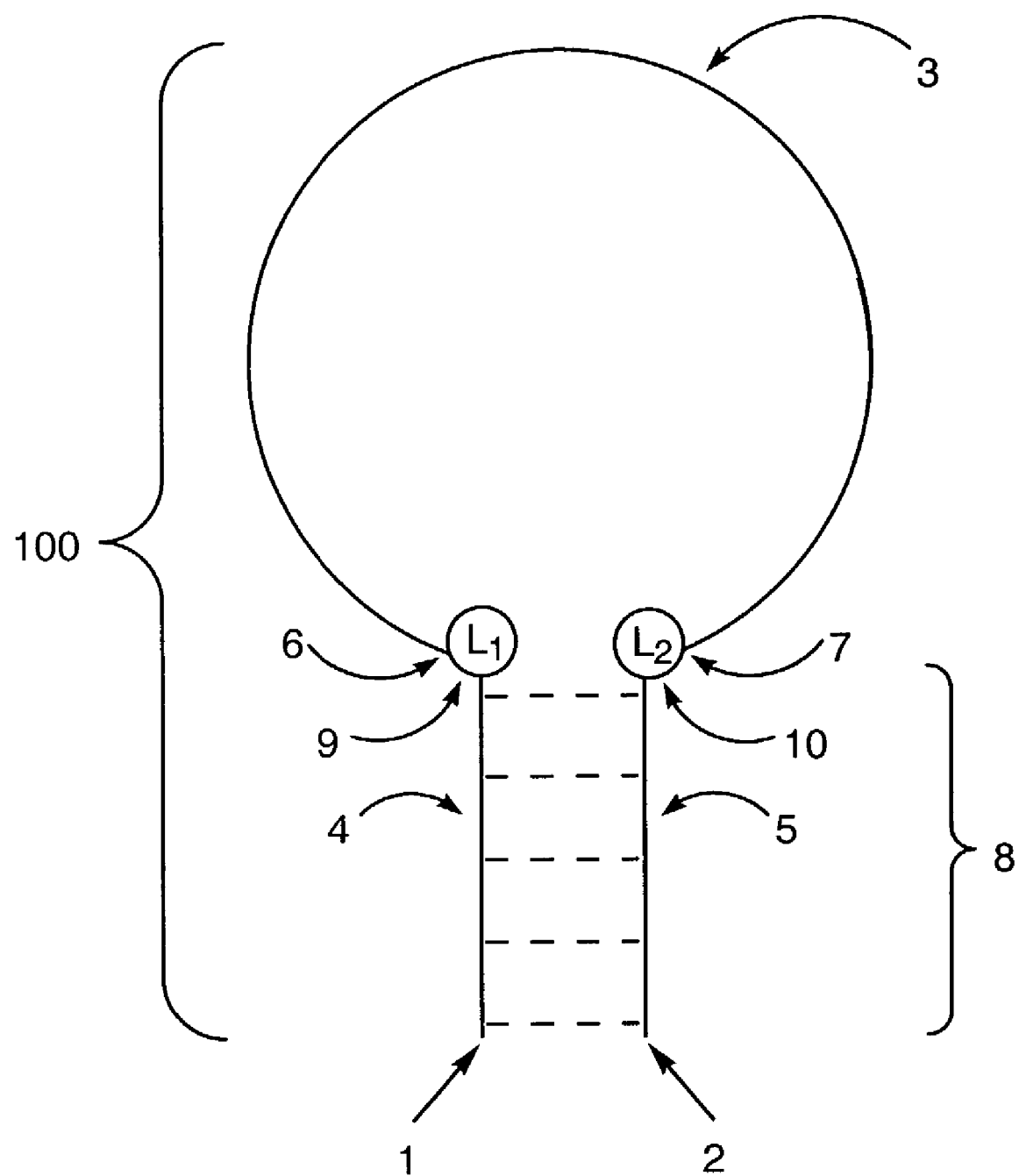
FIG. 10 is a schematic illustration showing the general structure of a dual inversion probe.
Figure 11A:
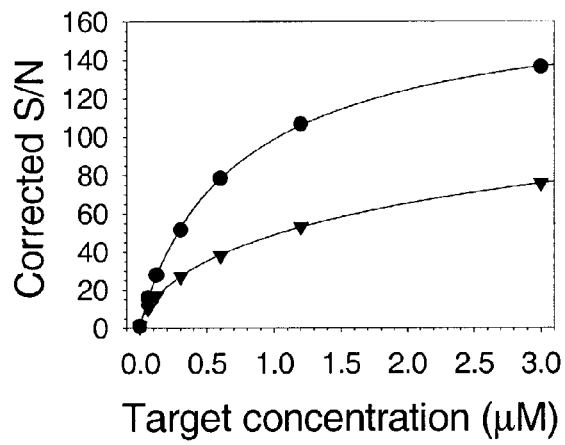
FIGS. 11A–11D are line graphs showing background-subtracted S/N ratios as a function of target concentration for molecular beacons (●) and corresponding dual inversion probes (▼).
Figure 11B:
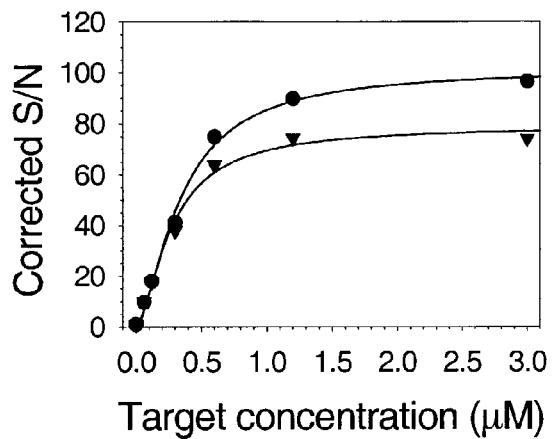
Figure 11C:
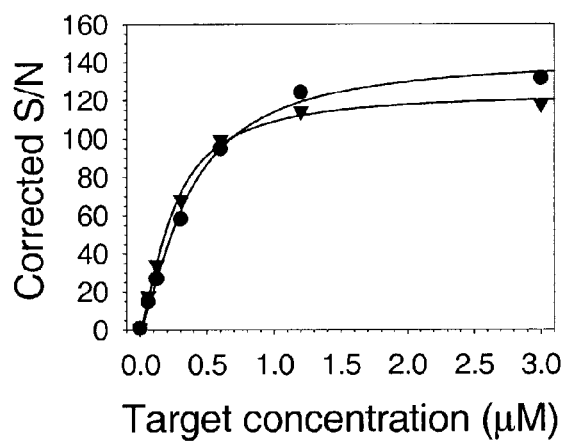
Figure 11D:
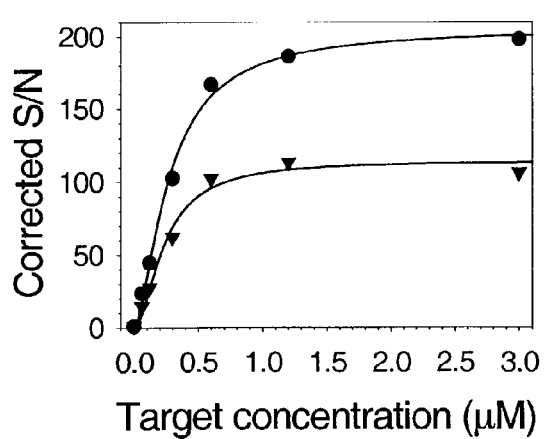

Dual inversion probes can be made from DNA, RNA, PNA or other nucleotide analogs, or some combination of these. The probes may particularly include modified nucleotides or nucleotide analogs in the target-complementary nucleobase sequence or in the arm portions of the probe. FIG. 10 schematically illustrates the structure of a dual inversion probe as it exists in the closed conformation. Referring to the figure, dual inversion probe 100 includes a target-complementary loop 3, a first arm 4 and a second arm 5, each being linked to and extending from target-complementary loop 3 to end at the probe termini, identified as a first terminus 1 and a second terminus 2, respectively, in the figure. Target-complementary loop 3 can be defined as extending from a first boundary 6 to a second boundary 7. Although not shown in FIG. 10, it is contemplated that additional nucleobases having antiparallel complementarity may be interposed between the first and second boundaries 6 and 7 of target-complementary loop 3 and the antiparallel stem duplex 8, and further, that those additional nucleobases may participate in target binding. In the absence of a target polynucleotide, the first arm 4 and second arm 5 of the dual inversion probe are held together through complementary nucleobase pairing (illustrated by dashed horizontal lines between the two arms) to form an antiparallel stem duplex 8. A first inversion linkage 9 in the backbone structure of the probe at a position between first arm 4 and the first boundary 6 of target-complementary loop 3, in combination with a second inversion linkage 10 in the backbone structure of the probe at a position between second arm 5 and the second boundary 7 of target-complementary loop 3, ensures that first arm 4 and second arm 5 will have backbones disposed in an antiparallel configuration in antiparallel stem duplex 8. Thus, if inversion linkage 9 is a 5'-5' linkage, and if second linkage 10 is a 3'-3' inversion linkage, then terminus 1 will be a 3' terminus and terminus 2 will be a 5' terminus. Alternatively, if first linkage 9 is a 3'-3' linkage, and if second linkage 10 is a 5'-5' inversion linkage, then terminus 1 will be a 5' terminus and terminus 2 will be a 3' terminus.

Analogous linkages for PNA backbones also can result in antiparallel stem duplex 8 having one amino terminus and one carboxy terminus. In certain preferred embodiments of the invention, dual inversion probe 100 additionally includes a detectable label (not shown in FIG. 10). In highly preferred embodiments one member of an interactive label pair may be linked to the dual inversion probe at or within several nucleobases of terminus 1, and the second member of the interactive label pair may be linked to the dual inversion probe at or within several nucleobases of terminus 2. Preferably, each label is linked to the dual inversion probe at or within 8, more preferably at or within 5 nucleobases distant from the probe termini.

Again, there is no requirement for a one-to-one molecular correspondence between members of a label pair, especially where one member can affect, or be affected by, more than one molecule of the other member. Certain preferred label moieties suitable for use in dual inversion probes of this invention interact so that at least one moiety can alter at least one physically measurable characteristic of another label moiety in a proximity-dependent manner. The characteristic signal of the label pair is detectably different depending on whether the probe is in the open conformation or the closed conformation.

Formation of a probe:target hybrid by interaction of target-complementary loop 3 and its target (not shown in FIG. 10) is thermodynamically favored under assay conditions at the detection temperature, and this interaction drives the separation of first arm 4 and second arm 5, thereby resulting in dissolution of antiparallel stem duplex 8 and the maintenance of an open conformation. Indeed, first arm 4 and second arm 5 reversibly interact through complementary nucleobase pairing sufficiently strongly to maintain antiparallel stem duplex 8 in the closed state under detection conditions in the absence of target sequence, but sufficiently weakly that the hybridization of the target-complementary loop 3 and its target sequence is thermodynamically favored over the intramolecular interaction of arms 4 and 5. This balance allows the dual inversion probe to undergo a conformational change from the closed state to the open state upon target binding. Non-specific binding of the dual inversion probe does not overcome the association of first arm 4 and second arm 5 in this manner, thereby facilitating low background signals from interactions of non-complementary target sequences with the target-complementary loop 3.

Importantly, the orientation of the target-complementary loop sequence of a dual inversion probe will determine the identity of the inversion linkages in the probe structure. If the target-binding sequence of the probe has a 5'-end and a 3'-end, then that 5'-end will always be adjacent to a 5'-5' inversion linkage and the 3'-end will always be adjacent to a 3'-3' inversion linkage. Thus, with reference to FIG. 10, if target-complementary loop 3 is oriented so that first boundary 6 corresponds to the 5'-end and second boundary 7 corresponds to the 3'-end of the target-binding portion of the probe, then first inversion linkage 9 must be a 5'-5' inversion linkage, and second inversion linkage 10 must be a 3'-3' inversion linkage.

Preferred Label Moieties for Inversion Probes

As indicated above, inversion probes preferably include at least one detectable label. Preferred label moieties for inversion probes are either singly detectable labels or individual members of a pair of interactive labels.

Examples of singly detectable labels that are preferred for use in connection with the invention include radioisotopes, enzymes (i.e., alkaline phosphatase or horseradish peroxidase), fluorophores, chromophores and label moieties for the generation of light through radioluminescent, bioluminescent, chemiluminescent or electrochemiluminescent reactions. These label moieties may be positioned anywhere in the probe or may be linked to the probe at any location, as long as probe function, particularly hybridization to target, is not substantially compromised. Particular examples of detectable labels that would be useful for labeling inversion probes include a $^{32}$P radioisotope, and a chemiluminescent acridinium ester of the type disclosed by Arnold et al., in U.S. Pat. No. 5,283,174 for use in conjunction with homogeneous protection assays, and of the type disclosed by Woodhead et al., in U.S. Pat. No. 5,656,207 for use in connection with assays that quantify multiple targets in a single reaction. The disclosures contained in these patent documents are hereby incorporated by reference. Both radiolabels and acridinium ester labels can be joined to an inversion probe in either the loop region or stem region of the probe.

Examples of detectable labels that are preferred as members of an interactive pair of labels interact with each other by FRET or non-FRET energy transfer mechanisms. Fluorescence resonance energy transfer (FRET) involves the radiationless transmission of energy quanta from the site of absorption to the site of its utilization in the molecule, or system of molecules, by resonance interaction between chromophores, over distances considerably greater than interatomic distances, without conversion to thermal energy, and without the donor and acceptor coming into kinetic collision. The "donor" is the moiety that initially absorbs the energy, and the "acceptor" is the moiety to which the energy is subsequently transferred. In addition to FRET, there are at least three other "non-FRET" energy transfer processes by which excitation energy can be transferred from a donor to an acceptor molecule. First, "reabsorption" or "trivial reabsorption" is the process in which a photon is emitted by the donor and is subsequently absorbed by the acceptor. Second, "complex formation" refers to the creation of an excited-state complex of a donor and an acceptor that are in very close proximity, essentially in molecular contact with each other. Third, "collisional quenching" can occur when an excited molecule loses its excitation energy to another molecule as a result of colliding with that other molecule. Various aspects of these energy transfer processes have been discussed in *Resonance Energy Transfer: Theory and Data*, B. W. van der Meer, G. Coker III, S.-Y. S. Chen, VCH Publishers, NY (1994).

As stated above, certain preferred labels are chosen such that energy transfer is the mode of interaction between the labels. In such cases, the measurable physical characteristics of the labels could, among other modes, be a decrease in the lifetime of the excited state of one label, a complete or partial quenching of the fluorescence of one label, an enhancement of the fluorescence of one label or a depolarization of the fluorescence of one label. The labels may be excited with a narrow wavelength band of radiation or a wide wavelength band of radiation. Similarly, the emitted radiation may be monitored in a narrow or a wide range of wavelengths, either with the aid of an instrument or by direct visual observation.

When two labels are held sufficiently close that energy emitted by one label can be received or absorbed by the second label, whether by a FRET or non-FRET mechanism, the two labels are said to be in "energy transfer relationship" with each other. This is the case, for example, when an invented hybridization probe is maintained in the closed state by formation of a stem duplex, and fluorescent emission from a fluorophore attached to one arm of the probe is quenched by a quencher moiety on the opposite arm.

Highly preferred label moieties for inversion probes include a fluorophore and a second moiety having fluorescence quenching properties (i.e., a "quencher"). In this embodiment, the characteristic signal is likely fluorescence of a particular wavelength, but alternatively could be a visible light signal. When fluorescence is involved, changes in emission are preferably due to FRET, or to radiative energy transfer or non-FRET modes. When an inversion probe having a pair of interactive labels in the closed state is stimulated by an appropriate frequency of light, a fluorescent signal is generated at a first level, which may be very low. When this same probe is in the open state and is stimulated by an appropriate frequency of light, the fluorophore and the quencher moieties are sufficiently separated from each other that energy transfer between them is substantially precluded. Under that condition, the quencher moiety is unable to quench the fluorescence from the fluorophore moiety. If the fluorophore is stimulated by light energy of an appropriate wavelength, a fluorescent signal of a second level, higher than the first level, will be generated. The difference between the two levels of fluorescence is detectable and measurable. Using fluorophore and quencher moieties in this manner, the inversion probe is only "on" in the "open" conformation and indicates that the probe is bound to the target by emanating an easily detectable signal. The conformational state of the probe alters the signal generated from the probe by regulating the interaction between the label moieties.

Examples of donor/acceptor label pairs that may be used in connection with the invention, making no attempt to distinguish FRET from non-FRET pairs, include fluorescein/tetramethylrhodamine, IAEDANS/fluororescein, EDANS/DABCYL, coumarin/DABCYL, fluorescein/fluorescein, BODIPY FRBODIPY FL, fluorescein/DABCYL, lucifer yellow/DABCYL, BODIPY/DABCYL, eosine/DABCYL, erythrosine/DABCYL, tetramethylrhodamine/DABCYL, Texas Red/DABCYL, Cy5/BH1 and fluorescein/QSY7 dye. Those having an ordinary level of skill in the art will understand that when donor and acceptor dyes are different, energy transfer can be detected by the appearance of sensitized fluorescence of the acceptor or by quenching of donor fluorescence. When the donor and acceptor species are the same, energy can be detected by the resulting fluorescence depolarization. Non-fluorescent acceptors such as DABCYL and the QSY 7 dyes advantageously eliminate the potential problem of background fluorescence resulting from direct (i.e., non-sensitized) acceptor excitation. Preferred fluorophore moieties that can be used as one member of a donor-acceptor pair include fluorescein. Highly preferred quencher moieties that can be used as another member of a donor-acceptor pair include 4-[4-(dimethylamino) phenylazo]benzoic acid (DABCYL).

Target-Complementary Loop Structures

Lengths of the target-complementary loops and arm sequences of inversion probes are chosen to allow proper thermodynamic functioning under the conditions of the projected hybridization assay. The length of a target-complementary sequence of bases which comprise the loop can range from 7 to about 140 nucleobases, preferably from 10 nucleobases to about 140 nucleobases, still more preferably from 10 nucleobases to 25 nucleobases, still more preferably 16 nucleobases to 22 nucleobases, and yet still more preferably from 8 nucleobases to 25 nucleobases.

Structure and Function of the Arm Portions of Inversion Probes

The sequences of the arm elements of the invented probes should be of sufficient length that under conditions of the assay, including the detection temperature, the arms are associated with each other so that any interactive label moieties joined thereto are kept in close proximity to each other when the probes are not bound to a target. Depending upon the assay conditions, arm lengths in the range of 3–25 nucleobases can perform this function. An intermediate range of 4–15, more preferably 5–12, and still more preferably 6–8 nucleobases also can be appropriate. The actual length will be chosen with reference to the target-complementary sequence such that the probe remains in the closed conformation in the absence of target and assumes an open conformation when bound to target.

The upper limit of the length of the arms is governed by two criteria related to the thermodynamics of probes according to the invention. First, it is preferred that the thermal denaturation, or melting temperature (Tm), of the stem duplex, under assay conditions, should be higher than the detection temperature of the assay. "Tm" refers to the temperature at which 50% of the probe is converted from the hybridized to the unhybridized form. Certain preferred stem duplexes have melting temperatures 2–15° C. higher, or more preferably 5–10° C. higher, than the assay temperature. Second, the energy released by the formation of the stem duplex should be less than the energy released by the formation of the hybrid between the target-complementary loop of the probe and the polynucleotide target at the detection temperature of the assay. When this is the case, target-mediated opening of the probe will be thermodynamically favored. Thus, the Tm of the target-complementary loop:target hybrid should be higher than the Tm of the stem duplex.

The Tm of the stem duplex must be above the assay temperature, so that the probe does not open in the absence of the target-complementary loop hybridizing to a target. At the same time, the Tm of the stem duplex must be sufficiently below the Tm of the hybrid of the target-complementary loop with the target sequence to ensure proper probe functioning and appropriate generation of a detectable signal. Certain preferred stem duplexes have Tm 2–15° C., more preferably 5–10° C., above the assay temperature, and at or below the Tm of the hybrid between the target-complementary loop and the target polynucleotide sequence. Inversion probes having target-complementary sequences from 8 to 25 nucleobases in length, combined with arm sequences from 6 to 12 nucleobases in length, may be designed within these parameters.

Those having an ordinary level of skill in the art will realize that these parameters will vary with the conditions of the hybridization assay, and that those conditions must be considered when designing the inversion probes of this invention. The length of the arms and their nucleobase content will affect the Tm of a stem duplex. For a desired Tm, under particular assay conditions, a length and a nucleobase content of the arms may easily be calculated (see Chen et al., *J. Am. Chem. Soc.* 123:1267 (2001)). The Tm of the stem duplex of a probe also can be empirically determined for given assay conditions. Based on the foregoing descriptions of probe function, it should be clear that the thermodynamics of inversion probes having stem duplexes will vary with length and nucleobase composition of the stem, and target-complementary sequence, as well as assay conditions.

When interactive fluorescent donor-acceptor pairs are employed as labels, the fluorophore and quencher moieties preferably are linked anywhere along the arm portions of the probe, subject to certain provisions. The fluorophore and quencher moieties should be proximate to each other in the closed conformation of the probe to give a relatively lower fluorescence signal, yet should be sufficiently separated from each other in the open conformation to give a relatively higher fluorescence signal.

It is also contemplated that multiple labels (i.e., multiple fluorophore and quencher moieties) can be used. Multiple labels, in some cases, permit assays with higher sensitivity. In some instances, when the affinity pair is made up of a pair of oligonucleotide arms, a multiplicity of labels can be achieved by distributing a number of fluorophore moieties on one arm and a corresponding number of quencher moieties on the other arm, such that each fluorophore moiety will be close to a quencher moiety when the stem duplex forms. U.S. Pat. No. 6,037,130, the disclosure of this patent being incorporated by reference herein, describes an alternative mode of labeling that also is contemplated for labeling the probes of the present invention.

The inversion probes described herein may comprise nucleic acid molecules that can be assembled by commonly known methods of solid-phase synthesis, by ligation of synthetic sequences or restriction fragments or by a combination of these techniques. The simplest inversion probes can be assembled by synthesis of a single oligonucleotide comprising arm sequences flanking the target complementary sequence. Labeled nucleotides can be used in oligonucleotide synthesis, for example to introduce a fluorophore moiety and a quencher moiety at oppositely disposed termini of the probe. Alternatively, label moieties can be linked to the termini of the probe after synthesis of the main structure of the nucleobase-containing probe.

Assays Employing Inversion Probes

Preferably, assays for detecting target polynucleotides using the invented probes are conducted in homogeneous formats. These assays may involve direct detection of polynucleotides, or alternatively may involve detection of amplicons produced in an amplification reaction that uses a particular polynucleotide as a template. When amplicons are detected by the parallel-stem probes described herein, the detection may be an end-point detection (i.e., detection of amplicons at the conclusion of the amplification reaction), or alternatively may involve real-time monitoring of amplicon synthesis during the amplification reaction. Exemplary amplification reactions include transcription-based amplification assays (such as TMA and NASBA), the polymerase chain reaction (PCR), self-sustained sequence reaction (3SR), strand-displacement amplification (SDA) reaction, and Q-beta replicase-mediated amplification reactions. When amplicon synthesis is monitored in real-time amplification protocols, the inversion probe will be included in the reaction mixture, and fluorescence will be measured continuously or intermittently during the amplification reaction. Certain embodiments of assays according to the present invention utilize multiple hybridization probes with interactive labels immobilized to a solid surface. Exemplary surfaces include beads or particles, membranes, dipsticks, planar glass or plastic surfaces such as glass or plastic slides or microtiter wells, and glass or plastic optical fibers.

Immobilization of Inversion Probes

Immobilized probes according to the invention advantageously may be used in assays for the simultaneous determination of a predetermined set of target sequences. For example, a series of inversion probes can be prepared, each comprising a different sequence in its target-complementary loop region. Each probe may then be linked to the same support surface, such as those elaborated above, at its own predetermined location through covalent bonds or non-covalent interactions. After contacting the support and the sample under hybridization conditions, the support may be stimulated with light of an appropriate frequency. Fluorescence will occur at those locations where immobilized probes have formed hybrids with target molecules from the sample. Arrays or microarrays of immobilized inversion probes are particularly preferred embodiments of structures or devices incorporating immobilized probes in accordance with the invention. Immobilization of inversion probes by linkage through the target-complementary loop is particularly preferred.

Illustration of the Preferred Embodiment

The utility of parallel-stem hybridization probes was first demonstrated by creating three different probe species, and then testing these probes for interaction with either of two synthetic targets. Variables that were considered when designing these probes included: (1) the desire to promote either parallel or antiparallel orientations of the arm components of putative stem regions, and (2) the presence or absence of modified nucleotides in the arm components of putative stem regions that would facilitate formation of parallel-stranded duplexes and prevent interaction between the arm components and the target. RNA targets used in these procedures had sequences that were contiguously complementary either to the loop region of the probe, or to sequence of the probe over its entire length. In all cases, the sequences of the probes were identical over their lengths, except for the substitution of 5-methyl-iC for cytosine in the stem portions, as indicated.

Oligonucleotides containing inversion linkages were synthesized using standard laboratory procedures. More particularly, to prepare oligonucleotides containing 3'-3' internucleotide linkages, synthesis was first performed in the 5' to 3' direction beginning with 5'-derivatized CPG columns and 5'-phosphoranidites. Subsequent coupling cycles were repeated in the 5' to 3' direction (forming 3'-5' linkages) until the first of the adjacent bidirectional segments was complete. The direction of synthesis was reversed to 3' to 5' by replacing 5'-phosphoramidites with standard 3'-phosphoramidites. The first linkage formed after the reversal of synthesis direction was a 3'-3' internucleotide linkage. Subsequent couplings were repeated in the 3' to 5' direction (forming 5'-3' linkages) until the second of the bidirectional segments was complete. A resulting oligonucleotide containing a single 3'-3' inversion linkage had two 5' ends. An analogous procedure was followed for preparation of 5'-5' linked oligonucleotides, except that synthesis was begun in the 3' to 5' direction from a 3'-derivatized CPG column, using standard 3'-phosphoramidites. After completion of the first segment, the direction of synthesis was reversed to the 5' to 3' direction by switching from 3'- to 5'-phosphoramidites, resulting in the formation of a 5'-5' internucleotide linkage, followed by 3'-5' internucleotide bond formation until the desired sequence was achieved. A resulting oligonucleotide containing a single internal 5'-5' inversion linkage had two 3' ends.

Figure 3:
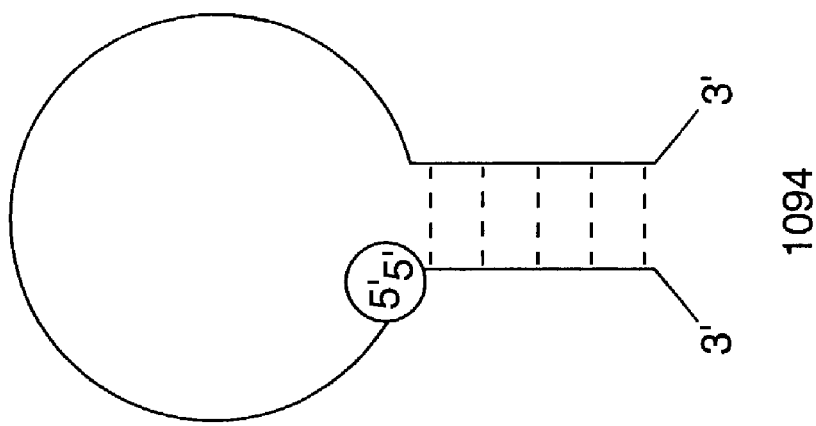
FIG. 3 is a schematic illustration showing the folded structures of three probes in the absence of a complementary target polynucleotide. Label moieties are omitted from the illustration. The 1093 probe is a conventional molecular beacon. The 1034 probe incorporates an inversion linkage but cannot form a stem duplex. The 1094 probe is a parallel-stem hybridization probe.
Figure 3:
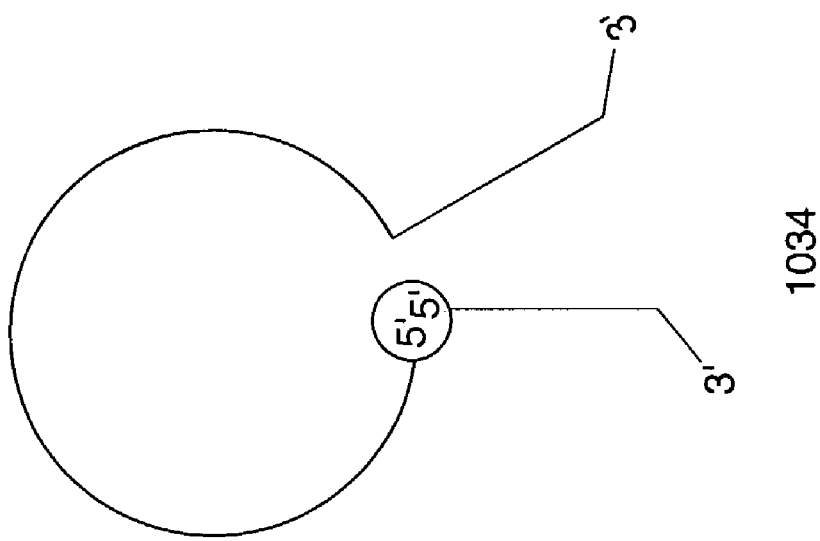
Figure 3:
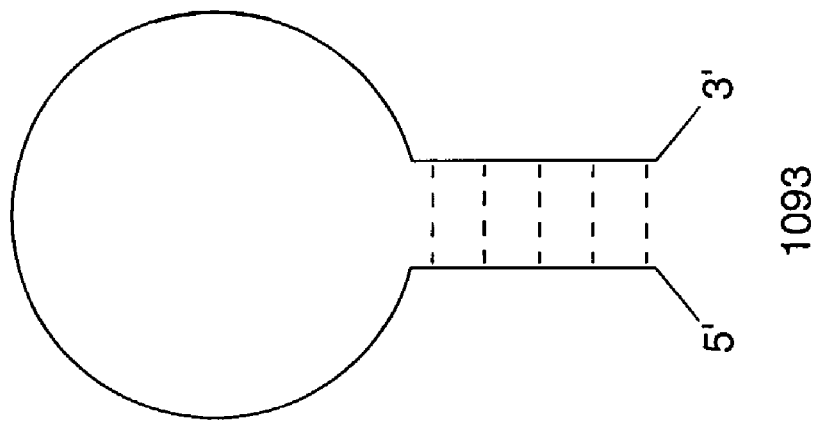

The three probe species used to demonstrate the utility of parallel-stem hybridization probes had the following structures. The first probe, named 1093, had the structure: 5'-DABCYL-GGTGTGGGGUACAGUGCAGGGG CACACC-Fluorescein-3' (SEQ ID NO:1). This probe had the structure of a conventional molecular beacon with an antiparallel stem duplex. The second probe, named 1034, had the structure: 3'-DABCYL-GGTGTG-5'-5'-GGGUACAGUGCAGGGG CACACC-Fluorescein-3' (SEQ ID NO:2). This probe was designed to have arms that were configured in a parallel orientation, but that could not form a stem duplex because G:C base pairs do not participate in parallel-stranded structures. Thus, the 1034 probe served as a control that included a 5'-5' linkage, but did not form a stem structure that maintained a closed conformation in the absence of a complementary target polynucleotide. The third probe was a parallel-stem hybridization probe. The third probe, named 1094, had the structure: 3'-DABCYL-GGTGTG-5'-5'-GGGUACAGUGCAGGGG iCAiCAiCiC-Fluorescein-3' (SEQ ID NO:3). This probe had arms capable of base pairing in a parallel configuration, and forming duplex structures as the result of the presence of 2'-deoxy-5-methylisocytidine (2-amino-4-oxy-5-methyl-1-β-D-2'-deoxyribofuranosyl-1H-pyrimidine) (iC) residues in one arm of the stem. Thus, the 1094 probe included a 5'-5' linkage and was capable of forming a parallel-stranded stem duplex. The target-complementary sequence of bases in the loop portions of the 1093 and 1094 probes is given by GGGUACAGUGCAGGGG (SEQ ID NO:9). Underlined nucleotides in the probe sequences indicate positions falling outside the target-complementary loop region, but which may participate in stem formation. Underlined positions were deoxyribonucleotides, while the remaining positions of each probe were occupied by 2'-OMe nucleotide analogs. Each of the three probes included a non-nucleotide linker, as described by Arnold et al., in U.S. Pat. No. 5,696,251, located between nucleotides 15 and 16 at a position within the target-complementary sequence. Although initial procedures were carried out in solution, this non-nucleotide linker provided a way to immobilize the probes to a solid surface. Indeed, this approach is highly preferred for immobilizing parallel-stem hybridization probes. FIG. 3 schematically illustrates how the structural differences between the probes were reflected by the folded structures of the molecules in the absence of complementary target polynucleotides.

Two different polynucleotides that were used as targets for hybridizing the above-described probes had the following structures. The first target, named 1059, had the sequence: 5'-UAUUCUUUCCCCUGCACUGUACCCCCCAAUC-3' (SEQ ID NO:4). The 1059 target was contiguously complementary only to the loop sequence of each of the three probes. The second target, named 1061, had the sequence: 5'-UAGGUGUGCCCCUGCACUGUACCCCACACCU-3' (SEQ ID NO:5), and was complementary to the antiparallel probe 1093 over its entire length.

Interactions between the different probes and targets were conveniently assessed in the following Example using Tm measurements. The Tm was measured as an indicator of hybrid stability. When two nucleic acid hybrids have different Tm values, the hybrid having the higher Tm is the more "stable" of the two. By comparing the Tm values for the three probes described above, both alone and hybridized with targets, it was possible to obtain information about the extent to which the stem regions of the self-reporting probes interacted with target sequences.

Example 1 describes the methods used to establish that the arm segments of the model parallel-stem hybridization probe advantageously did not interact with target sequences. Notably, the model target sequence employed in the following procedure was an HIV-1 polynucleotide sequence.

EXAMPLE 1

Quantifying Interactions Between Polynucleotide Targets and Probes

The 1034, 1094 and 1093 probes were independently synthesized by solid-phase phosphite triester chemistry using DABCYL-linked controlled pore glass and 5' fluorescein-labeled phosphoramidite on a Perkin-Elmer (Foster City, Calif.) EXPEDITE model 8909 automated synthesizer. The inversion linkages in the 1034 and 1094 probes, like all of the inversion linkages described herein, were created using a combination of 5'-β-cyanoethyl and 3'-β-cyanoethyl phosphoraiidites that were purchased from Glen Research Corporation (Sterling, Va.), Proligo (Boulder, Colo.) or Pierce Biotechnology (Rockford, Ill.). All of these probes were constructed using 2'-OMe nucleotide analogs in their target-complementary loop regions, and standard deoxyribonucleotides in their stem regions. Following synthesis, the probes were deprotected and cleaved from the solid support matrix and then purified using polyacrylamide gel electrophoresis followed by HPLC according to procedures that will be familiar to those having an ordinary level of skill in the art. The 1059 and 1061 synthetic RNA targets also were prepared using procedures familiar to those having an ordinary level of skill in the art.

Melting curves for samples containing the three probes individually or in combination with one of the two RNA targets were generated to assess probe:target interactions. Each trial was conducted by combining the polynucleotides to be tested (1 µM of probe or 1 µM of probe and 1 µM of target) in TENT buffer (50 mM Tris-HCl (pH 8.0), 50 mM NaCl, 0.1 mM EDTA, 0.2% of the non-ionic wetting agent TWEEN-20 (a registered trademark of ICI Americas, Inc.)), incubating at 60° C. for 30 minutes, and then cooling to room temperature for 15 minutes. The hybridized samples were then loaded into a Beckman DU-640 temperature-controlled U/visible spectrophotometer. Temperatures were increased from 30° C. to 90° C. in 0.5° C./minute increments, with absorbance measurements at 260 nm ($A_{260}$) and 494 nm ($A_{494}$) being recorded every 0.5° C. The first derivative of the curve plotted on a graph of absorbance against temperature was used to identify the inflection point which represented the Tm value. Results of these procedures appear in Table 1.

TABLE 1

Quantifying Probe: Target Interactions

| | Probe Features | Tm at 260 nm (in ° C.) |
|---|---|---|
| Probe | | |
| 1093 | Molecular Beacon | 61.8 |
| 1034 | Linear Probe with Inversion Linkage | not detected |
| 1094 | Parallel-Stem Hybridization Probe | 44.6† |
| Probe/Target | | |
| 1093/1061 | Molecular Beacon | 72.8† |
| 1093/1059 | Molecular Beacon | 52.2† |
| 1034/1061 | Linear Probe with Inversion Linkage | 79.1† |
| 1034/1059 | Linear Probe with Inversion Linkage | 68.9 |
| 1094/1061 | Parallel-Stem Hybridization Probe | 79.6† |
| 1094/1059 | Parallel-Stem Hybridization Probe | 77.8† |

†Value represents the averaged measurements of two trials

Where they could be determined, Tm values calculated from $A_{494}$ measurements generally confirmed trends observed in the Tm values that were calculated from $A_{260}$ measurements. Only results obtained using $A_{260}$ measurements are presented here because these readings could be obtained for all but the 1034 probe by itself. This probe was designed to have a structure that did not include a stable stem region, and did not exhibit a discrete melting transition measurable at the 494 nm absorbance wavelength which monitors energy absorption by the fluorescein fluorophore or at the 260 mn wavelength which monitors energy absorbance by the nucleobases.

Table 1 summarizes the thermal stabilities for the three probes that were used to demonstrate utility of a model parallel-stem hybridization probe. As indicated by the Tm values for the 1094, 1093 and 1034 self-reporting probes listed in the table, there were significant differences between the stabilities of the stem regions for these molecules. For example, the antiparallel stem of the 1093 molecular beacon was more stable (Tm=61.8° C.) than the parallel stem of the 1094 parallel-stem hybridization probe (Tm=44.6° C.). As noted above, it was not possible to determine a Tm value for the 1034 molecule that included a 5'-5' inversion linkage, but that lacked the nucleobase analogs required to facilitate parallel-stem duplex formation. These findings were consistent with the model structures shown in FIG. 3 where the stem regions of only the 1093 and 1094 molecules formed duplex structures. Also, the parallel stem was less stable when compared with a corresponding antiparallel stem having an equivalent length and sequence, but lacking 5-methyl-iC nucleobases. Of course, by extending the length of a parallel stem the Tm would be increased.

Figure 4A:
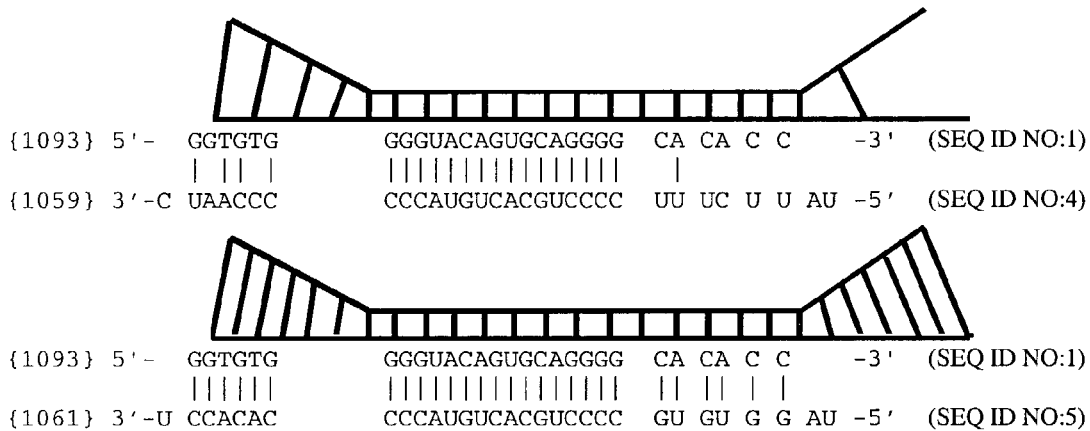
FIGS. 4A–4C schematically illustrate the predicted hybridization results for three probes with each of two different target polynucleotides, and present corresponding sequence alignments. The diagrams in FIG. 4A show predicted results for hybridization of the 1093 molecular beacon with the 1059 and 1061 targets. The diagrams in FIG. 4B show predicted results for hybridization of the 1034 probe with the 1059 and 1061 targets. The diagrams in FIG. 4C show predicted results for hybridization of the 1094 parallel-stem hybridization probe with the 1059 and 1061 targets. Nucleotide sequences for the probes and target polynucleotides are shown below each of the schematic diagrams. Vertical lines in the alignments indicate complementary nucleobase interactions. The schematic diagrams of the 1034 and 1094 probes include the 5'-5' inversion linkage. Sequences of the 1059 and 1061 targets are presented in the 3' to 5' orientation to show complementarity with the probe sequences. Label moieties are omitted from the illustration.

The measured Tm values for hybrids that included the 1093 probe and either of the two model targets provided baseline information about stem interactions with target sequences. The fact that the Tm of the 1093/1059 hybrid (52.2° C.) was lower than the Tm of the 1093/1061 hybrid (72.8° C.) indicated that greater stability was provided by additional base pairing that was possible with the 1061 target. This was because the sequence of the 1093 probe was fully complementary to the sequence of the 1061 target, but had limited complementarity with the sequence of the 1059 target. Importantly, the difference between the referenced Tm values indicated a difference in stabilities that was attributed to differential interaction between the arms of the stem and the targets. This result confirmed that the arm components could positively interact with target polynucleotide sequences that were complementary, as shown in FIG. 4A.

Figure 4B:
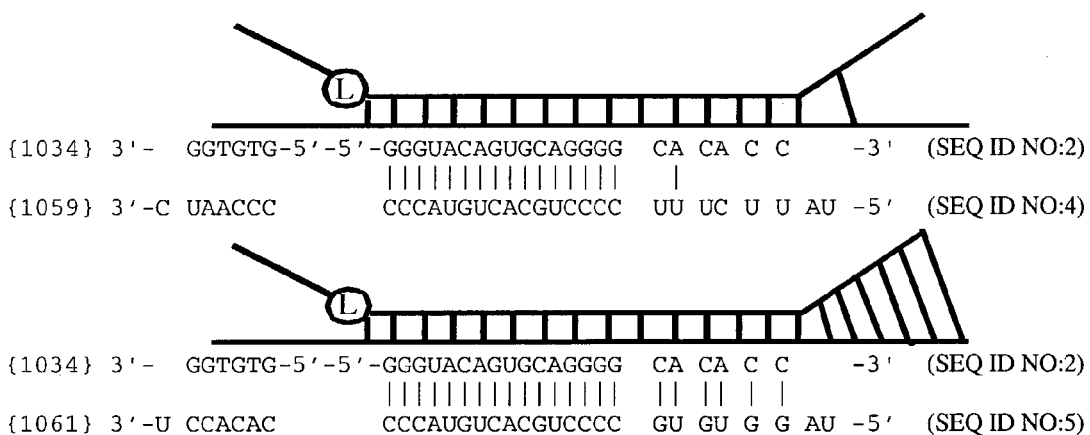

The measured Tm values for hybrids that included the 1034 probe provided reference examples for the behavior of a polynucleotide that included a 5'-5' linkage and only conventional nucleobases. The hybrid that included the 1034 probe and the 1059 target was characterized by a Tm of 68.9° C. This established a quantitative baseline value reflecting the stability of a hybrid having a structure wherein neither of the two arms of the probe substantially interacts with the target sequence, as shown in FIG. 4B. The nucleic acid hybrid that included the 1034 probe and the 1061 target was characterized by a Tm of 79.1 ° C. This value, which was higher than the Tm measured using the 1059 target, reflected the increased stability of a hybrid having a structure wherein only one of the two arms of the probe substantially interacted with the target, also as shown in FIG. 4B.

Figure 4C:
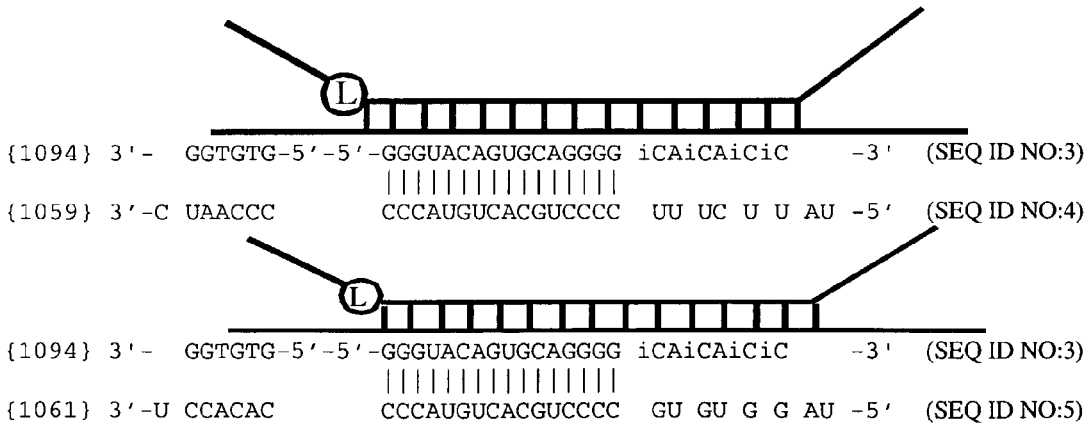

The measured Tm values for hybrids that included the 1094 parallel-stem hybridization probe validated the model structures shown in FIG. 3 and FIG. 4C by supporting a key prediction based on the following reasoning. If the presence of 5-methyl-iC nucleobases in the extension arm of the 1094 probe prevented interaction with target polynucleotide sequences falling outside the region hybridized by the target-complementary loop of the probe, then the Tm of the 1094/1061 hybrid should be similar to the Tm of the 1094/1059 hybrid. As indicated by the entries in Table 1, the Tms of both hybrids that included the 1094 probe were similar to each other. These results established that the arms of the 1094 probe did not interact with sequences present in the target. Thus, the arm components of a parallel-stem hybridization probe having an inversion arm, and an extension arm, where the extension arm contains nucleobase analogs that participate only in parallel base pairing, advantageously did not interact with target polynucleotide sequences, as shown in FIG. 4C.

Functionality of the parallel-stem hybridization probe was next investigated by comparing the fluorescence emission of the 1094 parallel-stem hybridization probe with the fluorescence emission of the 1093 molecular beacon. More specifically, these probes having stem-and-loop configurations were tested for their abilities to quench fluorescence in the absence of target, and to emit a fluorescent signal in the presence of a target.

Example 2 describes the methods used to demonstrate that target polynucleotide hybridization caused the parallel-stem hybridization probe to transition from a closed conformation to an open conformation that was detectable by fluorescent signal emission.

EXAMPLE 2

Target Polynucleotide Binding Triggers Signaling by Parallel-Stem Hybridization Probes Individual samples containing the 1093 molecular beacon or the 1094 parallel-stem hybridization probe and either of the two polynucleotide targets described in Example 1 were hybridized and monitored for fluorescence emission. In these procedures the concentrations of the probes were held constant at 0.3 µM, while the concentration of the target varied from 0–3 µM. Parallel procedures were carried out using the 1059 and 1061 targets. In all instances the mixtures were heated to 60° C. for 30 minutes, cooled to 42° C. for 30 minutes, and finally cooled to room temperature (about 23° C.) for 30 minutes before reading fluorescence at room temperature. These thermal step procedures promoted interaction between the probe and the target polynucleotide in the samples that included a target polynucleotide. Fluorescence measurements were carried out using a FLUOROSKAN ASCENT fluorometer (Labsystems, Inc.; Franklin, Mass.) at a 530 nm wavelength following excitation with light having a wavelength of 485 nm. Results obtained using the 1093 molecular beacon established the performance features of an authentic molecular beacon in this experimental system, and provided a basis for comparison with the parallel-stem hybridization probe.

Figure 5A:
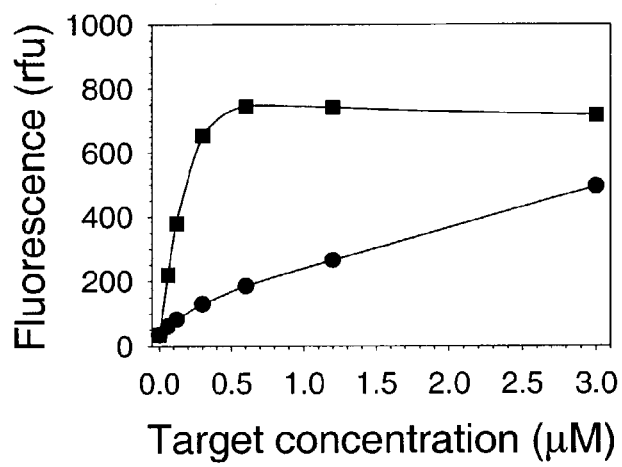
FIGS. 5A–5C are line graphs showing signals generated by self-reporting probes in the presence of increasing concentrations of target polynucleotide.

The graphic results presented in FIG. 5A showed that the 1093 molecular beacon exhibited a low level of baseline fluorescence in the absence of target, as expected. This indicated that the stem of the molecular beacon was in a "closed" configuration wherein the fluorophore and quencher moieties were maintained in close proximity so that fluorescence emission remained quenched. Increasing signal intensity in the presence of increasing levels of target represented evidence for binding of the molecular beacon to its target. Notably, fluorescence signals across the range of target levels tested were uniformly higher for trials that included the 1061 target rather than the 1059 target. This enhanced signal reflected the ability of the 1061 target, which is complementary to the 1093 molecular beacon over its entire length, to more effectively separate the fluoropore and quencher moieties when compared with the 1059 target.

Figure 5B:
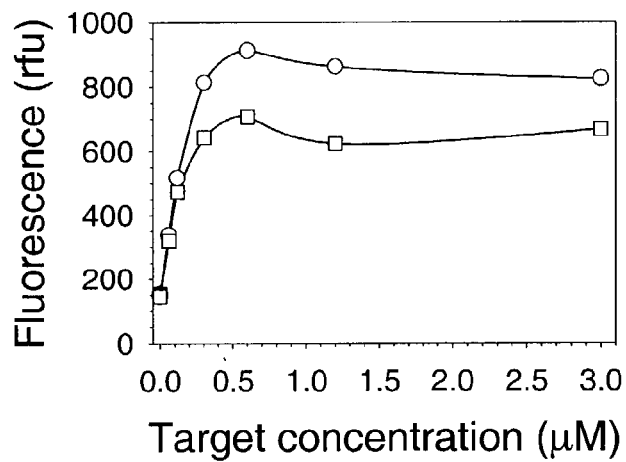

The graphic results presented in FIG. 5B confirmed that the 1094 parallel-stem hybridization probe interacted with the target polynucleotide in a manner substantially similar to the molecular beacon. At low levels of target, the parallel-stem hybridization probe gave a weak fluorescence signal. However, the fluorescence signal emitted by the probe increased substantially with increasing target levels. When compared with the behavior of the standard 1093 molecular beacon, the 1094 parallel-stem hybridization probe had a slightly higher baseline fluorescence emission in the absence of target. This may indicate that the parallel stem configuration was slightly less stable than an antiparallel stem of the same length, a possibility that would be consistent with observations that the Tm of the 1094 parallel-stem hybridization probe was lower that the Tm of the 1093 molecular beacon. Importantly, the difference between the signal strengths for hybridization with the 1059 and 1061 target polynucleotides was much less pronounced for the parallel-stem hybridization probe than for the molecular beacon. This represented further confirmation that the parallel-stem hybridization probe exhibited hybridization behavior that was substantially independent of the target sequence outside the region hybridized by the target-complementary loop region.

Figure 5C:
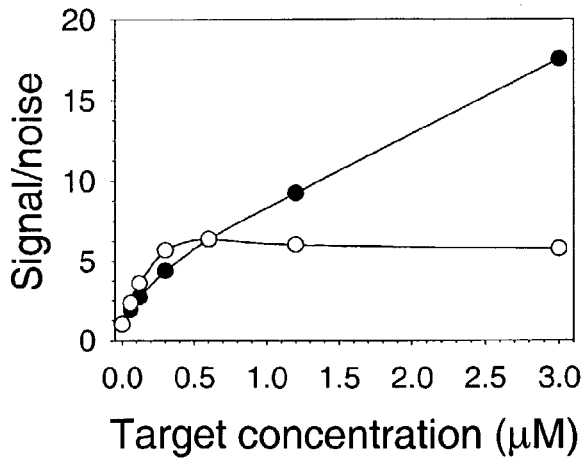

The information presented in FIG. 5C highlights one of the functional differences between the parallel-stem hybridization probe and the conventional molecular beacon. The signal-to-noise ratios (S/N) for the two probes as a function of 1059 target polynucleotide concentration were calculated by dividing the background-subtracted fluorescence signals measured for samples containing a probe and target by the background-subtracted fluorescence measured for each sample in the absence of a target polynucleotide. All of the data appearing in FIG. 5C was derived from the information that appears in FIGS. 5A and 5B. Inspection of the graph in FIG. 5C indicates that the S/N values for the molecular beacon strongly depended on the concentration of target polynucleotide over the range of concentrations tested in the procedure. In contrast, the parallel-stem hybridization probe exhibited S/N values that were substantially independent of target polynucleotide concentration over a wide concentration range. Thus, parallel-stem hybridization probes are well suited for use in qualitative assays that deliver a positive signal of substantially uniform strength over a wide range of analyte concentrations.

The unique properties of parallel-stem hybridization probes were further investigated by analyzing both the raw fluorescence signals and the calculated S/N ratios for parallel-stem hybridization probes and molecular beacons when used alone or in combination with each other, at different probe concentrations, and across a range of target polynucleotide concentrations.

Example 3 describes the methods used to demonstrate that parallel-stem hybridization probes and the molecular beacons displayed quantitatively different properties in hybridization assays. Notably, the parallel-stem hybridization probe yielded substantially constant signal production and signal-to-noise ratios when hybridized with target polynucleotides above a threshold level that was exceedingly low. As indicated below, the parallel-stem hybridization probe may be combined with a molecular beacon directed to the same target and used for "tuning" the S/N value of a hybridization signal without substantially compromising the magnitude of the fluorescence hybridization signal.

EXAMPLE 3

Parallel-Stem Hybridization Probes and Molecular Beacons Exhibit Different Functional Characteristics in Hybridization Assays Samples containing the 1093 molecular beacon, the 1094 parallel-stem hybridization probe, or a combination of these two probes were hybridized at one of several probe concentrations with 0–0.3 µM of the 1059 target polynucleotide essentially as described above. Samples containing the 1093 molecular beacon had probe concentrations of either 0.1 µM, 0.15 µM, 0.2 µM, 0.25 µM or 0.3 µM. Samples containing the 1094 parallel-stem hybridization probe had probe concentrations of 0.05 µM, 0.1 µM, 0.15 µM or 0.2 µM. Samples containing both the molecular beacon and the parallel-stem hybridization probe all had total probe concentrations of 0.3 µM, with different proportions of this total being due to each of the two probes. In all cases background fluorescence measurements from buffer controls were subtracted from the fluorescence signals measured for each sample. Corrected S/N values were calculated as described in the previous Example.

Figure 6A:
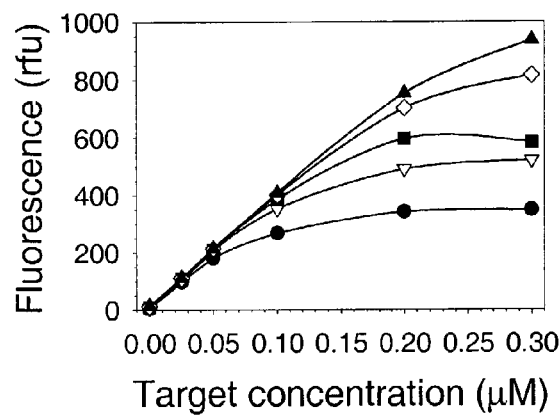
FIGS. 6A–6F are line graphs showing either fluorescence hybridization signal values or signal-to-noise ratios (S/N) plotted against increasing concentrations of the 1059 target polynucleotide.
Figure 6B:
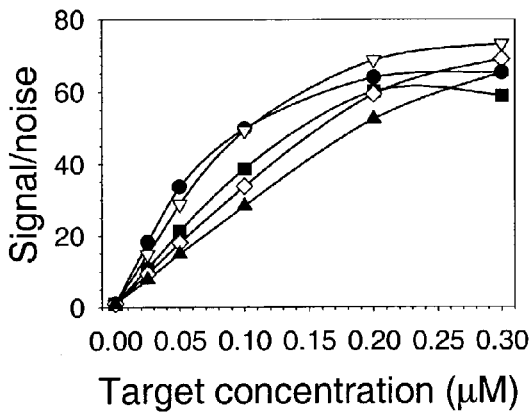
Figure 6C:
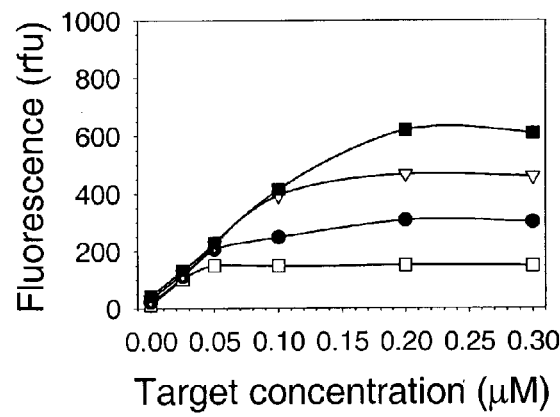
Figure 6D:
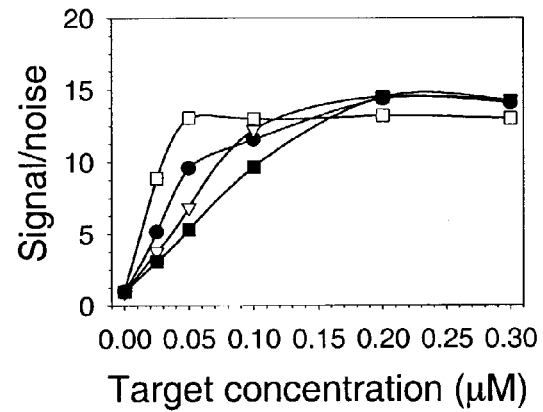
Figure 6E:
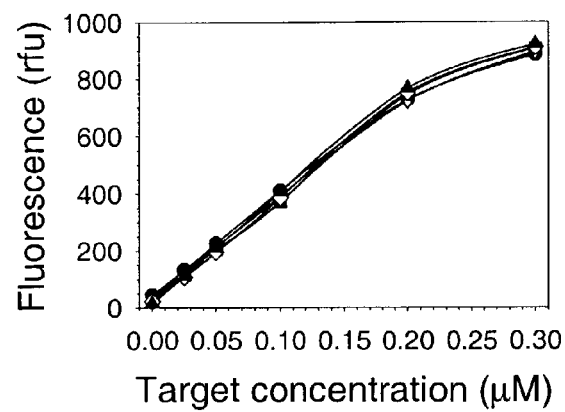

The results presented in FIGS. 6A–F confirmed that the parallel-stem hybridization probe and the molecular beacon exhibited fundamentally different behaviors in hybridization assays. FIG. 6A shows the corrected fluorescence signals for different concentrations of the 1093 molecular beacon following hybridization across a range of target polynucleotide concentrations. The magnitudes of the fluorescence signals clearly paralleled the amount of probe that was present in each sample. Thus, samples containing higher amounts of the molecular beacon yielded stronger signals than samples containing lower amounts of the probe across the range of target concentrations. The same trend was observed in samples containing the 1094 parallel-stem hybridization probe, as indicated by the results appearing in FIG. 6C. However, in contrast with samples containing the molecular beacon, samples containing the parallel-stem hybridization probe yielded maximum fluorescent signals in a more abrupt fashion wherein a constant signal strength (reflected by the substantially horizontal portions of each curve) was achieved in a manner dependent on both the probe and target polynucleotide concentrations. This indicated that the ultimate S/N value for a hybridization assay employing a parallel-stem hybridization probe could be manipulated by adjusting the amount of probe used in the procedure. FIG. 6E showed that the quantitative relationship between the concentration of target polynucleotide and the fluorescent signal produced in samples containing a combination of the parallel-stem hybridization probe and the molecular beacon was fully independent of the proportion of the each probe in the composition. More specifically, virtually identical results were achieved for samples containing 100%, 83%, 66%, 50% or 33% of total probe as molecular beacon with the remaining proportion being represented by the parallel-stem hybridization probe. This result could not have been derived by the simple addition of data points appearing in FIGS. 6A and 6C.

Figure 6F:
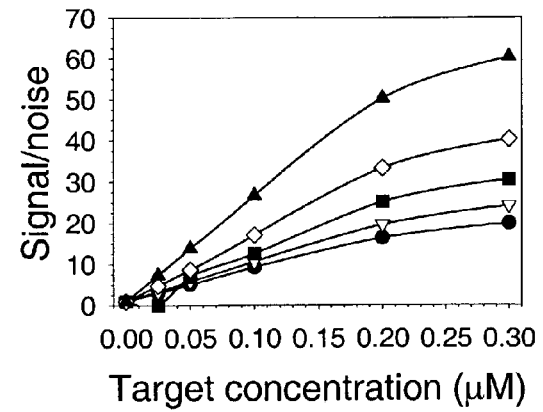

FIGS. 6B, 6D and 6F show the signal-to-noise ratios for the data presented in FIGS. 6A, 6C and 6E, respectively. FIG. 6B shows that the series of curves obtained in procedures using the 1093 molecular beacon had different initial slopes and different, but closely related values at the maximum target concentration that was tested in the procedure. In contrast, FIG. 6D shows that the curves generated using the data obtained for the parallel-stem hybridization probe had a different character. More particularly, these curves differed from each other in their initial slopes, but not in their maximum values at the highest target polynucleotide concentration used in the procedure. Additionally, when compared with results obtained using the molecular beacon, the maximum S/N values obtained using the parallel-stem hybridization probe were achieved at relatively low target polynucleotide concentrations. Thus, the parallel-stem hybridization probe achieved a substantially maximum S/N value at a low level of target polynucleotide, and then maintained that S/N value over a broad range of target concentrations. Finally, FIG. 6F shows how a family of distinct S/N curves could be obtained when the molecular beacon and parallel-stem hybridization probe were used in combination for hybridizing a target polynucleotide. Significantly, the features of the curves in FIG. 6F were clearly different from those shown for either of the two probe types when used alone. These results established that the parallel-stem hybridization probe differed markedly in its properties from the molecular beacon.

The rapid increases followed by substantially flat portions of the curves obtained using parallel-stem hybridization probes suggested certain utilities for this species of probe. For example, parallel-stem hybridization probes may be employed in qualitative hybridization assays wherein positive signals of substantially constant magnitude are desirable over a broad range of target concentrations. The conventional molecular beacon would not be suited for this application because the magnitudes of the fluorescence signal and the S/N value strongly depended on the amount of target polynucleotide that was present in the hybridization mixture. In contrast, the parallel-stem hybridization probe was capable of delivering substantially uniform signals for both high and low levels of target polynucleotide that exceed a particular minimum threshold.

Immobilized parallel-stem hybridization probes may also be used in connection with nucleic acid amplification assays for quantifying analyte polynucleotides in test samples. In some applications, such as a microarray of immobilized self-reporting parallel-stem hybridization probes and molecular beacons, the hybridization signal detected from the immobilized parallel-stem hybridization probe may provide a reference for comparison with the signal from the molecular beacon. Quantitative information about the amount of analyte polynucleotide in the sample may then be derived from that comparison. When the two probes are both directed against the same analyte polynucleotide target, and when the amount of analyte polynucleotide in the test sample exceeds a certain minimum threshold needed to produce a constant signal strength from the parallel-stem hybridization probe, then the signal from the parallel-stem hybridization probe will represent a substantially constant baseline for comparison with the signal produced by the molecular beacon.

To more fully illustrate the range of variables that may be changed without compromising the basic nature of the parallel-stem hybridization probe, another probe was prepared and tested. This additional probe employed a different inversion linkage that gave rise to a probe having two 5' ends instead of two 3' ends, and had a different stem sequence and length. In addition, this new parallel-stem hybridization probe did not contain nucleobase analogs, and was directed to a different polynucleotide target sequence. This additional probe, named 1262, had the structure: 5'-DABCYL-AAAAAAAAAAAAAGCAGGATGAAGAGGAA-3'-3'-TTTTTTTTTTTT-Fluorescein-5' (SEQ ID NO:8). Notably, the 1262 probe included a 3'-3' inversion linkage and had a parallel-stem duplex consisting of conventional A:T base pairing. As indicated above, A:T base pairs may participate in either parallel or antiparallel duplex formation. The presence of the inversion linkage in this probe forced the parallel stranded conformation. In contrast to the 1094 parallel-stem hybridization probe, the fluorophore label on the 1262 probe was linked to the terminus of the inversion arm instead of the terminus of the extension arm. A related probe with a conventional molecular beacon configuration was named 1261 and had the structure: 5'-DABCYL-AAAAAAAAAAAAAGCAGGATGAAGAGGAA TTTTTTTTTTTT-Fluoriscein-3' (SEQ ID NO:6). The 1261 probe had a sequence identical to the sequence of the 1262 probe, but did not include an inversion linkage. Underlined nucleotides in the probe sequences indicate residues that participated in the formation of stem duplexes. The target-complementary sequence of bases in the loop portions of the 1261 and 1262 probes is given by GCAGGATGAAGAG-GAA (SEQ ID NO:10). Notably, the probes and target used in these procedures were entirely made of DNA.

Finally, the methyl group on the thymine base located at position 19 in each of the two probes was carboxylated to provide a means for surface-immobilizing the probes. As indicated in the following Example, and despite changes in all of these variables, the 1262 parallel-stem hybridization probe functioned as a self-reporting hybridization probe having a stem-and-loop structure.

Example 4 describes the methods used to explore the range of structural variables that could be changed while still maintaining the functional features of a parallel-stem hybridization probe. Notably, the model target sequence employed in the following procedure was a hepatitis B virus polynucleotide sequence.

EXAMPLE 4

Parallel-Stem Hybridization Probe having a Parallel-Stranded Duplex Composed of Conventional Nucleobases The 1261 molecular beacon and the 1262 parallel-stem hybridization probe were synthesized using the procedures described above. Similarly, a synthetic DNA target polynucleotide named 1269, and having the sequence 5'-GTCT-GCGGCGTTTTATCATATTCCTCTTCATC-CTGCTGCTATGCCTCATCTTC TTAT-3' (SEQ ID NO:7), also was synthesized using conventional techniques that will be familiar to those having an ordinary level of skill in the art. The 1269 target was complementary to the 1261 and 1262 probes as indicated in FIG. 7.

Melting curves for the two probes individually or in combination with the DNA target were produced to assess probe:target interactions essentially as described under Example 1. Again, the first derivative of the curve plotted on a graph of absorbance against temperature was used to pinpoint the inflection points which represented the Tm values. Results of these procedures are presented in Table 2.

The ability of the 1262 parallel-stem hybridization probe to function as a self-reporting probe was assessed by monitoring fluorescence emission in the presence and absence of the complementary 1269 target polynucleotide. As a control, fluorescence emission by the 1261 molecular beacon also was measured in the presence and absence of the target polynucleotide. The 1262 and 1261 probes (0.3 µM each) in TENT buffer were either tested alone or combined with the 1269 target polynucleotide over a range of 0–3 µM and tested for fluorescence emission essentially as described in Example 2. Results of these procedures are presented graphically in FIG. 8.

Figure 8:
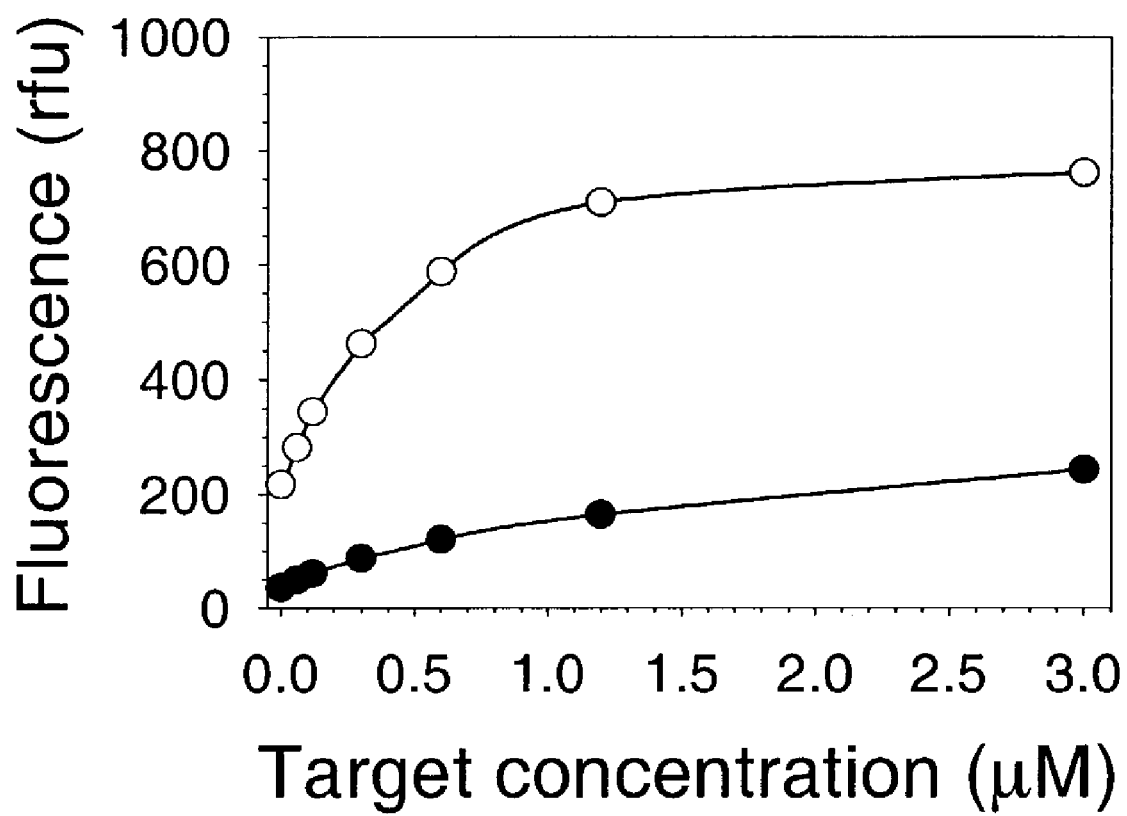
FIG. 8 is a line graph showing fluorescence signals generated by the 1261 molecular beacon and the 1262 parallel-stem hybridization probe in the presence of increasing amounts of target polynucleotide. The curves represent results for the 1262 parallel-stem hybridization probe and the 1269 target (○), and for the 1261 molecular beacon and the 1269 target (●).

The results presented in Table 2 and in FIG. 8 showed that the 1262 parallel-stem hybridization probe hybridized to the 1269 target polynucleotide in a manner consistent with the functionality of a self-reporting molecular beacon. The Tm value for the 1262 parallel-stem hybridization probe was somewhat lower than the Tm of the 1261 molecular beacon, as expected. This trend was repeated in the results obtained for each of the probes when hybridized with the target polynucleotide. FIG. 8 shows that the 1261 molecular beacon exhibited a low level of background fluorescence in the absence of target polynucleotide, and that fluorescence emission increased with increasing levels of target. As expected, the molecular beacon was in a closed conformation in the absence of target, but transitioned to the open conformation upon target binding. Similarly, the 1262 parallel-stem hybridization probe exhibited a low level of background fluorescence in the absence of a complementary target polynucleotide. Like the 1261 molecular beacon, the fluorescence from the 1262 parallel-stem hybridization probe increased when contacted with increasing amounts of the complementary polynucleotide target. These features of the 1262 probe confirmed the general utility of parallel-stem hybridization probes as self-reporting probes having stem-and-loop structures.

TABLE 2

Quantifying Probe: Target Interactions

| Probe Name | Probe Features | Tm at 260 nm (in ° C.) |
|---|---|---|
| 1261 | Molecular Beacon | 47.9 |
| 1262 | Parallel-Stem Hybridization Probe | 36.9 |
| Probe/Target | | |
| 1261/1269 | Molecular Beacon | 48.4 |
| 1262/1269 | Parallel-Stem Hybridization Probe | 41.4 |

The foregoing results demonstrated that a stem-and-loop hybridization probe can have an arm structure with a backbone polarity opposite the polarity of a target-complementary loop sequence, and that an inverted arm structure was substantially precluded from interacting with the target, even when the nucleobase sequences of the arm and the target had a complementary order. Thus, a single inversion linkage positioned between one of the probe termini and the target-complementary sequence of the probe was sufficient to inhibit interactions between the target and the inverted arm of the probe.

The following illustration demonstrated that a stem-and-loop hybridization probe having two inversion linkages, one flanking each end of the target-complementary sequence of the probe, transitioned from a closed state to an open state following interaction with an appropriate target. It necessarily follows from this observation that the stem structure, which was composed of the interactive arm pair of the dual inversion probe, must have formed by conventional antiparallel base pairing. Importantly, the nucleobase sequences located between each of the two probe termini and the adjacent inversion linkage (i.e., the nucleobase sequence of the two arms of the probe) have the same backbone polarity, but a polarity opposite that of the target-complementary sequence that is contained within the dual inversion probe. Taken together with the fact that inversion arms are substantially incapable of interacting with the target, each arm of the dual inversion probe advantageously was substantially precluded from interacting with the target.

Eight different self-reporting constructs were created to illustrate the utility of dual inversion probes. Each of the probe constructs included a DABCYL quencher moiety at one probe terminus and a fluorescein fluorophore moiety at the opposite probe terminus. The structures of oligonucleotides, including probes and synthetic target molecules, that were used for demonstrating the utility of dual inversion probes are presented in Tables 3–6.

TABLE 3

Oligonucleotides Used for illustrating the Utility of Dual Inversion Probes (Pan-Bacterial Probes and Targets)

| Oligo Name | Sequence | SEQ ID NO: |
|---|---|---|
| 1521 | 5'-[F]-CCGAGGACCGACAAGGAAUUUCGCGTC-CTCGG-[D]-3' | 11 |
| 1522 | 5'-[D]-GGCTCCTG-3'-3'-CGCUUUAAGGAA-CAGC-5'-5'-CAGGAGCC-[F]-3' | 12 |
| 1254 | 5'-GGCCGUACCUAUAACGGUCCUAAGGUAGCGAAAUUCC UUGUCGGGUAAGUUCCGACCUGCAC-3' | 13 |
| 1523 | 5'-GGCCGUACCUAUAACGGUCCCGAGGACGCGAAAUUCC UUGUCGGUCCUCGGCCGACCUGCAC-3' | 14 |

"[F]" represents fluorescein
"[D]" represents DABCYL

TABLE 4

Oligonucleotides Used for Illustrating the Utility of Dual Inversion Probes (Pan-Fungal Probes and Targets)

| Oligo Name | Sequence | SEQ ID NO: |
|---|---|---|
| 1531 | 5'-[F]-CCGAGGACGUCUGGACCUGGUGAGUUUCCCGUCCUCG G-[D]-3' | 15 |
| 1532 | 5'-[D]-GGCTCCTG-3'-3'-CCCUUUGAGUGGUCCAGGUCUG-5'-5'-CAGGAGCC-[F]-3' | 16 |
| 1307 | 5'-CUGCGGCUUAAUUUGACUCAACACGGGAAACUCACC AGGUCCAGACACAAUAAGGAUUGACAGAUUGAGAGC | 17 |

TABLE 4-continued

Oligonucleotides Used for Illustrating the Utility of Dual Inversion Probes (Pan-Fungal Probes and Targets)

| Oligo Name | Sequence | SEQ ID NO: |
|---|---|---|
|  | UC-3' |  |
| 1533 | 5'-CUGCGGCUUAAUUUGACCCGAGGACGGGAAACUCACC AGGUCCAGACGUCCUCCGGAUUGACAGAUUGAGAGC UC-3' | 18 |

"[F]" represents fluorescein
"[D]" represents DABCYL

TABLE 5

Oligonucleotides Used for Illustrating the Utility of Dual Inversion Probes (Enterobacteriaceae Probes and Targets)

| Oligo Name | Sequence | SEQ ID NO: |
|---|---|---|
| 1541 | 5'-[F]-CCGAGGACCCGCUUGCUCUCGCGAGGTCCT CGG-[D]-3' | 19 |
| 1542 | 5'-[D]-GGCTCCTG-3'-3'-GAGCGCUCUCGUUCG CC-5'-5'-CAGGAGCC-[F]-3' | 20 |
| 1317 | 5'-GGGCUACACACGUGCUACAAUGGCGCAUACAAAGAG AAGCGACCUCGCGAGAGCAAGCGGACCUCAUAAAGUG CGUCGUAGUCCGG-3' | 21 |
| 1543 | 5'-GGGCUACACACGUGCUACAAUGGCGCAUACAAAGACC GAGGACCUCGCGAGAGCAAGCGGGUCCUCGGAAGUGC GUCGUAGUCCGG-3' | 22 |

"[F]" represents fluorescein
"[D]" represents DABCYL

TABLE 6

Oligonucleotides Used for Illustrating the Utility of Dual Inversion Probes (Gram Positive Bacterial Probes and Targets)

| Oligo Name | Sequence | SEQ ID NO: |
|---|---|---|
| 1551 | 5'-[F]-CCGAGGACGAGGGAACCUUUGGGCGCGTCCTCGG-[D]-3' | 23 |
| 1552 | 5'-[D]-GGCTCCTG-3'-3'-CGCGGGUUUCCAAGGGAG-5'-5'-CAGGAGCC-[F]-3' | 24 |

TABLE 6-continued

Oligonucleotides Used for Illustrating the Utility
of Dual Inversion Probes
(Gram Positive Bacterial Probes and Targets)

| Oligo Name | Sequence | SEQ ID NO: |
|---|---|---|
| 1327 | 5'-UGGGGCGGUUGCCUCCUAAAGAGUAACGGAGGCGCCC AAAGGUUCCCUCAGCCUGGUCGGCAAUCAGGUGUU-3' | 25 |
| 1553 | 5'-UGGGGCGGUUGCCUCCUAAAGAGCCGAGGACGCGCCC AAAGGUUCCCUCGUCCUCGGCGGCAAUCAGGUGUU-3' | 26 |

"[F]" represents fluorescein
"[D]" represents DABCYL

Each of the entries shown in Tables 3–6 served either as a molecular beacon probe, a dual inversion probe, an RNA target containing a natural sequence complementary to the loop portions of the probes, or an RNA target made complementary to both the loop portions and the arm sequences of the probes. The 1521 pan-bacterial rRNA specific molecular beacon had arms 8 base pairs long with a deoxy backbone, and a target-complementary 2'-OMe loop that was 16 bases long. The 1522 pan-bacterial rRNA specific dual inversion probe had arms 8 base pairs long with a deoxy backbone, and a target-complementary 2'-OMe loop that was 16 bases long. The 1254 62-mer synthetic RNA target was used for hybridizing the pan-bacterial specific probes. The 1523 target oligonucleotide was essentially the same as the 1254 oligonucleotide except that the sequence flanking the probe-complementary sequence of 1254 was exactly complementary to the arm sequences of the 1521 pan-bacterial molecular beacon. The 1531 pan-fungal rRNA specific molecular beacon had arms 8 base pairs long with a deoxy backbone, and a target-complementary 2'-OMe loop that was 22 bases long. The 1532 pan-fungal rRNA specific dual inversion probe had arms 8 base pairs long with a deoxy backbone, and a target-complementary 2'-OMe loop that was 22 bases long. The 1307 oligonucleotide was a 75-mer synthetic RNA target that was used for hybridizing pan-fungal probes. The 1533 oligonucleotide was essentially the same as the 1307 oligonucleotide except that the sequence flanking the probe-complementary sequence of 1307 was exactly complementary to the arm sequences of the 1531 pan-fungal molecular beacon. The 1541 oligonucleotide was an Enterobacteriaceae rRNA specific molecular beacon that had arms 8 base pairs long with a deoxy backbone, and a target-complementary 2'-OMe loop that was 17 bases long. The 1542 Enterobacteriaceae rRNA specific dual inversion probe had arms 8 base pairs long with a deoxy backbone, and a target-complementary 2'-OMe loop that was 17 bases long. The 1317 oligonucleotide was an 86-mer synthetic RNA target that was used for hybridizing Enterobacteriaceae-specific probes. The 1543 oligonucleotide was essentially the same as the 1317 oligonucleotide except that the sequence flanking the probe-complementary sequence of 1317 was exactly complementary to the arm sequences of the 1541 Enterobacteriaceae molecular beacon. The 1551 molecular beacon had binding specificity for the rRNA of Gram positive bacteria, and a structure having arms 8 base pairs long with a deoxy backbone, and a target-complementary 2'-OMe loop that was 18 bases long. The 1552 dual inversion probe had binding specificity for the rRNA of Gram positive bacteria, and a structure having arms 8 base pairs long with a deoxy backbone, and a target-complementary 2'-OMe loop that was 18 bases long. The 1327 oligonucleotide was a 72-mer synthetic RNA target, having a sequence derived from *Micrococcus luteus*, that was used for hybridizing probes specific for the rRNA of Gram positive bacteria. The 1553 oligonucleotide was essentially the same as the 1327 oligonucleotide except that the sequence flanking the probe-complementary sequence of 1327 was exactly complementary to the arm sequences of the 1551 Gram positive molecular beacon probe.

The use of two different targets for hybridizing each of the molecular beacons and corresponding dual inversion probes provided a means for establishing functional differences between the two types of hybridization probe. More particularly, each of the probes listed in Tables 3–6 was hybridized with one of two different synthetic target oligonucleotides, also listed in the tables. The first target contained a sequence complementary to the target-complementary loops of the corresponding probes, but not to the flanking arm sequences. The second target further contained sequences fully complementary to the arm sequences of the molecular beacon. Although the bases in these flanking sequences were ordered to be complementary to the arm sequences of the corresponding dual inversion probes, those arm sequences were precluded from interacting with the second target because the polarity of the backbone was reversed. Thus, where the loops of both of the probes were able to interact with the first oligonucleotide target, the arms of only the molecular beacon, and not the arms of the dual inversion probe, were additionally able to hybridize over their lengths with the second target. Differential interactions of the two probes with the second target reflected the differential ability of the arm structures of the molecular beacon and the dual inversion probe to interact with the target.

Example 5 describes the methods used to demonstrate that target polynucleotide hybridization caused dual inversion probes to transition from closed conformations to open conformations that were detectable by fluorescent emissions.

EXAMPLE 5

Binding to Target Polynucleotide Triggers Signaling by Dual Inversion Probes

The molecular beacon and dual inversion probes listed in Tables 3–6 were hybridized to corresponding synthetic RNA targets, also presented in the tables. All probes were synthesized by solid phase phosphite triester chemistry using either DABCYL-linked controlled pore glass and 5' fluorescein-labeled phosphoramidite, or fluorescein-linked controlled pore glass and 5' DABCYL-labeled phosphoramidite on a Perkin-Elmer (Foster City, Calif.) EXPEDITE model 8909 automated synthesizer and methods that will be familiar to those having an ordinary level of skill in the art. The 5'-5' and 3'-3' inversion linkages incorporated into the dual inversion probes were created using reagents obtained from Glen Research Corporation (Sterling, Va.), Proligo (Boulder, Colo.) or Pierce Biotechnology (Rockford, Ill.). All probes were constructed using 2'-methoxy ribonucleotide analogs in their target-complementary loop regions, and 2'-deoxyribonucleotides in their arm regions. Notably, other dual inversion probes directed to different targets were prepared using 2'-deoxoribonucleotides in their target-complementary loop regions and then used with success. Accordingly, the target-complementary loop region and arm portions of dual inversion probes may contain standard nucleotides, nucleotide analogs, or even mixtures of standard nucleotides and nucleotide analogs. Following synthesis, the probes were deprotected and cleaved from the solid support matrix and then purified using polyacrylamide gel electrophoresis followed by HPLC according to procedures that will be familiar to those having an ordinary level of skill in the art.

Individual samples containing either one of the molecular beacon probes or one of the dual inversion probes and one of the two corresponding target molecules were hybridized and monitored for fluorescence emission. For example, to monitor and compare the activities of the 1521 pan-bacterial molecular beacon and 1522 pan-bacterial dual inversion probe, samples of each of these probes were combined separately with the 1254 and 1523 targets (i.e., a total of four hybridization reactions). Similar combinations were used for measuring the activities of the probes specific for the pan-fungal, Enterobacteriaceae, and Gram positive bacterial targets. The concentrations of probes used in these procedures were held constant at 0.3 µM while the concentrations of the targets varied from 0–3 µM. Hybridization reactions were carried out in a solution of TENL buffer (50 mM Tris-HCl (pH 8.0), 50 mM NaCl, 0.1 mM EDTA, 0.1% lithium lauryl sulfate). In all instances the mixtures were heated to 60° C. for 30 minutes, cooled to 42° C. for 30 minutes, and finally cooled to room temperature (about 23° C.) for 30 minutes before reading fluorescence at room temperature. Fluorescence measurements were again carried out using the FLUOROSKAN ASCENT fluorometer (Labsystems, Inc.; Franklin, Mass.) at a 530 nm wavelength following excitation with light having a wavelength of 485 nm. "Background" fluorescence was determined as the fluorescent signal measured by the instrument in the absence of any probe or target. "Signal" in this system is represented by the magnitude of the fluorescent emission. "Background-subtracted fluorescent signals" were calculated by subtracting background fluorescence from the measured signals. "Noise" in the system represented the magnitude of the fluorescent signal measured for labeled probe in the absence of any target. "Background-subtracted signal-to-noise" (corrected S/N) ratios were calculated by dividing background-subtracted fluorescent signals by the value of background-subtracted noise [(signal-background)/(noise-background)]. These procedures established the performance characteristics of authentic molecular beacons in this experimental system, and provided a basis of comparison for each of the dual inversion probes.

The results presented in FIGS. 11A–D indicated that the dual inversion probes and corresponding molecular beacons showed qualitatively similar behaviors. The graphical presentation of corrected S/N shown in the figures represents interactions between the various probes and corresponding targets that were not fully complementary to the arm sequences of the molecular beacons. The graphs clearly show that each of the probes exhibited increased fluorescence following hybridization to the target oligonucleotide. This was consistent with an expected transition from a closed state to an open state following interaction with a complementary target, as would result from the physical separation of the fluorophore and quencher moieties due to opening of a stem structure that was closed in the absence of target. Interestingly, the corrected S/N values for the dual inversion probes were uniformly somewhat lower than the corrected S/N values for the corresponding molecular beacons. The coefficients of variation (n=6) of the combined noise levels for the molecular beacons and corresponding dual inversion probes used in these procedures were 2.5%, 3.4%, 12.9% and 11.7% for the pan-bacterial, pan-fungal, Enterobacteriaceae and Gram positive probes, respectively. Notably, the levels for the pan-bacterial probes and pan-fungal probes were virtually identical. This showed that dual inversion probes did not exhibit substantially different background fluorescence than corresponding molecular beacons in the absence of target, and suggested that relative differences in the corrected S/N values for molecular beacons and dual inversion probes reflected differences in the physical properties and hybridization characteristics of the two probe species.

Figure 12:
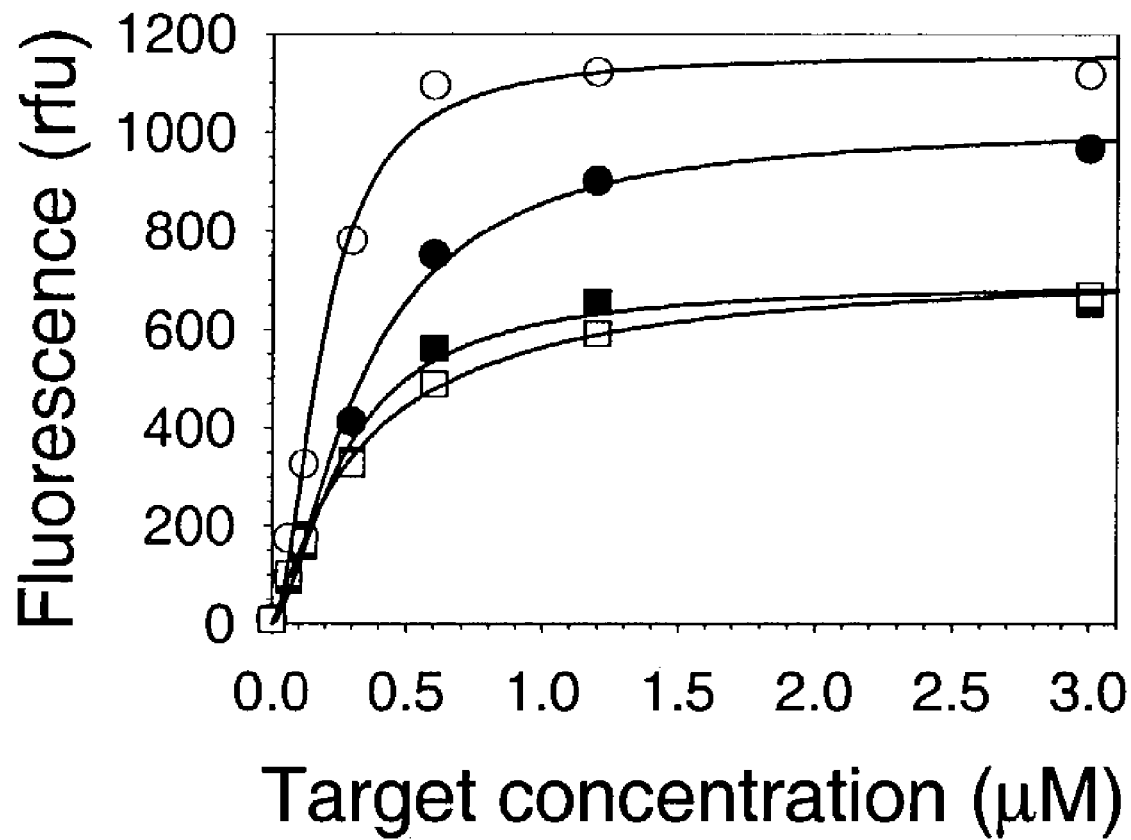
FIG. 12 is a line graph showing the background-subtracted fluorescent signal values as a function of target concentration for pan-fungal molecular beacons and dual inversion probes interacting with two different targets. The graph shows results for the 1531 molecular beacon interacting with the 1307 (●) and 1533 (○) targets, and for the 1532 dual inversion probe interacting with the 1307 (■) and 1533 (□) targets.

Results from these procedures also confirmed that dual inversion probes did not preferentially interact with target oligonucleotides having base sequences complementary to the arm sequences, but with reversed polarity. For example, FIG. 12 shows background-subtracted fluorescence measurements for each of the 1531 pan-fungal molecular beacon and 1532 dual inversion probe interacting with either the 1307 conventional target or the 1533 target that included sequences fully complementary to the target-complementary loop and arm sequences of the molecular beacon. Notably, some of the same data used to produce the graph shown in FIG. 12 were also used for producing the graph shown in FIG. 11B. As will be clear from examining FIG. 12, the molecular beacon yielded a greater fluorescent signal when hybridized with the target that was complementary to both the loop and arm sequences when compared with the conventional target at all target concentrations that were tested. This presumably reflects either enhanced probe binding or more effective separation of the fluorophore and quencher moieties as the result of arm:target interactions with the fully complementary 1533 target. In contrast, the corresponding dual inversion probe interacted substantially identically with both of the targets. Indeed, none of the four dual inversion probes tested in this procedure interacted more strongly with the targets that were fully complementary to the corresponding molecular beacons. However, the pan-fungal and pan-bacterial molecular beacons showed markedly enhanced fluorescence when hybridized with the fully complementary targets. The Gram positive molecular beacon showed substantially no preference for one target over the other, while the Enterobacteriaceae-specific molecular beacon showed a slight decrease in the fluorescent signal with the fully complementary target, a result that may not be statistically significant.

The data trend clearly established that dual inversion probes did not interact more strongly with targets having a single backbone polarity and base sequence complementary to the arm sequences of corresponding molecular beacons. However, it was common for molecular beacons to exhibit enhanced interactions with targets that included sequences complementary to the sequences of the arms. These conclusions were fully consistent with the results and conclusions discussed above in connection with parallel-stem hybridization probes.

Several different self-reporting constructs were created to illustrate the utility of dual inversion probes that included a chemical linker at the position of one or both of the inversion linkages. Each of the constructs included a DABCYL quencher moiety at the 5' terminus, a fluorescein fluorophore at the 3' terminus, and included a target-complementary loop sequence specific for HIV-1. The 1501 probe was substantially the same as the above-described 1093 conventional molecular beacon, but omitted the non-nucleotide linker contained within the target-complementary sequence. The 1502 construct was a standard dual inversion probe. The remaining constructs were dual inversion probes that included one of two different chemical linker moieties interposed between the target-complementary loop and the arm sequences of the probe. In these constructs the inversion linkage is said to include the chemical linker moiety because the linker is neither part of the loop nor part of the arm, but is instead part of the linkage that joins the loop and arm sequences of the probe. The 3'-3' inversion linkage of the 1503 probe included an aliphatic 3 carbon ("propyl") linker having the structure —(CH$_2$)$_3$—. The carbon atoms of the propyl linker essentially duplicate the spacing of the three carbon atoms that are typically positioned between the 3' and 5' oxygen atoms of a ribose or deoxyribose moiety that comprises a polynucleotide backbone. The 5'-5' inversion linkage of the 1504 probe similarly included a propyl linker. The 3'-3' inversion linkage of the 1505 probe included an 8 atom "triethylene glycol" linker having the structure —(CH$_2$)$_2$O(CH$_2$)$_2$O(CH$_2$)$_2$—. The 5'-5' inversion linkage of the 1506 probe included a triethylene glycol linker. Both the 3'-3' and 5'-5' inversion linkages of the 1507 probe included propyl linkers. Both the 3'-3' and 5'-5' inversion linkages of the 1508 probe included triethylene glycol linkers. The structures of the various probes are presented in Table 7. Nucleobase sequences corresponding to the arm portions of the probes are underlined in the table.

TABLE 7

Oligonucleotides Used for Illustrating the Utility of Inversion Probes Having Inversion Linkages that Include Chemical Linkers

| Oligo Name | Sequence | SEQ ID NO: |
|---|---|---|
| 1501 | 5'-[D]-GGTGTGGGGUACAGUGCAGGGGCACACC-[F]-3' | 27 |
| 1502 | 5'-[D]-GGTGTG-3'-3'-GGGUACAGUGCAGGGG-5'-5'-CACACC-[F]-3' | 28 |
| 1503 | 5'-[D]-GGTGTG-3'-linker-3'-GGGUACAGUGCAGG GG-5'-5'-CACACC-[F]-3' | 29 |
| 1504 | 5'-[D]-GGTGTG-3'-3'-GGGUACAGUGCAGGGG-5'-linker-5'-CACACC-[F]-3' | 30 |
| 1505 | 5'-[D]-GGTGTG-3'-linker-3'-GGGUACAGUGCAGG GG-5'-5'-CACACC-[F]-3' | 31 |
| 1506 | 5'-[D]-GGTGTG-3'-3'-GGGUACAGUGCAGGGG-5'-linker-5'-CACACC-[F]-3' | 32 |
| 1507 | 5'-[D]-GGTGTG-3'-linker-3'-GGGUACAGUGCAGG GG-5'-linker-5'-CACACC-[F]-3' | 33 |
| 1508 | 5'-[D]-GGTGTG-3'-linker-3'-GGGUACAGUGCAGG GG-5'-linker-5'-CACACC-[F]-3' | 34 |

"[F]" represents fluorescein
"[D]" represents DABCYL

Example 6 describes the methods used to demonstrate that dual inversion probes which included at least one chemical linker at the position of the inversion linkage transitioned from a closed conformation to an open conformation following hybridization with a target polynucleotide.

EXAMPLE 6

Signaling by Dual Inversion Probes Containing Inversion Linkages that Include Chemical Linkers The probes presented in Table 7 were hybridized to synthetic targets that had been prepared using 2'-OMe nucleotide analogs instead of ribonucleotides, a change that helped ensure chemical stability of the targets while having substantially no effect on the outcome of experimental results. Accordingly, the results obtained in studies using dual inversion probes and parallel-stem hybridization probes were expected to be directly comparable. As in Example 1, all dual inversion probes were synthesized by solid phase phosphite triester chemistry using DABCYL-linked controlled pore glass and 5' fluorescein-labeled phosphoramidite on a Perkin-Elmer (Foster City, Calif.) EXPEDITE model 8909 automated synthesizer and methods that will be familiar to those having an ordinary level of skill in the art. The 5'-5' and 3'-3' inversion linkages incorporated into the dual inversion probes were created using reagents obtained from Glen Research Corporation (Sterling, Va.). "SPACER C3" phosphoramidite (3-(4,4'-dimethoxytrityloxy)propyl-1-[(2-cyanoethyl)-(N,N-diisopropyl)]-phosphoramidite) and "SPACER 9" phosphoramidite (9-O-dimethoxytrityl-triethylene glycol,1-[(2-cyanoethyl)-(N,N-diisopropyl)]-phosphoramidite), which were used for introducing the propyl and triethylene glycol chemical linkers, respectively, also were purchased from Glen Research Corporation. All probes were constructed using 2'-methoxy ribonucleotide analogs in their target-complementary loop regions, and 2'-deoxyribonucleotides in their stem regions. Following synthesis, the probes were deprotected and cleaved from the solid support matrix and then purified using polyacrylamide gel electrophoresis followed by HPLC, all according to procedures that will be familiar to those having an ordinary level of skill in the art.

The probes were hybridized to appropriate targets and assayed for binding by monitoring fluorescent signal production. More specifically, the 1501 molecular beacon was hybridized to a 1510 target polynucleotide synthesized using 2'-OMe RNA analogs and having the sequence 5'-UAGGU-GUGCCCUGCACUGUACCCCACACCU-3' (SEQ ID NO:35). All of the dual inversion probes were hybridized to a 1511 target polynucleotide synthesized using 2'-OMe RNA analogs and having the sequence 5'-UCCACACCCCAU-GUCACGUCCCCGUGUGGAU-3' (SEQ ID NO:36). In these procedures the concentrations of the probes were held constant at 0.3 μM, while the concentrations of the target varied from 0–3 μM. In all instances the mixtures were heated in TENT buffer to 60° C. for 30 minutes, cooled to 42° C. for 30 minutes, and finally cooled to room temperature (about 23° C.) for 30 minutes before reading fluorescence at room temperature. Fluorescence measurements were again carried out using the FLUOROSKAN ASCENT fluorometer (Labsystems, Inc.; Franklin, Mass.) at a 530 nm wavelength following excitation with light having a wavelength of 485 nm. The thermal step procedures promoted interaction between the probe and the target polynucleotide in the samples that included a target polynucleotide. Results obtained using the 1501 molecular beacon established the performance features of an authentic molecular beacon in this experimental system, and provided a basis of comparison for each of the dual inversion probes.

Figure 13:
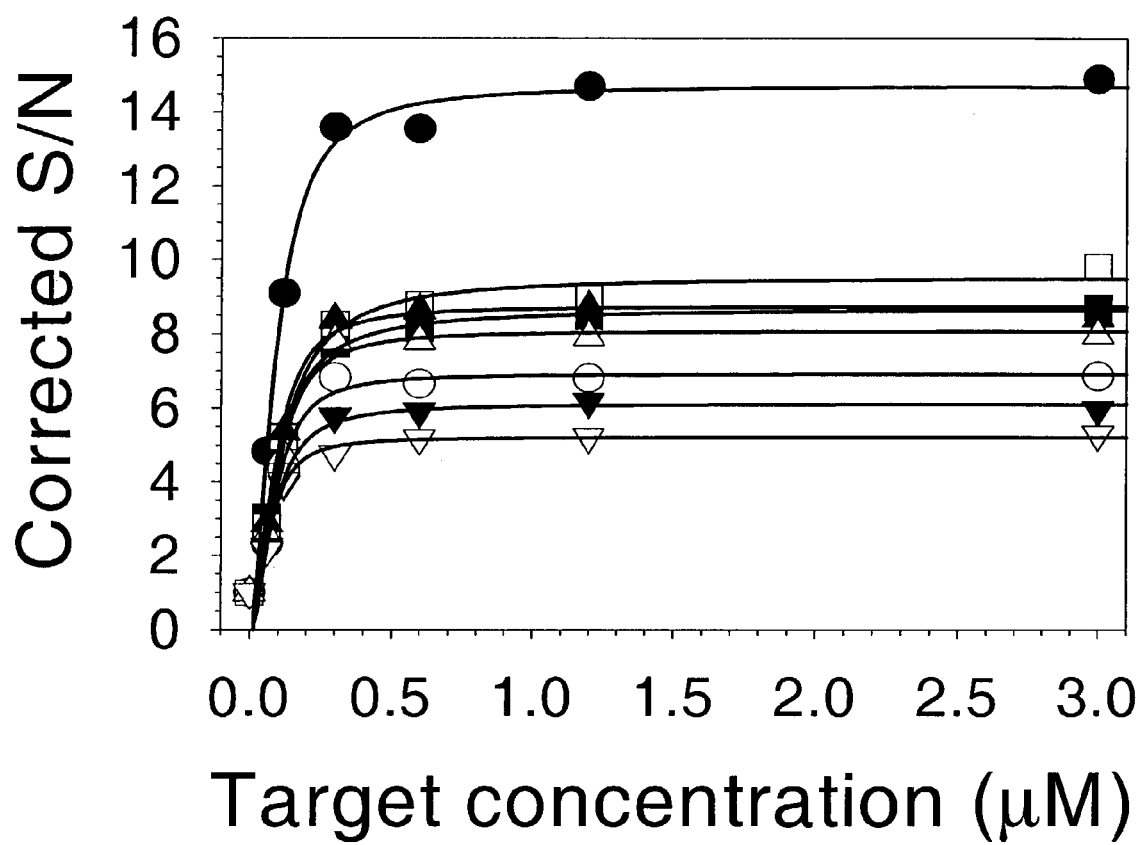
FIG. 13 is a line graph showing corrected signal-to-noise ratios (S/N) plotted against increasing concentrations of target polynucleotide for various probes. The 1501 (▽) probe was a conventional molecular beacon. The 1502 (●) probe was a dual inversion probe. The 1503 (○), 1504 (■), 1505 (□), 1506 (▲), 1507 (△), and 1508 (▼) probes were all dual inversion probes having at least one inversion linkage that included a chemical linker.

The graphic results presented in FIG. 13 demonstrated that probes containing inversion linkages which included optional chemical linkers transitioned from a closed state to an open state following hybridization to a complementary target polynucleotide. More specifically, each of the probes tested in this procedure gave increasingly high corrected S/N levels that plateaued when hybridized with increasing concentrations of a complementary target. Notably, in this procedure the 1501 conventional molecular beacon showed the least dramatic difference in signal strength between the closed and opened configurations, the conventional dual inversion probe gave the most dramatic differences, and the dual inversion probes that included a chemical linker at the position of at least one of the inversion linkages gave intermediate levels of signaling. This proved that one or more non-nucleotide linkers could be included in the backbone of an inversion probe while allowing the probe to hybridize to a target polynucleotide and transition from a closed state to an open state.

In addition to non-nucleotide linkers that are unlabeled, such as the propyl and triethylene glycol linkers employed in the foregoing Example, other non-nucleotide linkers, including detectably labeled non-nucleotide linkers, can be included in the structures of parallel-stem hybridization probes and dual inversion probes. More particularly, labeled or unlabeled non-nucleotide linkers can be joined to either or both of the arm structures, to the target-complementary loop structures, or even at the positions of one or both of the inversion linkages of the invented probes. In certain preferred embodiments the inversion probe includes at least one inversion linkage that includes a non-nucleotide linker. Even more preferably, the non-nucleotide linker includes a detectable label so that the probe, once hybridized to a complementary target polynucleotide, can be detected. For example, the chemical linker may include in its structure a radioactive atom, such as a $^{32}P$, $^{14}C$ or $^{3}H$ atom, which can be detected using techniques that will be familiar to those having an ordinary level of skill in the art. Alternatively, the chemical linker can be joined to a chemiluminescent label, such as an acridinium ester label of the type described herein above.

In a highly preferred embodiment the chemical linker is a non-nucleotide linker of the type described by Arnold et al., in U.S. Pat. No. 6,031,091, the disclosure of this patent document being incorporated by reference herein. This patent document particularly discloses how to make and use phosphoramidites for incorporating non-nucleotide linkers into the structure of synthetic polynucleotides, and further discloses how to attach detectable labels, including chemiluminescent and fluorescent moieties, to the non-nucleotide linker. The structure of highly preferred non-nucleotide linker phosphoramidites that can be used for preparing inversion probes containing non-nucleotide linkers are described in Example 3(C) and in FIG. 5a of the Arnold patent. Thus, inversion probes optionally may include non-nucleotide linkers, and these non-nucleotide linkers may be detectably labeled non-nucleotide linkers. Examples of preferred detectable labels include chemiluminescent labels, such as acridinium ester labels of the type disclosed in U.S. Pat. Nos. 5,283,174 and 5,656,207, the disclosures of these patent documents having been incorporated by reference herein above. Other examples of preferred detectable labels include fluorescent labels, such as fluorescein. Non-nucleotide linkers can be incorporated into any of the loop region, the arm structures, or even the inversion linkages of the inversion probes as long as the presence of the linker does not prevent hybrid formation between the probe and its target polynucleotide.

This invention has been described with reference to a number of specific examples and embodiments thereof. Of course, a number of different embodiments of the present invention will suggest themselves to those having ordinary skill in the art upon review of the foregoing detailed description. Thus, the true scope of the present invention is to be determined upon reference to the appended claims.

What is claimed is:

1. A hybridization probe for detecting a target polynucleotide, comprising:
   (a) a loop comprising a target-complementary sequence of bases joined to a loop backbone, said target-complementary sequence of bases extending from a first boundary to a second boundary;
   (b) a first arm joined to said target-complementary sequence of bases at said first boundary through a first arm linkage, said first arm comprising a first arm sequence of bases joined to a first arm backbone;
   (c) a second arm joined to said target-complementary sequence of bases at said second boundary through a second arm linkage, said second arm comprising a second arm sequence of bases joined to a second arm backbone;
       wherein both of said first arm linkage and said second arm linkage are inversion linkages different from each other, said hybridization probe being a dual inversion probe, each of said inversion linkages optionally including a non-nucleotide linker, and
   (d) at least one detectable label joined to said loop, said first arm, said second arm or, said non-nucleotide linker,
       wherein said first arm and said second arm interact with each other in the absence of said target polynucleotide to form a stem duplex.

2. The hybridization probe of claim 1, wherein said at least one detectable label comprises a pair of interactive labels comprising a first label and a second label, said first label being joined to said first arm and said second label being joined to said second arm.

3. The hybridization probe of claim 1, wherein said first arm linkage is a 3'-3' inversion linkage, and wherein said second arm linkage is a 5'-5' inversion linkage.

4. The hybridization probe of claim 1, wherein said first arm linkage is a 5'-5' inversion linkage, and wherein said second arm linkage is a 3'-3' inversion linkage.

5. The hybridization probe of claim 2, wherein at least one of said loop, said first arm or said second arm comprise at least one nucleotide analog.

6. The hybridization probe of claim 5, wherein said loop comprises 2'-methoxy nucleotide analogs.

7. The hybridization probe of claim 2, wherein the target-complementary sequence of bases has a length in the range of 10–25 bases.

8. The hybridization probe of claim 7, wherein the target-complementary sequence of bases has a length in the range of 16–22 bases.

9. The hybridization probe of claim 7, wherein the first arm has a length of 5–12 bases.

10. The hybridization probe of claim 9, wherein the second arm has a length of 5–12 bases.

11. The hybridization probe of claim 7, wherein both the first arm and the second arm have lengths in the range of 6–8 bases.

12. The hybridization probe of claim 2, wherein said pair of interactive labels is a pair of FRET interactive labels.

13. The hybridization probe of claim 2, wherein said pair of interactive labels is a pair of non-FRET interactive labels.

14. The hybridization probe of claim 13, wherein one member of said pair of non-FRET interactive labels comprises fluorescein.

15. The hybridization probe of claim 10, wherein said pair of interactive labels is a pair of FRET interactive labels.

16. The hybridization probe of claim 10, wherein said pair of interactive labels is a pair of non-FRET interactive labels.

17. A method of determining whether a test sample contains a target polynucleotide, comprising the steps of:
   (a) providing a hybridization probe of claim 1,
   (b) contacting said hybridization probe with said target polynucleotide in the test sample under hybridization-promoting conditions; and
   (c) detecting the formation of hybrid duplexes comprising said hybridization probe and said target polynucleotide as an indication of the presence of said target polynucleotide sequence in said test sample.

18. A kit for detecting a target polynucleotide sequence using a hybridization assay, comprising:
   (a) a hybridization probe of claim 1; and
   (b) a positive-control target polynucleotide having a sequence complementary to said target-complementary sequence of bases of said loop.

19. The kit of claim 18, further comprising
   (c) a hybridization solution.

* * * * *

SEQUENCE LISTING

```
<160> NUMBER OF SEQ ID NOS: 36

<210> SEQ ID NO 1
<211> LENGTH: 28
<212> TYPE: DNA
<213> ORGANISM: HIV-1
<220> FEATURE:
<221> NAME/KEY: misc_feature
<222> LOCATION: (7)...(22)
<223> OTHER INFORMATION: HIV-1 target-complementary sequence of 2'-OMe
      analogs
<220> FEATURE:
<221> NAME/KEY: misc_feature
<222> LOCATION: (1)...(6)
<223> OTHER INFORMATION: DNA backbone
<220> FEATURE:
<221> NAME/KEY: misc_feature
<222> LOCATION: (23)...(28)
<223> OTHER INFORMATION: DNA backbone
<220> FEATURE:
<221> NAME/KEY: misc_feature
<222> LOCATION: (3)...(3)
<223> OTHER INFORMATION: Position occupied by T
<220> FEATURE:
<221> NAME/KEY: misc_feature
<222> LOCATION: (5)...(5)
```

<223> OTHER INFORMATION: Position occupied by T
<220> FEATURE:
<221> NAME/KEY: misc_feature
<222> LOCATION: (1)...(28)
<223> OTHER INFORMATION: Molecule is combined DNA/RNA

<400> SEQUENCE: 1
ggngnggggu acagugcagg ggcacacc                                28

<210> SEQ ID NO 2
<211> LENGTH: 28
<212> TYPE: DNA
<213> ORGANISM: HIV-1
<220> FEATURE:
<221> NAME/KEY: misc_feature
<222> LOCATION: (7)...(22)
<223> OTHER INFORMATION: HIV-1 target-complementary sequence of 2'-OMe
      analogs
<220> FEATURE:
<221> NAME/KEY: misc_feature
<222> LOCATION: (1)...(6)
<223> OTHER INFORMATION: DNA backbone
<220> FEATURE:
<221> NAME/KEY: misc_feature
<222> LOCATION: (23)...(28)
<223> OTHER INFORMATION: DNA backbone
<220> FEATURE:
<221> NAME/KEY: misc_feature
<222> LOCATION: (6)...(7)
<223> OTHER INFORMATION: 5'-5' inversion linkage
<220> FEATURE:
<221> NAME/KEY: modified_base
<222> LOCATION: (3)...(3)
<223> OTHER INFORMATION: Position occupied by T
<220> FEATURE:
<221> NAME/KEY: modified_base
<222> LOCATION: (5)...(5)
<223> OTHER INFORMATION: Position occupied by T
<220> FEATURE:
<221> NAME/KEY: misc_feature
<222> LOCATION: (1)...(28)
<223> OTHER INFORMATION: Molecule is combined DNA/RNA

<400> SEQUENCE: 2
ggngnggggu acagugcagg ggcacacc                                28

<210> SEQ ID NO 3
<211> LENGTH: 28
<212> TYPE: DNA
<213> ORGANISM: HIV-1
<220> FEATURE:
<221> NAME/KEY: misc_feature
<222> LOCATION: (7)...(22)
<223> OTHER INFORMATION: HIV-1 target-complementary sequence of 2'-OMe
      analogs
<220> FEATURE:
<221> NAME/KEY: misc_feature
<222> LOCATION: (1)...(6)
<223> OTHER INFORMATION: DNA backbone
<220> FEATURE:
<221> NAME/KEY: misc_feature
<222> LOCATION: (23)...(28)
<223> OTHER INFORMATION: DNA backbone
<220> FEATURE:
<221> NAME/KEY: modified_base
<222> LOCATION: (23)...(23)
<223> OTHER INFORMATION: Position occupied by 2'-deoxy-5-
      methylisocytidine
<220> FEATURE:
<221> NAME/KEY: modified_base
<222> LOCATION: (25)...(25)
<223> OTHER INFORMATION: Position occupied by 2'-deoxy-5-
      methylisocytidine
<220> FEATURE:
<221> NAME/KEY: modified_base

```
<222> LOCATION: (27)...(27)
<223> OTHER INFORMATION: Position occupied by 2'-deoxy-5-
      methylisocytidine
<220> FEATURE:
<221> NAME/KEY: modified_base
<222> LOCATION: (28)...(28)
<223> OTHER INFORMATION: Position occupied by 2'-deoxy-5-
      methylisocytidine
<220> FEATURE:
<221> NAME/KEY: modified_base
<222> LOCATION: (3)...(3)
<223> OTHER INFORMATION: Position occupied by T
<220> FEATURE:
<221> NAME/KEY: modified_base
<222> LOCATION: (5)...(5)
<223> OTHER INFORMATION: Position occupied by T
<220> FEATURE:
<221> NAME/KEY: misc_feature
<222> LOCATION: (1)...(28)
<223> OTHER INFORMATION: Molecule is combined DNA/RNA

<400> SEQUENCE: 3
ggngnggggu acagugcagg ggnanann                               28

<210> SEQ ID NO 4
<211> LENGTH: 31
<212> TYPE: RNA
<213> ORGANISM: HIV-1

<400> SEQUENCE: 4
uauucuuucc ccugcacugu acccccaau c                            31

<210> SEQ ID NO 5
<211> LENGTH: 31
<212> TYPE: RNA
<213> ORGANISM: HIV-1

<400> SEQUENCE: 5
uaggugugcc ccugcacugu accccacacc u                           31

<210> SEQ ID NO 6
<211> LENGTH: 40
<212> TYPE: DNA
<213> ORGANISM: Hepatitis B Virus
<220> FEATURE:
<221> NAME/KEY: misc_feature
<222> LOCATION: (13)...(28)
<223> OTHER INFORMATION: HBV target-complementary sequence

<400> SEQUENCE: 6
aaaaaaaaaa aagcaggatg aagaggaatt tttttttttt                  40

<210> SEQ ID NO 7
<211> LENGTH: 57
<212> TYPE: DNA
<213> ORGANISM: Hepatitis B Virus

<400> SEQUENCE: 7
gtctgcggcg ttttatcata ttcctcttca tcctgctgct atgcctcatc ttcttat    57

<210> SEQ ID NO 8
<211> LENGTH: 40
<212> TYPE: DNA
<213> ORGANISM: Hepatitis B Virus
<220> FEATURE:
<221> NAME/KEY: misc_feature
<222> LOCATION: (13)...(28)
<223> OTHER INFORMATION: HBV target-complementary sequence
<220> FEATURE:
```

```
<221> NAME/KEY: misc_feature
<222> LOCATION: (28)...(29)
<223> OTHER INFORMATION: 3'-3' inversion linkage

<400> SEQUENCE: 8
aaaaaaaaaa aagcaggatg aagaggaatt tttttttttt                              40

<210> SEQ ID NO 9
<211> LENGTH: 16
<212> TYPE: RNA
<213> ORGANISM: HIV-1

<400> SEQUENCE: 9
ggguacagug cagggg                                                        16

<210> SEQ ID NO 10
<211> LENGTH: 16
<212> TYPE: DNA
<213> ORGANISM: Hepatitis B Virus

<400> SEQUENCE: 10
gcaggatgaa gaggaa                                                        16

<210> SEQ ID NO 11
<211> LENGTH: 32
<212> TYPE: DNA
<213> ORGANISM: Artificial Sequence
<220> FEATURE:
<221> NAME/KEY: misc_feature
<222> LOCATION: (1)...(8)
<223> OTHER INFORMATION: DNA backbone
<220> FEATURE:
<221> NAME/KEY: misc_feature
<222> LOCATION: (25)...(32)
<223> OTHER INFORMATION: DNA backbone
<220> FEATURE:
<221> NAME/KEY: modified_base
<222> LOCATION: (26)...(26)
<223> OTHER INFORMATION: Position occupied by T
<220> FEATURE:
<221> NAME/KEY: modified_base
<222> LOCATION: (26)...(26)
<223> OTHER INFORMATION: Position occupied by T
<220> FEATURE:
<221> NAME/KEY: modified_base
<222> LOCATION: (29)...(29)
<223> OTHER INFORMATION: Position occupied by T
<220> FEATURE:
<221> NAME/KEY: misc_feature
<222> LOCATION: (9)...(24)
<223> OTHER INFORMATION: Pan-bacterial target-complementary sequence of
      2'-OMe analogs
<221> NAME/KEY: misc_feature
<222> LOCATION: (1)...(32)
<223> OTHER INFORMATION: Molecule is combined DNA/RNA
<220> FEATURE:
<223> OTHER INFORMATION: Sequence hybridizes to ribosomal nucleic acids
      of pan-bacterial organisms

<400> SEQUENCE: 11
ccgaggaccg acaaggaauu ucgcgnccnc gg                                      32

<210> SEQ ID NO 12
<211> LENGTH: 32
<212> TYPE: DNA
<213> ORGANISM: Artificial Sequence
<220> FEATURE:
<221> NAME/KEY: misc_feature
<222> LOCATION: (1)...(8)
<223> OTHER INFORMATION: DNA backbone
<220> FEATURE:
```

```
<221> NAME/KEY: misc_feature
<222> LOCATION: (25)...(32)
<223> OTHER INFORMATION: DNA backbone
<220> FEATURE:
<221> NAME/KEY: modified_base
<222> LOCATION: (4)...(4)
<223> OTHER INFORMATION: Position occupied by T
<220> FEATURE:
<221> NAME/KEY: modified_base
<222> LOCATION: (7)...(7)
<223> OTHER INFORMATION: Position occupied by T
<220> FEATURE:
<221> NAME/KEY: misc_feature
<222> LOCATION: (9)...(24)
<223> OTHER INFORMATION: Pan-bacterial target-complementary sequence of
      2'-OMe analogs
<220> FEATURE:
<221> NAME/KEY: misc_feature
<222> LOCATION: (8)...(9)
<223> OTHER INFORMATION: 3'-3' inversion linkage
<220> FEATURE:
<221> NAME/KEY: misc_feature
<222> LOCATION: (24)...(25)
<223> OTHER INFORMATION: 5'-5' inversion linkage
<221> NAME/KEY: misc_feature
<222> LOCATION: (1)...(32)
<223> OTHER INFORMATION: Molecule is combined DNA/RNA
<220> FEATURE:
<223> OTHER INFORMATION: Sequence hybridizes to ribosomal nucleic acids
      of pan-bacterial organisms

<400> SEQUENCE: 12
ggcnccngcg cuuuaaggaa cagccaggag cc                                       32

<210> SEQ ID NO 13
<211> LENGTH: 62
<212> TYPE: RNA
<213> ORGANISM: Artificial Sequence
<220> FEATURE:
<223> OTHER INFORMATION: Sequence hybridizes to ribosomal nucleic acids
      of pan-bacterial organisms

<400> SEQUENCE: 13
ggccguaccu auaacggucc uaagguagcg aaauuccuug ucggguaagu uccgaccugc         60
ac                                                                       62

<210> SEQ ID NO 14
<211> LENGTH: 62
<212> TYPE: RNA
<213> ORGANISM: Artificial Sequence
<220> FEATURE:
<223> OTHER INFORMATION: Sequence hybridizes to ribosomal nucleic acids
      of pan-bacterial organisms

<400> SEQUENCE: 14
ggccguaccu auaacggucc cgaggacgcg aaauuccuug ucgguccucg gccgaccugc         60
ac                                                                       62

<210> SEQ ID NO 15
<211> LENGTH: 38
<212> TYPE: DNA
<213> ORGANISM: Artificial Sequence
<220> FEATURE:
<221> NAME/KEY: misc_feature
<222> LOCATION: (1)...(8)
<223> OTHER INFORMATION: DNA backbone
<220> FEATURE:
<221> NAME/KEY: misc_feature
<222> LOCATION: (31)...(38)
<223> OTHER INFORMATION: DNA backbone
<220> FEATURE:
```

```
<221> NAME/KEY: modified_base
<222> LOCATION: (32)...(32)
<223> OTHER INFORMATION: Position occupied by T
<220> FEATURE:
<221> NAME/KEY: modified_base
<222> LOCATION: (35)...(35)
<223> OTHER INFORMATION: Position occupied by T
<220> FEATURE:
<221> NAME/KEY: misc_feature
<222> LOCATION: (9)...(30)
<223> OTHER INFORMATION: Pan-fungal target-complementary sequence of 2'-
      OMe analogs
<221> NAME/KEY: misc_feature
<222> LOCATION: (1)...(38)
<223> OTHER INFORMATION: Molecule is combined DNA/RNA
<220> FEATURE:
<223> OTHER INFORMATION: Sequence hybridizes to ribosomal nucleic acids
      of pan-fungal organisms

<400> SEQUENCE: 15
ccgaggacgu cuggaccugg ugaguuuccc gnccncgg                              38

<210> SEQ ID NO 16
<211> LENGTH: 38
<212> TYPE: DNA
<213> ORGANISM: Artificial Sequence
<220> FEATURE:
<221> NAME/KEY: misc_feature
<222> LOCATION: (1)...(8)
<223> OTHER INFORMATION: DNA backbone
<220> FEATURE:
<221> NAME/KEY: misc_feature
<222> LOCATION: (31)...(38)
<223> OTHER INFORMATION: DNA backbone
<220> FEATURE:
<221> NAME/KEY: modified_base
<222> LOCATION: (4)...(4)
<223> OTHER INFORMATION: Position occupied by T
<220> FEATURE:
<221> NAME/KEY: modified_base
<222> LOCATION: (7)...(7)
<223> OTHER INFORMATION: Position occupied by T
<220> FEATURE:
<221> NAME/KEY: misc_feature
<222> LOCATION: (9)...(30)
<223> OTHER INFORMATION: Pan-fungal target-complementary sequence of 2'-
      OMe analogs
<220> FEATURE:
<221> NAME/KEY: misc_feature
<222> LOCATION: (8)...(9)
<223> OTHER INFORMATION: 3'-3' inversion linkage
<220> FEATURE:
<221> NAME/KEY: misc_feature
<222> LOCATION: (30)...(31)
<223> OTHER INFORMATION: 5'-5' inversion linkage
<221> NAME/KEY: misc_feature
<222> LOCATION: (1)...(38)
<223> OTHER INFORMATION: Molecule is combined DNA/RNA
<220> FEATURE:
<223> OTHER INFORMATION: Sequence hybridizes to ribosomal nucleic acids
      of pan-fungal organisms

<400> SEQUENCE: 16
ggcnccngcc cuuugagugg uccaggucug caggagcc                              38

<210> SEQ ID NO 17
<211> LENGTH: 75
<212> TYPE: RNA
<213> ORGANISM: Artificial Sequence
<220> FEATURE:
<223> OTHER INFORMATION: Sequence hybridizes to ribosomal nucleic acids
      of pan-fungal organisms

<400> SEQUENCE: 17
```

```
cugcggcuua auuugacuca acacggggaa acucaccagg uccagacaca auaaggauug      60
acagauugag agcuc                                                      75

<210> SEQ ID NO 18
<211> LENGTH: 75
<212> TYPE: RNA
<213> ORGANISM: Artificial Sequence
<220> FEATURE:
<223> OTHER INFORMATION: Sequence hybridizes to ribosomal nucleic acids
      of pan-fungal organisms

<400> SEQUENCE: 18
cugcggcuua auuugacccg aggacgggaa acucaccagg uccagacguc cuccggauug      60
acagauugag agcuc                                                      75

<210> SEQ ID NO 19
<211> LENGTH: 33
<212> TYPE: DNA
<213> ORGANISM: Artificial Sequence
<220> FEATURE:
<221> NAME/KEY: misc_feature
<222> LOCATION: (1)...(8)
<223> OTHER INFORMATION: DNA backbone
<220> FEATURE:
<221> NAME/KEY: misc_feature
<222> LOCATION: (26)...(33)
<223> OTHER INFORMATION: DNA backbone
<220> FEATURE:
<221> NAME/KEY: modified_base
<222> LOCATION: (27)...(27)
<223> OTHER INFORMATION: Position occupied by T
<220> FEATURE:
<221> NAME/KEY: modified_base
<222> LOCATION: (30)...(30)
<223> OTHER INFORMATION: Position occupied by T
<220> FEATURE:
<221> NAME/KEY: misc_feature
<222> LOCATION: (9)...(25)
<223> OTHER INFORMATION: Enterobacteriaceae target-complementary
      sequence of 2'-OMe analogs
<221> NAME/KEY: misc_feature
<222> LOCATION: (1)...(33)
<223> OTHER INFORMATION: Molecule is combined DNA/RNA
<220> FEATURE:
<223> OTHER INFORMATION: Sequence hybridizes to ribosomal nucleic acids
      of Enterobacteriaceae organisms

<400> SEQUENCE: 19
ccgaggaccc gcuugcucuc gcgaggnccn cgg                                   33

<210> SEQ ID NO 20
<211> LENGTH: 33
<212> TYPE: DNA
<213> ORGANISM: Artificial Sequence
<220> FEATURE:
<221> NAME/KEY: misc_feature
<222> LOCATION: (1)...(8)
<223> OTHER INFORMATION: DNA backbone
<220> FEATURE:
<221> NAME/KEY: misc_feature
<222> LOCATION: (26)...(33)
<223> OTHER INFORMATION: DNA backbone
<220> FEATURE:
<221> NAME/KEY: modified_base
<222> LOCATION: (4)...(4)
<223> OTHER INFORMATION: Position occupied by T
<220> FEATURE:
<221> NAME/KEY: modified_base
<222> LOCATION: (7)...(7)
<223> OTHER INFORMATION: Position occupied by T
<220> FEATURE:
<221> NAME/KEY: misc_feature
```

```
<222> LOCATION: (9)...(25)
<223> OTHER INFORMATION: Enterobacteriaceae target-complementary
      sequence of 2'-OMe analogs
<220> FEATURE:
<221> NAME/KEY: misc_feature
<222> LOCATION: (8)...(9)
<223> OTHER INFORMATION: 3'-3' inversion linkage
<220> FEATURE:
<221> NAME/KEY: misc_feature
<222> LOCATION: (25)...(26)
<223> OTHER INFORMATION: 5'-5' inversion linkage
<221> NAME/KEY: misc_feature
<222> LOCATION: (1)...(33)
<223> OTHER INFORMATION: Molecule is combined DNA/RNA
<220> FEATURE:
<223> OTHER INFORMATION: Sequence hybridizes to ribosomal nucleic acids
      of Enterobacteriaceae organisms

<400> SEQUENCE: 20
ggcnccngga gcgcucucgu ucgcccagga gcc                              33

<210> SEQ ID NO 21
<211> LENGTH: 86
<212> TYPE: RNA
<213> ORGANISM: Artificial Sequence
<220> FEATURE:
<223> OTHER INFORMATION: Sequence hybridizes to ribosomal nucleic acids
      of Enterobacteriaceae organisms

<400> SEQUENCE: 21
gggcuacaca cgugcuacaa uggcgcauac aaagagaagc gaccucgcga gagcaagcgg    60
accucauaaa gugcgucgua guccgg                                         86

<210> SEQ ID NO 22
<211> LENGTH: 86
<212> TYPE: RNA
<213> ORGANISM: Artificial Sequence
<220> FEATURE:
<223> OTHER INFORMATION: Sequence hybridizes to ribosomal nucleic acids
      of Enterobacteriaceae organisms

<400> SEQUENCE: 22
gggcuacaca cgugcuacaa uggcgcauac aaagaccgag gaccucgcga gagcaagcgg    60
guccucggaa gugcgucgua guccgg                                         86

<210> SEQ ID NO 23
<211> LENGTH: 34
<212> TYPE: DNA
<213> ORGANISM: Artificial Sequence
<220> FEATURE:
<221> NAME/KEY: misc_feature
<222> LOCATION: (1)...(8)
<223> OTHER INFORMATION: DNA backbone
<220> FEATURE:
<221> NAME/KEY: misc_feature
<222> LOCATION: (27)...(34)
<223> OTHER INFORMATION: DNA backbone
<220> FEATURE:
<221> NAME/KEY: modified_base
<222> LOCATION: (28)...(28)
<223> OTHER INFORMATION: Position occupied by T
<220> FEATURE:
<221> NAME/KEY: modified_base
<222> LOCATION: (31)...(31)
<223> OTHER INFORMATION: Position occupied by T
<220> FEATURE:
<221> NAME/KEY: misc_feature
<222> LOCATION: (9)...(26)
<223> OTHER INFORMATION: Gram positive bacterial target-complementary
      sequence of 2'-OMe analogs
<221> NAME/KEY: misc_feature
```

```
<222> LOCATION: (1)...(34)
<223> OTHER INFORMATION: Molecule is combined DNA/RNA
<220> FEATURE:
<223> OTHER INFORMATION: Sequence hybridizes to ribosomal nucleic acids
      of Gram positive bacterial organisms

<400> SEQUENCE: 23
ccgaggacga gggaaccuuu gggcgcgncc ncgg                            34

<210> SEQ ID NO 24
<211> LENGTH: 34
<212> TYPE: DNA
<213> ORGANISM: Artificial Sequence
<220> FEATURE:
<221> NAME/KEY: misc_feature
<222> LOCATION: (1)...(8)
<223> OTHER INFORMATION: DNA backbone
<220> FEATURE:
<221> NAME/KEY: misc_feature
<222> LOCATION: (27)...(34)
<223> OTHER INFORMATION: DNA backbone
<220> FEATURE:
<221> NAME/KEY: modified_base
<222> LOCATION: (4)...(4)
<223> OTHER INFORMATION: Position occupied by T
<220> FEATURE:
<221> NAME/KEY: modified_base
<222> LOCATION: (7)...(7)
<223> OTHER INFORMATION: Position occupied by T
<220> FEATURE:
<221> NAME/KEY: misc_feature
<222> LOCATION: (9)...(26)
<223> OTHER INFORMATION: Gram positive bacterial target-complementary
      sequence of 2'-OMe analogs
<220> FEATURE:
<221> NAME/KEY: misc_feature
<222> LOCATION: (8)...(9)
<223> OTHER INFORMATION: 3'-3' inversion linkage
<220> FEATURE:
<221> NAME/KEY: misc_feature
<222> LOCATION: (26)...(27)
<223> OTHER INFORMATION: 5'-5' inversion linkage
<221> NAME/KEY: misc_feature
<222> LOCATION: (1)...(34)
<223> OTHER INFORMATION: Molecule is combined DNA/RNA
<220> FEATURE:
<223> OTHER INFORMATION: Sequence hybridizes to ribosomal nucleic acids
      of Gram positive bacterial organisms

<400> SEQUENCE: 24
ggcnccngcg cggguuucca agggagcagg agcc                            34

<210> SEQ ID NO 25
<211> LENGTH: 72
<212> TYPE: RNA
<213> ORGANISM: Artificial Sequence
<220> FEATURE:
<223> OTHER INFORMATION: Sequence hybridizes to ribosomal nucleic acids
      of Gram positive bacterial organisms

<400> SEQUENCE: 25
uggggcgguu gccuccuaaa gaguaacgga ggcgcccaaa gguucccuca gccuggucgg   60
caaucaggug uu                                                      72

<210> SEQ ID NO 26
<211> LENGTH: 72
<212> TYPE: RNA
<213> ORGANISM: Artificial Sequence
<220> FEATURE:
<223> OTHER INFORMATION: Sequence hybridizes to ribosomal nucleic acids
      of Gram positive bacterial organisms
```

-continued

```
<400> SEQUENCE: 26 ugggggcgguu gccuccuaaa gagccgagga cgcgcccaaa gguucccucg uccucggcgg    60
caaucaggug uu                                                         72

<210> SEQ ID NO 27
<211> LENGTH: 28
<212> TYPE: DNA
<213> ORGANISM: HIV-1
<220> FEATURE:
<221> NAME/KEY: misc_feature
<222> LOCATION: (1)...(6)
<223> OTHER INFORMATION: DNA backbone
<220> FEATURE:
<221> NAME/KEY: misc_feature
<222> LOCATION: (23)...(28)
<223> OTHER INFORMATION: DNA backbone
<220> FEATURE:
<221> NAME/KEY: modified_base
<222> LOCATION: (3)...(3)
<223> OTHER INFORMATION: Position occupied by T
<220> FEATURE:
<221> NAME/KEY: modified_base
<222> LOCATION: (5)...(5)
<223> OTHER INFORMATION: Position occupied by T
<220> FEATURE:
<221> NAME/KEY: misc_feature
<222> LOCATION: (7)...(22)
<223> OTHER INFORMATION: HIV-1 target-complementary sequence of 2'-OMe
      analogs
<220> FEATURE:
<221> NAME/KEY: misc_feature
<222> LOCATION: (1)...(28)
<223> OTHER INFORMATION: Molecule is combined DNA/RNA

<400> SEQUENCE: 27
ggngnggggu acagugcagg ggcacacc                                        28

<210> SEQ ID NO 28
<211> LENGTH: 28
<212> TYPE: DNA
<213> ORGANISM: HIV-1
<220> FEATURE:
<221> NAME/KEY: misc_feature
<222> LOCATION: (1)...(6)
<223> OTHER INFORMATION: DNA backbone
<220> FEATURE:
<221> NAME/KEY: misc_feature
<222> LOCATION: (23)...(28)
<223> OTHER INFORMATION: DNA backbone
<220> FEATURE:
<221> NAME/KEY: modified_base
<222> LOCATION: (3)...(3)
<223> OTHER INFORMATION: Position occupied by T
<220> FEATURE:
<221> NAME/KEY: modified_base
<222> LOCATION: (5)...(5)
<223> OTHER INFORMATION: Position occupied by T
<220> FEATURE:
<221> NAME/KEY: misc_feature
<222> LOCATION: (7)...(22)
<223> OTHER INFORMATION: HIV-1 target-complementary sequence of 2'-OMe
      analogs
<220> FEATURE:
<221> NAME/KEY: misc_feature
<222> LOCATION: (6)...(7)
<223> OTHER INFORMATION: 3'-3' inversion linkage
<220> FEATURE:
<221> NAME/KEY: misc_feature
<222> LOCATION: (22)...(23)
<223> OTHER INFORMATION: 5'-5' inversion linkage
<220> FEATURE:
<221> NAME/KEY: misc_feature
<222> LOCATION: (1)...(28)
<223> OTHER INFORMATION: Molecule is combined DNA/RNA
```

<400> SEQUENCE: 28
ggngnggggu acagugcagg ggcacacc                      28

<210> SEQ ID NO 29
<211> LENGTH: 28
<212> TYPE: DNA
<213> ORGANISM: HIV-1
<220> FEATURE:
<221> NAME/KEY: misc_feature
<222> LOCATION: (1)...(6)
<223> OTHER INFORMATION: DNA backbone
<220> FEATURE:
<221> NAME/KEY: misc_feature
<222> LOCATION: (23)...(28)
<223> OTHER INFORMATION: DNA backbone
<220> FEATURE:
<221> NAME/KEY: modified_base
<222> LOCATION: (3)...(3)
<223> OTHER INFORMATION: Position occupied by T
<220> FEATURE:
<221> NAME/KEY: modified_base
<222> LOCATION: (5)...(5)
<223> OTHER INFORMATION: Position occupied by T
<220> FEATURE:
<221> NAME/KEY: misc_feature
<222> LOCATION: (7)...(22)
<223> OTHER INFORMATION: HIV-1 target-complementary sequence of 2'-OMe
      analogs
<220> FEATURE:
<221> NAME/KEY: misc_feature
<222> LOCATION: (6)...(7)
<223> OTHER INFORMATION: 3'-3' inversion linkage
<220> FEATURE:
<221> NAME/KEY: misc_feature
<222> LOCATION: (22)...(23)
<223> OTHER INFORMATION: 5'-5' inversion linkage
<220> FEATURE:
<221> NAME/KEY: misc_feature
<222> LOCATION: (6)...(7)
<223> OTHER INFORMATION: Inversion linkage includes chemical spacer
<220> FEATURE:
<221> NAME/KEY: misc_feature
<222> LOCATION: (1)...(28)
<223> OTHER INFORMATION: Molecule is combined DNA/RNA

<400> SEQUENCE: 29
ggngnggggu acagugcagg ggcacacc                      28

<210> SEQ ID NO 30
<211> LENGTH: 28
<212> TYPE: DNA
<213> ORGANISM: HIV-1
<220> FEATURE:
<221> NAME/KEY: misc_feature
<222> LOCATION: (1)...(6)
<223> OTHER INFORMATION: DNA backbone
<220> FEATURE:
<221> NAME/KEY: misc_feature
<222> LOCATION: (23)...(28)
<223> OTHER INFORMATION: DNA backbone
<220> FEATURE:
<221> NAME/KEY: modified_base
<222> LOCATION: (3)...(3)
<223> OTHER INFORMATION: Position occupied by T
<220> FEATURE:
<221> NAME/KEY: modified_base
<222> LOCATION: (5)...(5)
<223> OTHER INFORMATION: Position occupied by T
<220> FEATURE:
<221> NAME/KEY: misc_feature
<222> LOCATION: (7)...(22)
<223> OTHER INFORMATION: HIV-1 target-complementary sequence of 2'-OMe
      analogs
<220> FEATURE:

```
<221> NAME/KEY: misc_feature
<222> LOCATION: (6)...(7)
<223> OTHER INFORMATION: 3'-3' inversion linkage
<220> FEATURE:
<221> NAME/KEY: misc_feature
<222> LOCATION: (22)...(23)
<223> OTHER INFORMATION: 5'-5' inversion linkage
<220> FEATURE:
<221> NAME/KEY: misc_feature
<222> LOCATION: (22)...(23)
<223> OTHER INFORMATION: Inversion linkage includes chemical spacer
<220> FEATURE:
<221> NAME/KEY: misc_feature
<222> LOCATION: (1)...(28)
<223> OTHER INFORMATION: Molecule is combined DNA/RNA

<400> SEQUENCE: 30 ggngngggu acagugcagg ggcacacc                                          28

<210> SEQ ID NO 31
<211> LENGTH: 28
<212> TYPE: DNA
<213> ORGANISM: HIV-1
<220> FEATURE:
<221> NAME/KEY: misc_feature
<222> LOCATION: (1)...(6)
<223> OTHER INFORMATION: DNA backbone
<220> FEATURE:
<221> NAME/KEY: misc_feature
<222> LOCATION: (23)...(28)
<223> OTHER INFORMATION: DNA backbone
<220> FEATURE:
<221> NAME/KEY: modified_base
<222> LOCATION: (3)...(3)
<223> OTHER INFORMATION: Position occupied by T
<220> FEATURE:
<221> NAME/KEY: modified_base
<222> LOCATION: (5)...(5)
<223> OTHER INFORMATION: Position occupied by T
<220> FEATURE:
<221> NAME/KEY: misc_feature
<222> LOCATION: (7)...(22)
<223> OTHER INFORMATION: HIV-1 target-complementary sequence of 2'-OMe
      analogs
<220> FEATURE:
<221> NAME/KEY: misc_feature
<222> LOCATION: (6)...(7)
<223> OTHER INFORMATION: 3'-3' inversion linkage
<220> FEATURE:
<221> NAME/KEY: misc_feature
<222> LOCATION: (22)...(23)
<223> OTHER INFORMATION: 5'-5' inversion linkage
<220> FEATURE:
<221> NAME/KEY: misc_feature
<222> LOCATION: (6)...(7)
<223> OTHER INFORMATION: Inversion linkage includes chemical spacer
<220> FEATURE:
<221> NAME/KEY: misc_feature
<222> LOCATION: (1)...(28)
<223> OTHER INFORMATION: Molecule is combined DNA/RNA

<400> SEQUENCE: 31 ggngngggu acagugcagg ggcacacc                                          28

<210> SEQ ID NO 32
<211> LENGTH: 28
<212> TYPE: DNA
<213> ORGANISM: HIV-1
<220> FEATURE:
<221> NAME/KEY: misc_feature
<222> LOCATION: (1)...(6)
<223> OTHER INFORMATION: DNA backbone
<220> FEATURE:
<221> NAME/KEY: misc_feature
<222> LOCATION: (23)...(28)
```

```
<223> OTHER INFORMATION: DNA backbone
<220> FEATURE:
<221> NAME/KEY: modified_base
<222> LOCATION: (3)...(3)
<223> OTHER INFORMATION: Position occupied by T
<220> FEATURE:
<221> NAME/KEY: modified_base
<222> LOCATION: (5)...(5)
<223> OTHER INFORMATION: Position occupied by T
<220> FEATURE:
<221> NAME/KEY: misc_feature
<222> LOCATION: (7)...(22)
<223> OTHER INFORMATION: HIV-1 target-complementary sequence of 2'-OMe
      analogs
<220> FEATURE:
<221> NAME/KEY: misc_feature
<222> LOCATION: (6)...(7)
<223> OTHER INFORMATION: 3'-3' inversion linkage
<220> FEATURE:
<221> NAME/KEY: misc_feature
<222> LOCATION: (22)...(23)
<223> OTHER INFORMATION: 5'-5' inversion linkage
<220> FEATURE:
<221> NAME/KEY: misc_feature
<222> LOCATION: (22)...(23)
<223> OTHER INFORMATION: Inversion linkage includes chemical spacer
<220> FEATURE:
<221> NAME/KEY: misc_feature
<222> LOCATION: (1)...(28)
<223> OTHER INFORMATION: Molecule is combined DNA/RNA

<400> SEQUENCE: 32 ggngngggu  acagugcagg  ggcacacc                                     28

<210> SEQ ID NO 33
<211> LENGTH: 28
<212> TYPE: DNA
<213> ORGANISM: HIV-1
<220> FEATURE:
<221> NAME/KEY: misc_feature
<222> LOCATION: (1)...(6)
<223> OTHER INFORMATION: DNA backbone
<220> FEATURE:
<221> NAME/KEY: misc_feature
<222> LOCATION: (23)...(28)
<223> OTHER INFORMATION: DNA backbone
<220> FEATURE:
<221> NAME/KEY: modified_base
<222> LOCATION: (3)...(3)
<223> OTHER INFORMATION: Position occupied by T
<220> FEATURE:
<221> NAME/KEY: modified_base
<222> LOCATION: (5)...(5)
<223> OTHER INFORMATION: Position occupied by T
<220> FEATURE:
<221> NAME/KEY: misc_feature
<222> LOCATION: (7)...(22)
<223> OTHER INFORMATION: HIV-1 target-complementary sequence of 2'-OMe
      analogs
<220> FEATURE:
<221> NAME/KEY: misc_feature
<222> LOCATION: (6)...(7)
<223> OTHER INFORMATION: 3'-3' inversion linkage
<220> FEATURE:
<221> NAME/KEY: misc_feature
<222> LOCATION: (22)...(23)
<223> OTHER INFORMATION: 5'-5' inversion linkage
<220> FEATURE:
<221> NAME/KEY: misc_feature
<222> LOCATION: (6)...(7)
<223> OTHER INFORMATION: Inversion linkage includes chemical spacer
<220> FEATURE:
<221> NAME/KEY: misc_feature
<222> LOCATION: (22)...(23)
<223> OTHER INFORMATION: Inversion linkage includes chemical spacer
<220> FEATURE:
<221> NAME/KEY: misc_feature
```

```
<222> LOCATION: (1)...(28)
<223> OTHER INFORMATION: Molecule is combined DNA/RNA

<400> SEQUENCE: 33
ggngnggggu acagugcagg ggcacacc                                          28

<210> SEQ ID NO 34
<211> LENGTH: 28
<212> TYPE: DNA
<213> ORGANISM: HIV-1
<220> FEATURE:
<221> NAME/KEY: misc_feature
<222> LOCATION: (1)...(6)
<223> OTHER INFORMATION: DNA backbone
<220> FEATURE:
<221> NAME/KEY: misc_feature
<222> LOCATION: (23)...(28)
<223> OTHER INFORMATION: DNA backbone
<220> FEATURE:
<221> NAME/KEY: modified_base
<222> LOCATION: (3)...(3)
<223> OTHER INFORMATION: Position occupied by T
<220> FEATURE:
<221> NAME/KEY: modified_base
<222> LOCATION: (5)...(5)
<223> OTHER INFORMATION: Position occupied by T
<220> FEATURE:
<221> NAME/KEY: misc_feature
<222> LOCATION: (7)...(22)
<223> OTHER INFORMATION: HIV-1 target-complementary sequence of 2'-OMe
      analogs
<220> FEATURE:
<221> NAME/KEY: misc_feature
<222> LOCATION: (6)...(7)
<223> OTHER INFORMATION: 3'-3' inversion linkage
<220> FEATURE:
<221> NAME/KEY: misc_feature
<222> LOCATION: (22)...(23)
<223> OTHER INFORMATION: 5'-5' inversion linkage
<220> FEATURE:
<221> NAME/KEY: misc_feature
<222> LOCATION: (6)...(7)
<223> OTHER INFORMATION: Inversion linkage includes chemical spacer
<220> FEATURE:
<221> NAME/KEY: misc_feature
<222> LOCATION: (22)...(23)
<223> OTHER INFORMATION: Inversion linkage includes chemical spacer
<220> FEATURE:
<221> NAME/KEY: misc_feature
<222> LOCATION: (1)...(28)
<223> OTHER INFORMATION: Molecule is combined DNA/RNA

<400> SEQUENCE: 34
ggngnggggu acagugcagg ggcacacc                                          28

<210> SEQ ID NO 35
<211> LENGTH: 31
<212> TYPE: RNA
<213> ORGANISM: HIV-1
<220> FEATURE:
<221> NAME/KEY: misc_feature
<222> LOCATION: (1)...(31)
<223> OTHER INFORMATION: Sequence of 2'-OMe analogs

<400> SEQUENCE: 35
uaggugugcc ccugcacugu accccacacc u                                      31

<210> SEQ ID NO 36
<211> LENGTH: 31
<212> TYPE: RNA
<213> ORGANISM: HIV-1
<220> FEATURE:
<221> NAME/KEY: misc_feature
```

-continued

```
<222> LOCATION: (1)...(31)
<223> OTHER INFORMATION: Sequence of 2'-OMe analogs

<400> SEQUENCE: 36
uccacacccc augucacguc cccgugugga u                              31
```